United States Patent [19]
Hansen et al.

[11] Patent Number: 6,020,154
[45] Date of Patent: Feb. 1, 2000

[54] H. INFLUENZAE HXUB AND HXUC GENES, PROTEINS AND METHODS OF USE

[75] Inventors: Eric J. Hansen, Plano; Leslie D. Cope, Mesquite; Gregory P. Jarosik, Arlington, all of Tex.; Mark S. Hanson, Columbia, Md.

[73] Assignee: Board of Regents, The University of Texas System, Austin, Tex.

[21] Appl. No.: 08/425,843

[22] Filed: Apr. 20, 1995

[51] Int. Cl.[7] ............................. C12P 21/06; C12N 1/20; C07H 21/04
[52] U.S. Cl. ............... 435/69.1; 435/252.3; 435/252.33; 435/69.3; 536/23.7
[58] Field of Search ................................ 435/69.3, 69.1, 435/252.3, 252.33; 536/23.7

[56] References Cited

U.S. PATENT DOCUMENTS

| | | | |
|---|---|---|---|
| 4,668,624 | 5/1987 | Roberts | 435/68 |
| 5,362,865 | 11/1994 | Austin | 536/24.1 |
| 5,378,619 | 1/1995 | Rogers | 435/172.3 |
| 5,380,655 | 1/1995 | Hansen | 435/172.3 |

OTHER PUBLICATIONS

Database Genbank, Accession No. U09840, submitted May 18, 1994 by Cope et al., available Dec. 7, 1994.

Alberts, B. et al. 'Molecular Biology of the Cell,' Second Edition, published 1989, by Garland Publishing (New York), pp. 262–266, 1989.

Barenkamp and Geme, "Genes Encoding High–Molecular–Weight Adhesion Proteins of Nontypeable *Haemophilus influenzae* Are Part of Gene Clusters," *Infection and Immunity*, 62(8):3320–3328, Aug. 1994.

Braun et al., "*Serratia marcescens* forms a new type of cytolysin," *FEMS Microbiol. Lett*, 100:299–306, 1992.

Cope et al., "The 100 kDa Heme:Hemopexin–Binding Protein of *Haemophilus influenzae* is Present in Soluble Form in Culture Supernatant," Abstracts of the 94th Gen. Meeting of the Am. Soc. for Microbiol., 1994.

Cope et al., "The 100 kDa haem:haemopexin–binding protein of *Haemophilus influenzae:* structure and localization," *Mol. Microbiol.*, 13:863–873, 1994.

Gulig et al., "Immunogenic proteins in cell–free culture supernatants of *Haemophilus influenzae* type b," *Infect. Immun.*, 44:41–48, 1984.

Hannavy and Higgins, "TonB; a model for signal transduction between membranes," *Biochem. Soc. Transact.*, 19:530–532, 1991.

Hanson and Hansen, "Molecular cloning, partial purification, and characterization of a haemin–binding lipoprotein from *Haemophilus influenzae* type b," *Mol. Microbiol.*, 5:267–278, 1991.

Hanson et al., "Identification of a genetic locus of *Haemophilus influenzae* type b necessary for the binding and utilization of heme bound to human hemopexin," *Proc. Natl. Acad. Sci. USA*, 89:1973–1977, 1992.

Heller and Kadner, "Nucleotide sequence of the gene for the vitamin $B_{12}$ receptor protein in the outer membrane of *Escherichia coli,*" *J. Bacteriol.*, 161:904–908, 1985.

Koebnik et al., "The TonB protein of *Yersinia enterocolitica* and its interactions with TonB–box proteins," *Mol. Gen. Genet.*, 237:152–160, 1993.

(List continued on next page.)

*Primary Examiner*—Robert A. Wax
*Assistant Examiner*—Devesh Srivastava
*Attorney, Agent, or Firm*—Arnold, White & Durkee

[57] ABSTRACT

Disclosed are hxuB and hxuC genes and DNA segments from *H. influenzae* such as *H. influenzae* type b (*Hi*b) and nontypeable *H. influenzae* (NT*HI*). The HxuB and HxuC proteins, being surface expressed, are contemplated for use in the preparation of vaccines against pathological *H. influenzae* infections, and in particular, vaccines for use in children and other individuals who respond poorly to capsular-based vaccines. DNA segments encoding these proteins and anti- HxuB and HxuC antibodies will also be of in various screening, diagnostic and therapeutic applications.

77 Claims, 6 Drawing Sheets

OTHER PUBLICATIONS

Jareosik et al., "A functional tonB gene is required for both utilization of heme and virulence expression by *Haemophilus influenzae* type B," *Infect. Immun,* 62:2470–2477, 1994.

Lee, "Isolation of an outer membrane hemin–binding protein of *Haemophilus influenzae* type b," *Infect. Immun,* 60:810–816, 1992.

Litwin and Calderwood, "Role of iron in regulation of virulence genes," *Clin. Microbiol. Rev.,* 6:137–149, 1993.

Lundrigan and Kadner, "Nucleotide sequence of the gene for the ferrienterochelin receptor FepA in *Escherichia coli:* homology among outer membrane receptors that interact with TonB," *J. Biol. Chem,* 261:10797–10801, 1986.

Nau and Konisky, "Evolutionary relationship between the TonB–dependent outer membrane transport proteins: nucleotide and amino acid sequences of the *Escherichia coli* colicin I receptor gene," *J. Bacteriol.,* 171:1041–1047, 1989.

Plaut et al., "Growth of *Haemophilus influenzae* in human milk: Synthesis, distribution, and activity of IgA protease as determined by study of iga+ and mutant iga– cells," *J. Infect Dis,* 166:43–52, 1992.

Poole et al., "Molecular characterization of the hemolysin determinant of *Serratia marcescens,*" *J. Bacteriol.,* 170:3177–3188, 1988.

Postle, "TonB and the Gram–negative dilemma," *Mol. Microbiol.,* 4:2019–2025, 1990.

Schiebel et al., "Subcellular location and unique secretion of the hemolysin of *Serratia marcescens,*" *J. Biol. Chem.,* 264:16311–16320, 1989.

Sjostrom et al., "Signal peptide amino acid sequences in *Escherichia coli* contain information related to final protein localization: A multivariate data analysis," *EMBO J.,* 6:823–831, 1987.

Stojiljkovic and Hantke, "Hemin uptake system of *Yersinia enterocolitica:* similarities with other TonB–dependent systems in Gram–negative bacteria," *EMBO J.,* 11:4359–4367, 1992.

Stull, "Protein sources of heme for *Haemophilus influenzae,*" *Infect. Immun.,* 55:148–153, 1987.

Uphoff and Welch, "Nucleotide sequencing of the *Proteus mirabilis* calcium–independent hemolysin genes (hmpA and hpmB) reveals sequence similarity with the *Serratia marcescens* hemolysin genes (sh1A and sh1B),"*J. Bacteriol.,* 172:1206–1216, 1990.

von Heijne, G., "Signal sequences: The limits of variation," *J. Mol. Biol.,* 184:99–105, 1985.

Welch, "Pore–forming cytolysins of Gram–negative bacteria," *Mol. Microbiol.,* 5:521–528, 1991.

Wong et al., "Identification and characterization of an iron–regulated hemopexin receptor in *Haemophilus influenzae* type b," *Infect. Immun.,* 62:48–59, 1994.

Wong et al., "Affinity, Conservation, and Surface Exposure of Hemopexin–Binding Proteins in *Haemophilus influenzae,*" *Infection and Immunity,* 63(6):2327–2333, Jun. 1995.

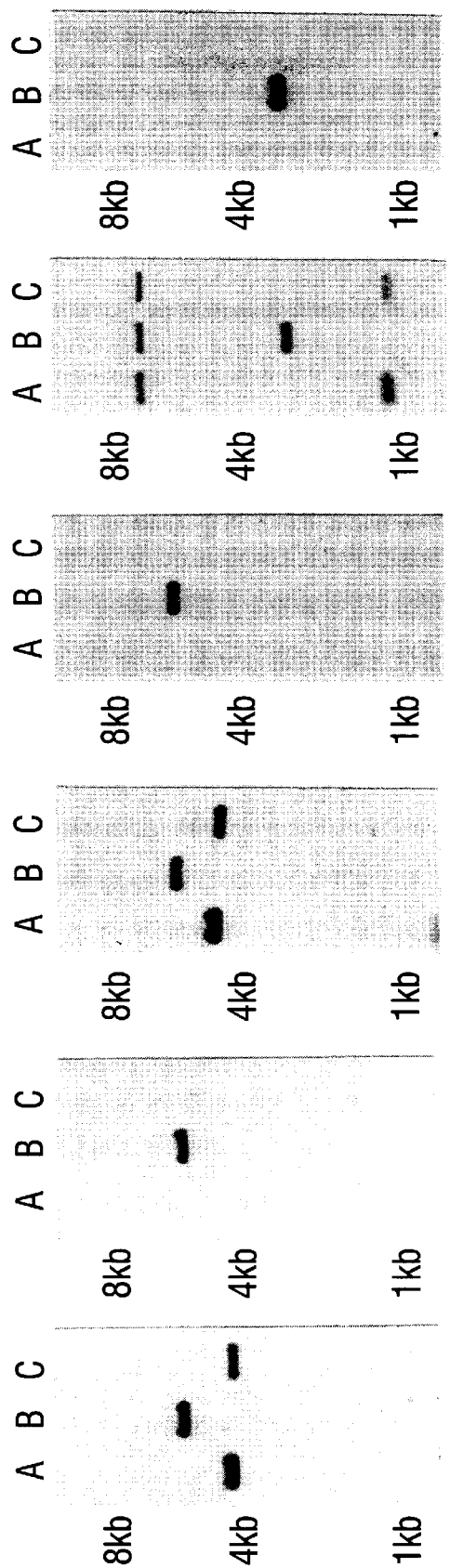

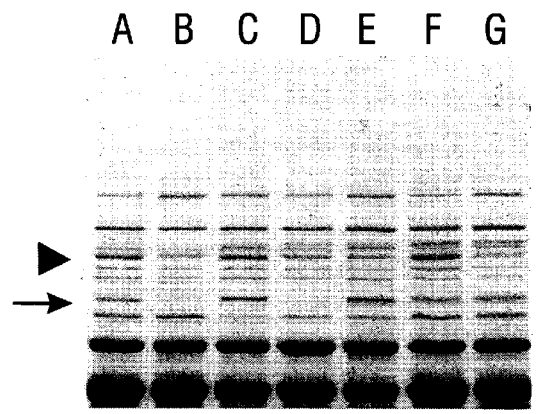
FIG. 5A
FIG. 5B
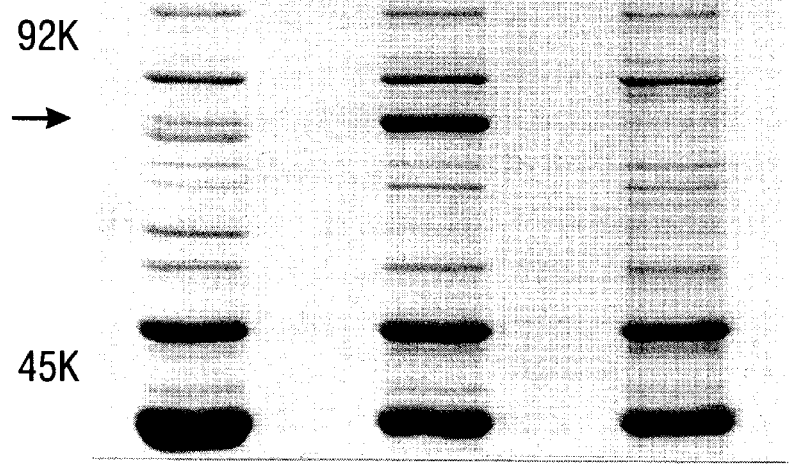
FIG. 6

H. INFLUENZAE HXUB AND HXUC GENES, PROTEINS AND METHODS OF USE

The government owns rights in the present invention pursuant to U.S. Public Health Service Grants AI17621 and DK30203.

BACKGROUND OF THE INVENTION

1. Field of the Invention

The present invention relates to the fields of DNA segments and proteins derived from bacterial species. More particularly, the invention provides *Haemophilus influenzae* hxuB and hxuC gene compositions and HxuB and HxuC proteins and peptides. Various methods for making and using hxuB and hxuC DNA segments and proteins are disclosed, such as, for example, the use of DNA segments as diagnostic probes and templates for protein production, and the use of DNA, proteins, peptides and antibodies in various pharmacological and immunological applications.

2. Description of the Related Art

*Haemophilus influenzae* type b (*Hi*b) used to be the most frequent cause of neonatal meningitis and other invasive infections of infants and young children in the United States (Fraser et al., 1974). Children of the susceptible age range, 6 months to 4 years, generally lack antibodies to the *Hi*b capsular polysaccharide, which is a target for antibodies protective against systemic *Hi*b disease. Moreover, children under the age of 2 years sometimes respond poorly to currently available polysaccharide-based vaccines such as pneumococcal vaccine or the *Hi*b vaccine. For this reason, some vaccines containing only capsular polysaccharides are of limited utility in the case of young children, the group most at risk for severe *Hi*b infections.

Although children are sometimes poor responders to vaccines containing only capsular polysaccharides, it has been reported that children in this age group respond to protein-based immunogens (Tiller and Buckley, 1978). An efficacious vaccine against *Hi*b was recently developed by conjugating the capsular polysaccharide from *Hi*b to a toxoid protein and is currently being sold under the trademark *Hi*bTITER™ (Lederle-Praxis Biologicals). However, this vaccine is not effective against disease caused by non-typeable *Haemophilus influenzae* (NT*HI*).

NT*HI* strains are known to be agents of diseases such as pneumonia, bacteremia, meningitis and postpartum sepsis (Murphy et al., 1985). In particular, NT*HI* is a frequent etiological agent of otitis media in children and young adults, causing 20–40% of all otitis media cases. Children may experience multiple infections due to the same organism as infection generally confers no long-lasting immunity. Current therapy for chronic or repeated occurrences of otitis media includes the administration of antibiotics and the insertion of tubes to drain the inner ear. Unfortunately, at the present time, no effective vaccine is available for the treatment of these infections.

In attempts to develop vaccines that are effective against NT*HI*, researchers have examined the immunogenicity of other, non-capsular *Hi*b antigens. For example, it has been reported that passive immunization with antibodies directed against non-capsular *Hi*b antigens served to protect against experimental *Hi*b bacteremia (Shenep et al., 1983). A number of *Hi*b protein components have been studied as possible candidates for the production of passive or active immunoreagents. Proteins that are present at the outer membrane are more likely to be exposed, or available for antibody binding, than are more internally localized proteins. Antibodies directed against *Hi*b outer membrane proteins have been reported to confer protection against bacteremia following intraperitoneal challenge with *Hi*b, whereas antibodies against lipopolysaccharide components lacked protective activity (Shenep et al., 1983). However, some *Hi*b proteins have proven to be either insufficiently antigenic, or their corresponding antibody non-protective (Granoff et al., 1986).

Certain envelope components that could be investigated as potential vaccines include the components of the macromolecular structures that interact with heme and hence allow heme uptake by *H. influenzae*. Elements proposed to be involved in this system to date include a periplasmic lipoprotein that binds heme and has structural similarity to an *Escherichia coli* dipeptide permease (Hanson and Hansen, 1991; Hanson et al., 1992) and a 39 kDa heme-binding protein reported to be present on the *H. influenzae* cell surface (Lee, 1992).

It is clear that while a variety of approaches to the treatment of bacterial diseases have experienced some success, the growing problems of antibiotic resistance, variability of antigens between species and in the same species through mutation of antigens, and the inefficient immune systems in young children and others, all present difficulties that need to be overcome. Thus, there exists today an immediate need for an effective treatment for all *H. influenzae* pathogens that can be used for a variety of infections and in all patients.

SUMMARY OF THE INVENTION

The present invention seeks to overcome these and other drawbacks inherent in the prior art by providing novel *H. influenzae* genes and surface exposed proteins that, in addition to various diagnostic embodiments, may also be used as a means for developing vaccines and immunological agents directed against *H. influenzae*. The nucleic acids, proteins and peptides of the invention will be particularly useful in detecting *H. influenzae* type b (*Hi*b) non-typeable *H. influenzae* (NT*HI*), and in treating disease conditions caused by these pathogens.

This invention concerns *H. influenzae* hxuB and hxuC genes and nucleic acid segments, HxuB and HxuC proteins, fusion proteins, peptides and related compositions, and methods of making and using such genes and proteins, for example in various diagnostic and treatment embodiments. Also provided are nucleic probes and primers, recombinant host cells, protein and peptide antigens and carriers, vaccines for both active and passive immunization, polyclonal and monoclonal antibodies, DNA and cellular-based vaccines, and methods for diagnosing, treating and preventing bacterial infections including, for example, meningitis and diseases particularly caused by NT*HI* and *Hi*b.

1. Nucleic Acid Segments and Vectors

The present invention provides DNA segments that comprise an isolated hxuC or hxuB gene, as exemplified by the hxuC and hxuB genes isolatable from *H. influenzae* type b (*Hi*b) and nontypeable *H. influenzae* (NT*HI*). The hxuC and hxuB genes may either be provided separately, or in the form of a continuous DNA segment that contains, or is engineered to contain, coding segments for both HxuB and HxuC proteins or peptides.

As used herein, the term "DNA segment" refers to a DNA molecule that has been isolated free of total genomic DNA of a particular species. Therefore, a DNA segment encoding an isolated hxuC and/or hxuB gene refers to a DNA segment that contains HxuB and/or HxuC protein coding sequences yet is isolated away from, or purified free from, total genomic DNA of *H. influenzae*, such as *H. influenzae* type b (*Hi*b) or nontypeable *H. influenzae* (NT*HI*). Included within the term "DNA segment", are DNA segments and smaller fragments of such segments, and also recombinant vectors, including, for example, plasmids, cosmids, phage, viruses, and the like.

Similarly, a DNA segment comprising an isolated or purified hxuC and/or hxuB gene refers to a DNA segment including HxuB and/or HxuC protein coding and, in certain aspects, regulatory sequences, isolated substantially away from other naturally occurring genes or protein encoding sequences. In this respect, the term "gene" is used for simplicity to refer to a functional protein, polypeptide or peptide encoding unit, with or without regulatory DNA sequences. As will be understood by those in the art, this functional term includes both genomic sequences, cDNA sequences and smaller engineered gene segments that express, or may be adapted to express, proteins, polypeptides or peptides.

"Isolated substantially away from other coding sequences" means that the gene of interest, in this case a hxuC and/or hxuB gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions, including coding regions encoding other epitopic sequences, later added to the segment by the hand of man.

In particular embodiments, the invention concerns isolated DNA segments and recombinant vectors incorporating DNA sequences that encode a HxuC and/or HxuB protein or peptide that has an amino acid sequence as set forth by a contiguous sequence selected from those disclosed herein. Particular examples include DNA segments encoding HxuC proteins or peptides, isolatable from *Hi*b or NT*HI*, that include an amino acid sequence as set forth by a contiguous sequence from SEQ ID NO:2 (*Hi*b) or SEQ ID NO:7 (NT*HI*). The proteins encoded may be full length proteins, as represented by the 725 amino acids of the HxuC protein from *Hi*b; or the 715 amino acids of the HxuC protein from NT*HI*.

Further examples are DNA segments encoding HxuB proteins or peptides, isolatable from *Hi*b or NT*HI*, that include an amino acid sequence as set forth by a contiguous sequence from SEQ ID NO:3 (*Hi*b) or SEQ ID NO:8 (NT*HI*). The proteins encoded may again be full length proteins, as represented by the 565 amino acids of the HxuB protein from *Hi*b; or the 564 amino acids of the HxuB protein from NT*HI*.

Any of the DNA segments, whether isolated from *Hi*b or NT*HI*, and whether encoding HxuC or HxuB proteinaceous compositions, may encode peptides of from about 15 to about 50, or more preferably, from about 20 to about 30 amino acids in length. Peptides may, of course, be of any length in this range, such as 16, 17, 18, 19 or 20 amino acids, or about 25, about 30, about 35, about 40, about 45 or about 50 amino acids in length, with "about", in this one context meaning a range of from 1 to 4 amino acids longer or shorter than the stated length. Accordingly, the DNA segments encoding such peptides will have coding lengths, excluding any regulatory sequences, of between about 45 to about 150, or preferably, of 60 to about 90, base pairs, with any length within or around these general guidelines being contemplated.

The term "a contiguous amino acid sequence from SEQ ID NO:2, 3, 7 or 8" means that the sequence substantially corresponds to a contiguous portion of SEQ ID NO:2, 3, 7 or 8 and has relatively few amino acids that are not identical to, or a biologically functional equivalent of, the amino acids of SEQ ID NO:2, 3, 7 or 8. The term "biologically functional equivalent" is well understood in the art and is further defined in detail later herein. Accordingly, sequences that have between about 70% and about 80%; or more preferably, between about 81% and about 90%; or even more preferably, between about 91% and about 99%; of amino acids that are identical or functionally equivalent to the amino acids of SEQ ID NO:2, 3, 7 or 8 will be sequences that are "as set forth in SEQ ID NO:2, 3, 7 or 8".

Biologically equivalent proteins and peptides will generally also have one or more additional functional or structural properties in common with the HxuC or HxuB proteins and peptides that have sequences from SEQ ID NO:2, 3, 7 or 8. The term "biologically functional equivalent" therefore intends that the protein or peptide have some HxuB- or HxuC-restricted sequences and/or properties, rather than exhibiting only a limited sequence element or general property in common with several bacterial proteins. A preferred test for equivalents is those proteins and peptides that are recognized by, or bind to, antibodies that bind to HxuC or HxuB proteins or peptides with sequences from SEQ ID NO:2, 3, 7 or 8. Means for determining this are readily available in the art and are further described in detail herein.

In certain other embodiments, the invention concerns isolated DNA segments and recombinant vectors, such as plasmids, that include within their sequence a nucleic acid sequence as set forth by a contiguous sequence from the sequences SEQ ID NO:1 or SEQ ID NO:6 and, preferably, as set forth by a contiguous sequence from coding regions of SEQ ID NO:1 or SEQ ID NO:6. The term "a contiguous nucleic acid sequence from SEQ ID NO:1 or SEQ ID NO:6" is used in the same sense as described above and means that the nucleic acid sequence substantially corresponds to a contiguous portion of SEQ ID NO:1 or 6 and has relatively few codons that are not identical to, or functionally equivalent with, the codons of SEQ ID NO:1 or 6. The term "functionally equivalent codon" is used herein to refer to codons that encode the same amino acid, such as the six codons for arginine or serine, and also refers to codons that encode biologically equivalent amino acids. Although such information is generally known to those of skill in the art, Table 1 is provided herein to clearly set forth this information.

It will also be understood that amino acid and nucleic acid sequences may include additional residues, such as additional N- or C-terminal amino acids, or 5' or 3' nucleic acid sequences, and yet still be as set forth in one of the sequences disclosed herein, so long as the sequence meets the criteria set forth above, including the production of a HxuB and/or HxuC protein, where protein expression is concerned. Additional amino acid sequences particularly include epitopes from other bacterial proteins, allowing the resulting fusion protein to be used as a carrier to generate useful, and even protective, immune responses.

The additional nucleic acid sequences may, for example, include various coding or non-coding sequences flanking either of the 5' or 3' portions of the coding region or various internal sequences, i.e., introns, which are known to occur within genes. The addition of 5' nucleic acid sequences that constitute regulatory regions, such as promoters and/or enhancers, is particularly contemplated by the inventors and the addition of any such sequence to any of those coding regions described above thus falls within the scope of the present invention.

Excepting intronic or flanking regions and further sequences added by the hand of man, and allowing for the degeneracy of the genetic code, sequences that have between about 70% and about 80%; or more preferably, between about 80% and about 90%; or even more preferably, between about 90% and about 99% of nucleotides that are identical to the nucleotides of SEQ ID NO:1 or 6 will be sequences that are "as set forth in SEQ ID NO:1 or 6". Sequences that as set forth in SEQ ID NO:1 or 6 may also be functionally defined as sequences that are capable of hybridizing to a nucleic acid segment containing the complement of SEQ ID NO:1 or 6 under relatively stringent conditions. Suitable relatively stringent hybridization conditions will be well known to those of skill in the art and are further described herein.

Naturally, the present invention also encompasses DNA segments that are complementary, or essentially complementary, to the sequence set forth in SEQ ID NO:1 or 6, or contiguous stretches thereof. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 or 6 under relatively stringent conditions.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length being limited only by the desired ease of preparation and use in the intended recombinant DNA protocol. For example, nucleic acid segments may be prepared that comprise a sequence region that consists of contiguous sequences that are identical to, or complementary to, sequences from SEQ ID NO:1 or SEQ ID NO:6, such as about 20 nucleotides, and which are up to about 10,000, about 5,000, about 3,000 or about 2,000 base pairs in length. DNA segments and vectors with total lengths of about 1,000, about 500, about 200, about 100 and about 50 base pairs, or any intermediate lengths between these ranges, are also contemplated to be useful.

It will be readily understood that "intermediate lengths", in this context, means any length between the quoted ranges, such as 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002 and the like.

DNA segments of the invention may include within their sequence a nucleic acid sequence that is as set forth in any contiguous stretch of the sequences of SEQ ID NO:1 or SEQ ID NO:6. However, in certain embodiments, it is contemplated that stretches from the coding regions will be preferred. As such, the invention provides protein and peptide-encoding segments of DNA that may be taken from any contiguous stretch of the coding sequences, such as from position 112 to position 2286 of SEQ ID NO:1, for Hib HxuC peptides and proteins; from position 727 to position 2871 of SEQ ID NO:6 for NTHI HxuC peptides and proteins; from position 2364 to position 4058 of SEQ ID NO:1, for Hib HxuB peptides and proteins; and from position 2957 to position 4648 of SEQ ID NO:6 for NTHI HxuB peptides and proteins.

In certain cases, for example, where the expression of the full length HxuC and/or HxuB proteins is desired, one will likely wish to use DNA segments that include the entire coding sequence of the respective gene or genes. Therefore, DNA segments that comprise Hib genes having the sequences represented by the sequence from position 112 to position 2286 of SEQ ID NO:1, expressing HxuC; or from position 2364 to position 4058 of SEQ ID NO:1, expressing HxuB; or indeed, including the whole of SEQ ID NO:1, expressing HxuC and HxuB proteins, will be preferred. Likewise, DNA segments comprising NTHI genes having the sequences represented by the sequence from position 727 to position 2871 of SEQ ID NO:6, expressing HxuC; or from position 2957 to position 4648 of SEQ ID NO:6, expressing HxuB; or including the whole of SEQ ID NO:6, expressing HxuC and HxuB proteins, will also be preferred.

In embodiments concerning vaccination, or the production of other therapeutic immunoreagents, sequences from NTHI are currently preferred because NTHI currently represents the more severe clinical problem. However, in that new methods to detect Hib or NTHI, or to treat any disease caused by either of these species are needed, it is evident that all the compositions disclosed herein have significant utility.

As this invention is not limited solely to the particular nucleic acid and amino acid sequences disclosed herein, recombinant vectors and DNA segments in accordance with the invention may variously include the HxuB and/or HxuC protein coding regions themselves, coding regions bearing selected alterations or modifications in the basic coding region or biologically functional equivalent proteins or peptides that have variant amino acids sequences. Such biologically functional equivalent HxuB and/or HxuC proteins and peptides may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test Hxu protein mutants in order to examine their activity at the molecular level. All such variants, whether produced by nature or man, are within the scope of the present invention.

It will also be understood that the length and content of the nucleic acid and amino acid sequences disclosed herein is virtually unlimited, so long as the sequences are isolated free from their natural environment and contain HxuB and/or HxuC protein or DNA sequences. Recombinant vectors and DNA segments may therefore include HxuB and/or HxuC protein encoding regions in combination with other functional sequences. For example, this may be employed to prepare fusion proteins and peptides where the HxuB and/or HxuC protein coding regions are aligned within the same expression unit with other proteins or peptides having desired functions. For example, HxuB and/or HxuC proteins may be tagged with other sequences to allow for subsequent localization or immunodetection; linked to other units, including metal binding sequences, to improve purification, e.g., by affinity chromatography; and particularly, linked to other epitopes for use as a carrier in immunization.

Recombinant vectors form an important aspect of the present invention. Particularly useful recombinant vectors are thus contemplated to be those vectors in which the coding portion of the DNA segment (also herein termed "the sequence region"), whether encoding a full length protein or variant thereof, or a smaller peptide, is positioned under the control of a promoter, wherein the term "promoter" also includes promoter/enhancer units. The promoter may be in the form of the promoter that is naturally associated with HxuB and/or HxuC proteins in *H. influenzae* cells, as may be obtained by isolating the 5' non-coding sequences located upstream of the coding segment or exon, for example, using recombinant cloning and/or PCR technology, as described in U.S. Pat. No. 4,683,202, incorporated herein by reference.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a HxuB and/or HxuC gene in its natural environment. Such promoters may include *H. influenzae* promoters normally associated with other genes, and/or promoters isolated from any other bacterial, eukaryotic, or mammalian cell.

Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al. (1989). The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the T7 RNA polymerase promoter system described by Tabor and Richardson (1985) and the maltose binding protein-fusion protein system (Guan et al., 1987; Nagai and Thogersen, 1987).

It is contemplated that nucleic acid segments of the present invention will have numerous uses, for example, in connection with the expression of peptides or proteins, such as antigens, in DNA and cell-based vaccination, and also as probes and primers. Probes and primers based upon, or designed from, SEQ ID NO:1 and SEQ ID NO:6, will have use in various hybridization embodiments, regardless of whether they encode proteins or peptides or whether they are derived from non-coding segments. Nucleic acid segments that incorporate at least a 20 contiguous nucleotide long stretch that corresponds to a contiguous sequence within SEQ ID NO:1 or 6 may be employed as selective hybridization probes.

The hybridization probes of the invention may be characterized as nucleic acid segments that comprise a sequence region that consists of at least 20 contiguous nucleotides that have the same sequence as, or are complementary to, 20 contiguous nucleotides of SEQ ID NO:1 or SEQ ID NO:6; or that are from 20 to about 10,000 nucleotides in length and that hybridizes to the nucleic acid segment of SEQ ID NO:1 or SEQ ID NO:6, or the complement thereof, under standard hybridization conditions.

Such probes may be used for the detection of *H. influenzae* sequences in selected samples or to screen clone banks to identify clones that comprise corresponding or related sequences. The detection of *H. influenzae* sequences in samples, particularly in clinical samples, represents an important utility of the present invention as detection of *H. influenzae* is important in and of itself, and also as diagnosis of an *H. influenzae* infection represents the first element in designing an appropriate treatment regimen for a given disease or disorder.

This invention thus also provides molecular biological methods for detecting *H. influenzae* in a suspected infected sample, including a clinical sample, as may be employed in the diagnosis of bacterial infections and diseases, such as meningitis and otitis media caused by *Hi*b and, more particularly, by NT*HI*. Other diseases that may be diagnosed include pneumonia, bacteremia and postpartum sepsis. Samples that may be analyzed include those such as an ear swab, sputum sample, bronchoalveolar fluid, middle ear fluid sample or a blood, serum or even a urine sample.

To conduct such a diagnostic method, one would generally obtain sample nucleic acids from the sample and contact the nucleic acids with a nucleic acid segment that encodes a HxuC or HxuB protein or peptide, under conditions effective to allow hybridization of substantially complementary nucleic acids, and then detect the presence of any hybridized substantially complementary nucleic acid complexes that formed. The presence of a substantially complementary nucleic acid sequence in a sample, or a significantly increased level of such a sequence in comparison to the levels in a normal or "control" sample, will thus be indicative of a sample that harbors *H. influenzae*. Where a substantially complementary nucleic acid sequence, or a significantly increased level thereof, is detected in a clinical sample from a patient suspected of having an infection, this will be indicative of a patient that has a *H. influenzae* infection. As used herein, the term "increased levels" is used to describe a significant increase in the amount of the hxuB or hxuC nucleic acids detected in a given sample in comparison to that observed in a control sample, e.g., an equivalent sample from a normal healthy subject.

A variety of hybridization techniques and systems are known that can be used in connection with the *H. influenzae* detection aspects of the invention, including diagnostic assays such as those described in Falkow et al., U.S. Pat. No. 4,358,535. Short coding or non-coding nucleic acid segment probes may also be employed as primers in connection with diagnostic PCR technology, as well as for use in any of a number of other PCR applications, including PCR-based cloning and engineering protocols (U.S. Pat. No. 4,683,202).

In general, the "detection" of a hxuC or hxuB sequence is accomplished by attaching or incorporating a detectable label into the nucleic acid segment used as a probe and "contacting" a sample with the labeled probe. In such processes, an effective amount of a nucleic acid segment that comprises a detectable label (a probe), is brought into direct juxtaposition with a composition containing target nucleic acids. Hybridized nucleic acid complexes may then be identified by detecting the presence of the label, for example, by detecting a radio, enzymatic, fluorescent, or even chemiluminescent label.

Many suitable techniques for use in the detection of hxuC and/or hxuB nucleic acids will be known to those of skill in the art, these include, for example, in situ hybridization, Southern blotting and Northern blotting. In situ hybridization describes the techniques wherein the target nucleic acids contacted with the probe sequences are those located within one or more cells, such as cells within a clinical sample or even cells grown in tissue culture. As is well known in the art, the cells are prepared for hybridization by fixation, e.g. chemical fixation, and placed in conditions that allow for the hybridization of a detectable probe with nucleic acids located within the fixed cell.

Alternatively, target nucleic acids may be separated from a cell or clinical sample prior to contact with a probe. Any of the wide variety of methods for isolating target nucleic acids may be employed, such as cesium chloride gradient centrifugation, chromatography (e.g., ion, affinity, magnetic), phenol extraction and the like. Most often, the isolated nucleic acids will be separated, e.g., by size, using electrophoretic separation, followed by immobilization onto a solid matrix, prior to contact with the labelled probe. These prior separation techniques are frequently employed in the art and are generally encompassed by the terms "Southern blotting" and "Northern blotting". Although the execution of various techniques using labeled probes to detect H. influenzae DNA or RNA sequences in clinical samples are well known to those of skill in the art, these methods are further described in detail herein.

To detect an hxuC or hxuB sequence, particularly in a clinical sample, one may use PCR, as disclosed in U.S. Pat. No. 4,683,202. PCR detection still comprises the steps of obtaining sample nucleic acids and contacting them with isolated hxuC or hxuB nucleic acid segments under conditions effective to allow hybridization of substantially complementary nucleic acids, and detecting nucleic acid products formed following the hybridization step. However, here the product to be detected is not a direct counterpart to the hybridizing sequences, but an amplified product, the production of which is made possible following the initial hybridization.

To conduct PCR detection in accordance with the present invention, one would therefore obtain sample nucleic acids suspected of containing an hxuC or hxuB nucleic acid, and contact the sample nucleic acids with a pair of nucleic acid primers that hybridize to spatially distant sequences from an hxuC or hxuB nucleic acid sequence. The primers are chosen such that, after hybridizing, they are capable of priming the amplification of an hxuC or hxuB nucleic acid segment when used in conjunction with a polymerase chain reaction, i.e., with a thermostable polymerase enzyme. The polymerase chain reaction is conducted for a number of appropriate cycles, as is known to one of ordinary skill in the art, and the amplification products are formed. The amplification products may be detected simply by their presence on a gel, which detection may be supplemented by sizing and/or further sequence-specific hybridization.

Nucleic acid molecules that comprise a sequence region that consists of a contiguous sequence of about 20, about 30, about 40, about 50, about 100–200, or even of about 1000–2000–3000 or so nucleotides in length, which sequence corresponds to, or is complementary to, a contiguous sequence of SEQ ID NO:1 or SEQ ID NO:6 will have utility as a hybridization probe or primer. These probes will be useful in a variety of hybridization embodiments, which also include Southern and Northern blotting in connection with analyzing hxuB and/or hxuC genes in diverse bacteria and in various H. influenzae strains. The total size of fragment, as well as the size of the complementary stretch (es), will ultimately depend on the intended use or application of the particular nucleic acid segment. Fragments generally finding use in hybridization embodiments may have lengths of contiguous complementary regions that vary between about 20 and about 100 nucleotides. However, longer sequences of 500–1000, 2000, 3000 or even up to the full length sequences of 4061 (SEQ ID NO:1 ) and 4651 (SEQ ID NO:6) may be used, according to the complementary sequences one wishes to detect.

Once the entire coding sequence of an hxuB and/or hxuC gene has been determined, various primers can be easily designed and made. For example, by assigning numeric values to a sequence, for example, the first residue is 1, the second residue is 2, etc., an algorithm defining all primers can be proposed:

$n$ to $n+y$ where n is an integer from 1 to the last number of the sequence and y is the length of the primer minus one (e.g., 19, 24, 29 or such like), where n+y does not exceed the last number of the sequence. For example, for SEQ ID NO:1, n is 1 to 4061; and for SEQ ID NO:6, n is 1 to 4651. Thus, for a 20-mer from SEQ ID NO:1, the probes correspond to bases 1 to 20, 2 to 21, 3 to 22 . . . and 4052 to 4061. For a 30-mer, the probes correspond to bases 1 to 30, 2 to 31, 3 to 32 . . . and 4042 to 4061. For a 20-mer from SEQ ID NO:6, the probes correspond to bases 1 to 20, 2 to 21, 3 to 22 . . . and 4632 to 4651; and for a 30-mer, the probes correspond to bases 1 to 30, 2 to 31, 3 to 32 . . . and 4632 to 4651.

Therefore, in light of the sequences and teachings of the present disclosure, those of ordinary skill in the art will be able to design and make any hxuB or hxuC probe or primer. Making the smaller probes and primers will most simply be achieved by automated oligonucleotide synthesis, as is commonly practiced in the art. Although other methods, e.g., PCR generation, restriction enzyme digestion, and various sub-cloning techniques are also available and could be employed in the generation of short, intermediate or longer probes, primers and nucleic acid fragments.

In terms of the lengths of DNA segments, these may, of course, be of any length in the stated ranges, such as 20, 21, 22, 23 or 24 nucleotides in length. This is the meaning of "about" in about 20, about 25, about 30, about 35, about 40, about 45 or about 50 nucleotides in length, with "about", in this one context meaning a range of from 1 to 4 nucleotides longer or shorter than the stated length, with 15 or 20 or so still being the minimum length.

The present invention also provides nucleic acid detection kits that comprise, in suitable container means, at least one isolated hxuC or hxuB nucleic acid segment and a detection reagent. The kits may further include one or more unrelated nucleic acid segments, for use as controls, restriction enzymes, and components or enzymes for use in PCR. Preferably, the isolated hxuC or hxuB nucleic acid segments will be between about 50 and about 500 nucleotides in length and, in certain embodiments, the detection reagent will be a label linked to the hxuC or hxuB nucleic acid segment. The components of the kits will preferably be packaged within distinct containers.

2. Recombinant Host Cells

The present invention also concerns recombinant host cells and viruses that include one or more DNA segments that comprise an isolated hxuC or hxuB gene, as described herein. It is contemplated that virtually any cell may be employed as a recombinant host cell, but that certain advantages may be found in using a bacterial host cell, such as, for example, in the ease of cell growth and manipulation. Examples of preferred bacteria for use as recombinant host cells include, for example, Salmonella, E. coli, H. influenzae type b (Hib), and non typeable H. influenzae (NTHI), with E. coli and non typeable H. influenzae (NTHI) being particularly preferred, and with H. influenzae Rd strain DB117 being particularly preferred. However, expression in eukaryotic cells is also contemplated, and exemplary cell lines that may be used include all those typically employed for eukaryotic expression, such as 239, AtT-20, HepG2, VERO, HeLa, CHO, WI 38, BHK, COS-7, RIN and MDCK cell lines.

The recombinant host cells of the invention may be employed to propagate the vector, to immunize an animal and/or to express the various peptides and proteins described herein, allowing the encoded components to be obtained essentially free of other *H. influenzae* components. That is, one may prepare such peptides or proteins by recombinant expression using a host cell other than *H. influenzae;* and/or produce the peptides or proteins at high levels so that their isolation directly results in a significantly enriched preparation. Preferred recombinant host cells are those capable of expressing peptides and proteins with sequences as set forth in SEQ ID NOS:2, 3, 7 or 8, and more particularly, those capable of expressing NT*HI* HxuC and/or HxuB proteins or peptides, such as those with amino acid sequences as set forth in SEQ ID NOS:7 or 8.

Depending on the host system employed, one may find particular advantages where DNA segments of the present invention are incorporated into appropriate vector sequences that may, e.g., improve the efficiency of transfection of host cells. Where bacterial host cells are employed, it is proposed that virtually any vector known in the art to be appropriate for the selected host cell may be employed. Thus, in the case of *E. coli,* one may find particular advantages through the use of plasmid vectors such as pBR322, or bacteriophages such as λGEM-11. Further examples will be known to those of skill in the art, as exemplified in Sambrook et al. (1989).

The recombinant host cells may be employed in connection with "overexpressing" HxuB and/or HxuC proteins or peptides, that is, increasing expression over the natural expression levels in *H. influenzae* cells, as may lead to the production of large quantities of proteins. Overexpression may be assessed by a variety of methods, including radio-labelling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide, in comparison to the level in natural *H. influenzae* cells, is indicative of overexpression.

In further related embodiments, the invention concerns processes for preparing compositions that include purified proteins or peptides with sequences as set forth in SEQ ID NOS:2, 3, 7 or 8, and most preferably, proteins or peptides with sequences in accordance with SEQ ID NOS:7 or 8. In a general sense, these processes include first selecting cells that are capable of expressing such proteins or peptides, culturing the cells under conditions effective to allow expression of the proteins or peptides, and collecting the proteins or peptides to thereby prepare the composition.

Where one desires to prepare HxuB and/or HxuC proteins or peptides, one may simply culture naturally available cells, such as *H. influenzae* H*i*b or NT*HI* cells, when the proteins will be expressed and obtainable, e.g., from the outer membrane fraction of the cell. In preferred embodiments, it is contemplated that one would use a DNA segment that included an isolated hxuC or hxuB gene to express the recombinant protein. To achieve this, one would generally first obtain or prepare a recombinant vector in which an HxuC-encoding or HxuB-encoding DNA segment is positioned under the control of a promoter and then introduce the vector into a cell to form a recombinant host cell. One would then allow the cell to grow (known as "culturing") under conditions effective to allow the expression of an encoded HxuC or HxuB protein or peptide, which protein or peptide could then be collected.

Various methods may be used to obtain or collect HxuB and/or HxuC proteins or peptides from cells, whether native or recombinant. For example, one method involves preparing membrane fractions, which may then be solubilized and extracted to provide the protein, e.g., using an ionic or non-ionic detergent. Further purification may be achieved by a variety of methods including column fractionation, isoelectric focusing, and the like, or even immunoadsorption employing HxuB and/or HxuC-directed antibodies. In any of the above ways, HxuB and/or HxuC proteins or peptides can be provided essentially free from non-HxuB and HxuC components.

3. Proteins, Peptides, Antigens, Antibodies and Kits

The present invention further provides protein or peptide compositions, free from total bacterial cells, comprising a purified HxuC and/or HxuB protein or peptide that includes an amino acid sequence as set forth by a contiguous sequence from SEQ ID NO:2, SEQ ID NO:3, SEQ ID NO:7 or SEQ ID NO:8. Such compositions may be obtained from natural or recombinant sources and may include proteins or peptides, proteins and peptides, HxuB compositions alone, HxuC compositions alone or HxuB and HxuC compositions, obtainable from either H*i*b or NT*HI*. The compositions may include one or more full length HxuB or HxuC proteins, preferably those isolatable from NT*HI,* and/or various peptides that include sequences in accordance with a 15 to about 50, or more preferably, a 20 to about 30 amino acid long sequence from SEQ ID NO:2, 3, 7 or 8, with SEQ ID NOS:7 and 8 being preferred.

As the HxuB and HxuC proteins are expressed at the cell surface, certain embodiments of the invention concern the use of the such proteins and peptides in immunological based therapies for the prevention or treatment of bacterial infections and diseases. Therefore, the invention also encompasses HxuB and/or HxuC antigen compositions together with pharmaceutically acceptable carriers, diluents, adjuvants, and other components, such as additional antigens or outer membrane preparations, as may be employed in the formulation of vaccines.

The present invention thus also provides methods of generating an immune response, which methods generally comprise administering to an animal, including a human subject, a pharmaceutically acceptable composition comprising an immunologically effective amount of a HxuB and/or HxuC protein or peptide composition. The composition may include partially or significantly purified HxuC and/or HxuB proteins or peptides, obtained from natural or recombinant sources, which proteins or peptides may be obtainable from either H*i*b or NT*HI*. Smaller peptides that include reactive epitopes, such as those between about 30 and about 50 amino acids in length will often be preferred. The HxuB and/or HxuC proteins or peptides may also be combined with other agents, such as other *H. influenzae* OMP compositions, if desired.

By "immunologically effective amount" is meant an amount of a HxuB and/or HxuC protein or peptide composition that is capable of generating an immune response in the recipient animal. This includes both the generation of an antibody response (B cell response), and/or the stimulation of a cytotoxic immune response (T cell response). The generation of such an immune response will have utility in both the production of useful bioreagents, e.g., CTLs and, more particularly, reactive antibodies, for use in diagnostic embodiments, and will also have utility in various prophylactic or therapeutic embodiments. Therefore, although these methods for the stimulation of an immune response include vaccination regimens designed to prevent or lessen significant *H. influenzae* infections, and treatment regimens that may lessen the severity or duration of any infection, it will be understood that achieving either of these end results is not necessary for practicing these aspects of the invention.

Further means contemplated by the inventors for generating an immune response in an animal includes administering to the animal, or human subject, a pharmaceutically acceptable composition comprising an immunologically effective amount of a hxuC and/or hxuB nucleic acid composition, or an immunologically effective amount of an attenuated live organism that includes and expresses an hxuC and/or hxuB nucleic acid composition. The "immunologically effective amounts" are those amounts capable of stimulating a B cell and/or T cell response.

The stimulation of specific antibodies and CTL (cytotoxic T lymphocyte) responses upon administering to an animal a nucleic molecule is now well known in the art, as evidenced by articles such as Tang et al. (1992); Cox et al. (1993;) Fynan et al. (1993); Ulmer et al. (1993); Wang et al. (1993) and Whitton et al. (1993); each incorporated herein by reference. The use of attenuated organisms, such as vaccinia viruses and salmonella, that express recombinant DNA products is also now established in the art and contemplated for use in the present invention.

The naked DNA technology, often referred to as genetic immunization, is contemplated to be suitable to protect against infectious organisms. Immunization with DNA has been successfully employed to protect animals from challenge with influenza A (Ulmer et al., 1993). The use of the hxuC and/or hxuB nucleic acid compositions of the present invention in techniques such as those described by Ulmer et al. (1993; incorporated herein by reference), is thus proposed to be useful as a vaccination regimen. The hxuC and/or hxuB DNA segments could be used in virtually any form, including naked DNA and plasmid DNA, and may be administered to the animal in a variety of ways, including parenteral, mucosal and gene-gun inoculations, as described, for example, by Fynan et al. (1993).

Immunoformulations of this invention, whether intended for vaccination, treatment, or for the generation of antibodies useful in *H. influenzae* detection, may comprise whole HxuB and/or HxuC proteins or antigenic peptide fragments from these proteins. As such, antigenic functional equivalents of the proteins and peptides described herein also fall within the scope of the present invention. An "antigenically functional equivalent" protein or peptide is one that incorporates an epitope that is immunologically cross-reactive with one or more epitopes of the HxuB and/or HxuC proteins. Antigenically functional equivalents, or epitopic sequences, may be first designed or predicted and then tested, or may simply be directly tested for cross-reactivity.

The identification or design of HxuB and/or HxuC epitopes, and/or their functional equivalents, suitable for use in immunoformulations, vaccines, or simply as antigens (e.g., for use in detection protocols), is a relatively straightforward matter. For example, one may employ the methods of Hopp, as enabled in U.S. Pat. No. 4,554,101, incorporated herein by reference, that teaches the identification and preparation of epitopes from amino acid sequences on the basis of hydrophilicity. The methods described in several other papers, and software programs based thereon, can also be used to identify epitopic core sequences, for example, Chou and Fasman (1974a,b; 1978a,b; 1979); Jameson and Wolf (Jameson and Wolf, 1988; Wolf et al. 1988); and Kyte and Doolittle (1982) address this subject. The amino acid sequence of these "epitopic core sequences" may then be readily incorporated into peptides, either through the application of peptide synthesis or recombinant technology.

It is proposed that the use of shorter antigenic peptides, e.g., about 15–30 or 20–30 amino acids in length, that incorporate epitopes of the selected HxuB and/or HxuC protein will provide advantages in certain circumstances, for example, in the preparation of vaccines or in immunologic detection assays. Exemplary advantages include the ease of preparation and purification, the relatively low cost and improved reproducibility of production, and advantageous biodistribution.

To confirm that a protein or peptide is immunologically cross-reactive with, or a biological functional equivalent of, one or more epitopes of the HxuB and/or HxuC proteins is also a straightforward matter. This can be readily determined using specific assays, e.g., of a single proposed epitopic sequence, or using more general screens, e.g., of a pool of randomly generated synthetic peptides or protein fragments. The screening assays may be employed to identify either equivalent antigens or cross-reactive antibodies. In any event, the principle is the same, i.e., based upon competition for binding sites between antibodies and antigens.

Suitable competition assays that may be employed include protocols based upon immunohistochemical assays, ELISAs, RIAs, Western or dot blotting and the like. In any of the competitive assays, one of the binding components, generally the known element, such as the HxuC or HxuB protein or peptide, or the known antibody, such as the monoclonal antibody 2B7 or 6D3, will be labeled with a detectable label and the test components, that generally remain unlabeled, will be tested for their ability to reduce the amount of label that is bound to the corresponding reactive antibody or antigen.

As an exemplary embodiment, to conduct a competition study between HxuB and any test antigen, one would first label HxuB with a detectable label, such as, e.g., biotin or an enzymatic, radioactive or fluorogenic label, to enable subsequent identification. One would then incubate the labelled antigen with the other, test, antigen to be examined at various ratios (e.g., 1:1, 1:10 and 1:100) and, after mixing, one would then add the mixture to a known antibody, such as 2B7 or 6D3. Preferably, the known antibody would be immobilized, e.g., by attaching to an ELISA plate. The ability of the mixture to bind to the antibody would be determined by detecting the presence of the specifically bound label. This value would then be compared to a control value in which no potentially competing (test) antigen was included in the incubation.

The assay may be any one of a range of immunological assays based upon hybridization, and the reactive antigens would be detected by means of detecting their label, e.g., using streptavidin in the case of biotinylated antigens or by using a chromogenic substrate in connection with an enzymatic label or by simply detecting a radioactive or fluorescent label. An antigen that binds to the same antibody as HxuB, for example, will be able to effectively compete for binding to 2B7 or 6D3 and thus will significantly reduce HxuB binding, as evidenced by a reduction in the amount of label detected.

The reactivity of the labeled antigen, e.g., HxuB, in the absence of any test antigen would be the control high value. The control low value would be obtained by incubating the labeled antigen with an excess of unlabeled HxuB antigen, when competition would occur and reduce binding. A significant reduction in labeled antigen reactivity in the presence of a test antigen is indicative of a test antigen that is "cross-reactive", i.e., that has binding affinity for the same antibody. "A significant reduction", in terms of the present application, may be defined as a reproducible (i.e., consistently observed) reduction in binding.

In further embodiments, the invention concerns relatively purified antibodies that bind to, or have binding affinity for, a HxuC or HxuB protein or peptide. Such relatively purified antibodies may be polyclonal or monoclonal and are distinct from those compositions that may be found in nature, e.g., as represented by the sera of an individual infected with *H. influenzae*, by virtue of their increased degree of purity. Even a polyclonal antibody raised in response to immunization with a purified, or enriched, HxuB and/or HxuC protein composition will be significantly distinct from the sera of an infected individual that contains a great diversity of antibodies.

Particular techniques for preparing antibodies in accordance with the invention are disclosed herein. However, it is proposed by the inventors that any of the current techniques known in the art for the preparation of antibodies in general may be employed, through the application of either monoclonal or polyclonal technology, and as represented by the generation of the monoclonal antibodies 2B7, that binds to HxuB, and 6D3 that binds to HxuC. Antibodies that are cross-reactive with 2B7 and 6D3 are also encompassed by the invention, as may be identified by employing a competition binding assay, such as those described above in terms of antigen competition.

Antibodies of the invention may also be linked to a detectable label, such as a radioactive, fluorescent, electrochemiluminescent or a nuclear magnetic spin resonance label. Biolabels such as avidin, biotin and enzymes that are capable of generating a colored product upon contact with a chromogenic substrate are also contemplated. Exemplary enzyme labels include alkaline phosphatase, urease, hydrogen peroxidase and glucose oxidase enzymes.

In still further embodiments, the present invention concerns immunodetection methods and associated kits. It is contemplated that the HxuB and/or HxuC proteins or peptides of the invention may be employed to detect antibodies having reactivity therewith, or, alternatively, antibodies prepared in accordance with the present invention, e.g., 2B7 or 6D3, or like antibodies, may be employed to detect HxuB or HxuC proteins or peptides, respectively. Either type of kit may be used in the immunodetection of compounds, present within clinical samples, that are indicative of *H. influenzae* infection. The kits may also be used in antigen or antibody purification, as appropriate.

In general, immunodetection methods will include first obtaining a sample suspected of containing such a protein, peptide or antibody, such as a biological sample from a patient, and contacting the sample with a first HxuC or HxuB protein or peptide, or a first antibody that binds to a HxuC or HxuB protein or peptide, as the case may be, under conditions effective to allow the formation of an immunocomplex (primary immune complex). One then detects the presence of any primary immunocomplexes that are formed.

Contacting the chosen sample with the HxuC or HxuB protein or peptide, or antibody thereto, under conditions effective to allow the formation of (primary) immune complexes is generally a matter of simply adding the protein, peptide or antibody composition to the sample. One then incubates the mixture for a period of time sufficient to allow the added antigens or antibodies to form immune complexes with, i.e., to bind to, any antibodies or antigens present within the sample. After this time, the sample composition, such as a tissue section, ELISA plate, dot blot or western blot, will generally be washed to remove any non-specifically bound antigen or antibody species, allowing only those specifically bound species within the immune complexes to be detected.

The detection of immunocomplex formation is well known in the art and may be achieved through the application of numerous approaches known to the skilled artisan and described in various publications, such as, e.g., Nakamura et al. (1987), incorporated herein by reference. Detection of primary immune complexes is generally based upon the detection of a label or marker, such as a radioactive, fluorescent, biological or enzymatic label, with enzyme tags such as alkaline phosphatase, horseradish peroxidase and glucose oxidase being suitable. The antigen (e.g., HxuB) or antibody (e.g., 2B7) employed may itself be linked to a detectable label, wherein one would then simply detect this label, thereby allowing the amount of bound antigen or antibody present in the composition to be determined.

Alternatively, the primary immune complexes may be detected by means of a second binding ligand that is linked to a detectable label and that has binding affinity for the first protein, peptide or antibody. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labelled secondary antibodies or ligands, and the remaining bound label is then detected.

For diagnostic purposes, it is proposed that virtually any sample suspected of containing either the HxuB and/or HxuC proteins, peptides or antibodies sought to be detected, as the case may be, may be employed. Exemplary samples include clinical samples obtained from a patient such as blood or serum samples, bronchoalveolar fluid, ear swabs, sputum samples, middle ear fluid or even perhaps urine samples may be employed. This allows for the diagnosis of meningitis, otitis media, pneumonia, bacteremia and postpartum sepsis. Furthermore, it is contemplated that such embodiments may have application to non-clinical samples, such as in the titering of antigen or antibody samples, in the selection of hybridomas, and the like.

In related embodiments, the present invention contemplates the preparation of kits that may be employed to detect the presence of HxuB and/or HxuC proteins, peptides and/or antibodies in a sample. Generally speaking, kits in accordance with the present invention will include a suitable HxuB and/or HxuC protein or peptide, or a first antibody that binds to a HxuC or HxuB protein or peptide, together with an immunodetection reagent, and a means for containing the protein, peptide or antibody and reagent.

The immunodetection reagent will typically comprise a label associated with the protein, peptide or antibody, or associated with a secondary binding ligand. Exemplary ligands might include a secondary antibody directed against the first protein, peptide or antibody, or a biotin or avidin (or streptavidin) ligand having an associated label. Detectable labels linked to antibodies that have binding affinity for a human antibody are also contemplated, e.g., for protocols where the first reagent is a protein that is used to bind to a reactive antibody from a human sample. Of course, as noted above, a number of exemplary labels are known in the art and all such labels may be employed in connection with the present invention. The kits may contain antigen or antibody-label conjugates either in fully conjugated form, in the form of intermediates, or as separate moieties to be conjugated by the user of the kit.

The container means will generally include at least one vial, test tube, flask, bottle, syringe or other container means, into which the antigen or antibody may be placed, and preferably suitably allocated. Where a second binding ligand is provided, the kit will also generally contain a second vial or other container into which this ligand or antibody may be placed. The kits of the present invention will also typically include a means for containing the vials in close confinement for commercial sale, such as, e.g., injection or blow-molded plastic containers into which the desired vials are retained.

BRIEF DESCRIPTION OF THE DRAWINGS

FIG. 3, Panel A Panel B, Panel C, Panel D, Panel E and Panel F. Southern blot analysis of insertion mutations in the H*i*b hxuC, hxuB, and hxuA mutants. FIG. 3 consists of Panels A–F; each of which panels have lanes A, B and C. The following description applies to all Panels A–F. Chromosomal DNA from the wild-type strain H*i*b DL42 (lanes termed A), the respective mutant with a cat cartridge inserted into the hxuC, hxuB, or hxuA genes in the bacterial chromosome (lanes termed B), and a chloramphenicol-sensitive transformant derived from each of these three mutants by transformation with linearized pHX1-60 (lanes termed C) were digested with various enzymes and then probed with either a fragment of the respective structural gene or the cat cartridge. Size markers (in kb) are present on the left side of this figure prior to Panel A, lane A, and are appropriate to all panels. Individual descriptions that apply to distinct groups of Panels follow below.

FIG. 3A and 3B: chromosomal DNA from DL42, DL42.63, and DL42.63.T digested with PstI and probed with either a 1.2 kb SpeI-HindIII fragment representing the 5'-half of hxuC (3A) or with the cat cartridge (3B).

FIG. 3C and 3D: chromosomal DNA from DL42, DL42.62, and DL42.62.T digested with PstI and probed with either a 1.4 kb AlwNI fragment containing nearly all of the hxuB gene (3C) or the cat cartridge (3D).

FIG. 3E and 3F: chromosomal DNA from DL42, DL42.61, and DL42.61.T digested with both PstI and EcoRV and probed with either a 2.2 kb PstI-PvuII fragment containing most of the hxuA gene (3E) or the cat cartridge (3F).

FIG. 4 consists of Panel A (upper) and Panel B (lower); both of which panels have lanes A, B, C and D. The following description is appropriate for both Panel A and Panel B. Proteins in culture supernatants were resolved by SDS-PAGE, transferred to nitrocellulose, and incubated with radioiodinated heme:hemopexin prior to processing for autoradiography. Lanes A, wild-type DL42; Lanes B, the hxuC mutant DL42.63; Lanes C, the hxuB mutant DL42.62; Lanes D, the hxuA mutant DL42.61.

FIG. 4, Panel A: each strain lacks the recombinant plasmid pSET200 containing the NT*HI* hxuA gene.

FIG. 4, Panel B: each strain is a recombinant containing pSET200. The arrows present on the left side of this figure, prior to Lane A, indicate the position of the HxuA protein and are appropriate to all lanes.

FIG. 5, Panel A and Panel B. Detection of HxuC and HxuB proteins in outer membrane vesicles of wild-type, mutant, and transformant H*i*b strains. FIG. 5 consists of Panel A (upper) and Panel B (lower); both of which panels have lanes A, B, C, D, E, F and G. The following description is appropriate for both Panel A and Panel B: proteins present in outer membrane vesicles were resolved by SDS-PAGE according to the following lane designations: Lanes A, wild-type strain DL42; Lanes B, the hxuC mutant DL42.63; Lanes C, the transformant DL42.63.T; Lanes D, the hxuB mutant DL42.62; Lanes E, the transformant DL42.62.T; Lanes F, the hxuA mutant DL42.61; and Lanes G, the transformant DL42.61.T.

FIG. 5, Panel A: After SDS Page, proteins were stained with Coomassie blue. Only the upper half of the gel is shown. The arrow on the left side of the figure, prior to lane A, indicates the position of the 62 kDa HxuB protein in the wild-type strain DL42. Similarly, the triangle indicates the position of the 78 kDa HxuC protein in the wild-type strain.

FIG. 5, Panel B: After SDS Page, proteins were transferred to nitrocellulose and probed in Western blot analysis with the HxuB-specific Mab 2B7. Only the region of the nitrocellulose pad containing the HxuB protein is shown.

FIG. 6. Overexpression of the HxuC protein by a recombinant H*i*b strain. FIG. 6 is a single panel consisting of lanes A, B and C. Outer membrane vesicles from the wild-type H*i*b strain DL42 (lane A), the recombinant strain DL42.63 (pHX1-64) (lane B), and the recombinant strain DL42.63 (pGJB103) (lane C) were resolved by SDS-PAGE and stained with Coomassie blue. Only the relevant top half of the separating gel shown. The arrow on the left hand side, prior to lanes A, indicates the position of the HxuC protein. Note also the absence of the 60 kDa HxuB protein in lanes B and C. Molecular weight position markers are also shown on the left side of this figure.

DETAILED DESCRIPTION OF THE PREFERRED EMBODIMENTS

1. *H. influenzae* Iron Sources

Figure 1:
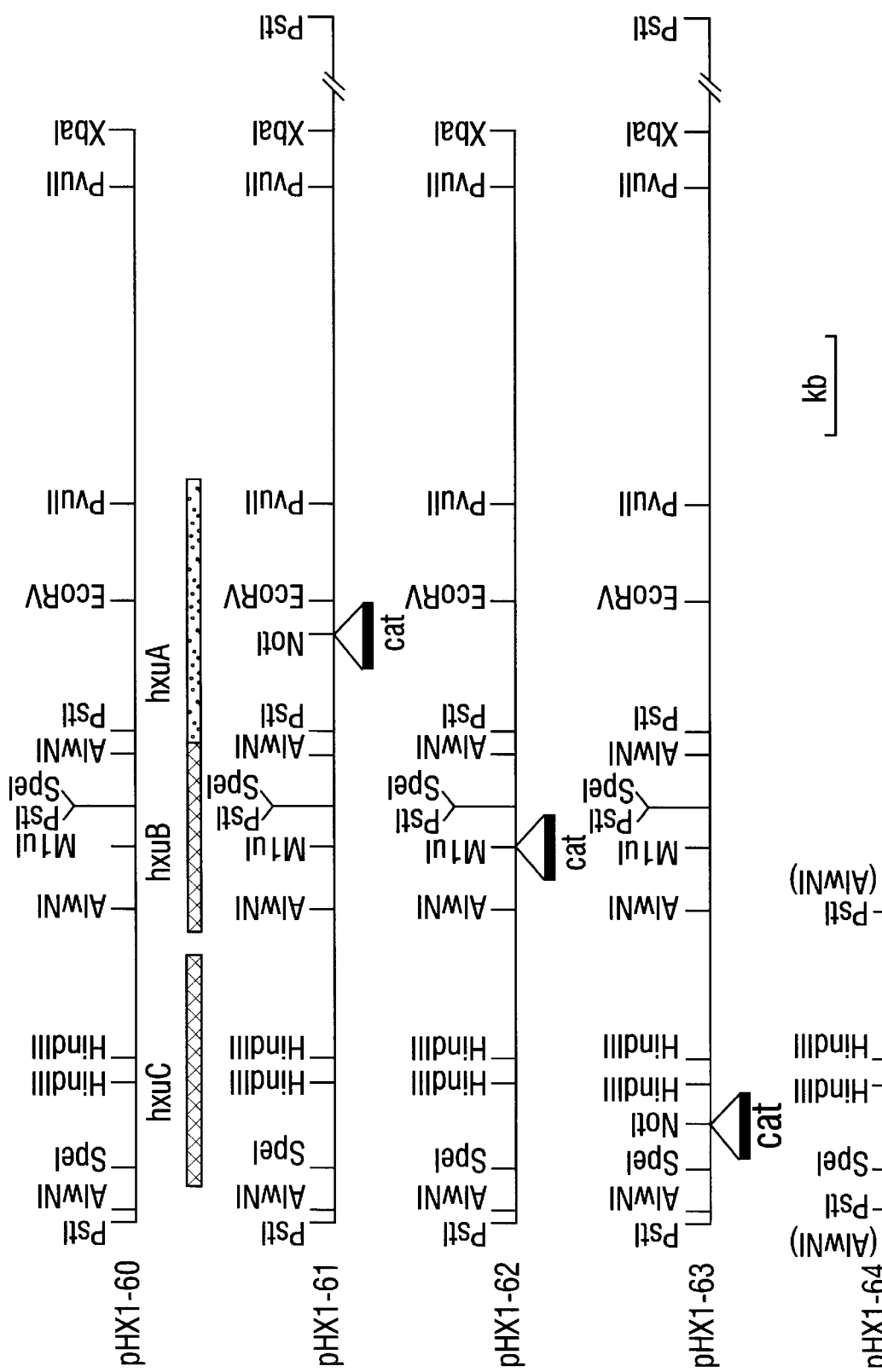
FIG. 1. Partial restriction enzyme maps of the DNA inserts in the recombinant plasmids used in this study. Plasmids pHX1-61 and pHX1-63 were derived from the pBR322-based recombinant plasmid pHX1-6 (17) whereas pHX1-60 and pHX1-62 are pBluescript II-based plasmids. The plasmid pHX1-64 is a pGJB103-based recombinant. The extent of the open reading frames for the hxuA, hxuB, and hxuC genes is depicted by the boxes beneath pHX1-60. The insertion sites for the cat cartridges in pHX1-61, pHX1-62, and pHX1-63 are indicated for each construct. The pair of diagonal marks on the right side of the pHX1-61 and pHX1-63 maps indicate that these insert maps were truncated for the purpose of clarity.

The requirement of *Haemophilus influenzae* for exogenously supplied heme and nicotinamide adenine dinucleotide (NAD) for aerobic growth (Evans, et al., 1974) distinguishes this bacterium from nearly every other facultative anaerobe. While other bacteria can use heme, a protoporphyrin IX (PPIX)-iron complex, as a source of inorganic iron (Otto, et al., 1992), *H. influenzae* requires the porphyrin ring of this molecule because this organism lacks the ability to convert δ-amino-levulinic acid to PPIX, the immediate biosynthetic precursor of heme (Granick and Gilder, 1946; White and Granick, 1963).

The identity of all of the *H. influenzae* cell envelope components involved in the uptake and transport of heme remains to be determined, but several macromolecules that interact with heme or affect heme utilization by *H. influenzae* have been described over the past three years. These include a periplasmic lipoprotein that binds heme and has structural similarity to an *Escherichia coli* dipeptide permease (Hanson and Hansen, 1991; Hanson et al., 1992), a 39 kDa heme-binding protein that has been reported to be present on the *H. influenzae* cell surface (Lee, 1992), and a recently identified protein with amino acid sequence similarity to the TonB protein of *E. coli* (Jarosik, et al., 1994). When expression of this TonB homologue was inactivated in both *H. influenzae* type b (*Hi*b) and nontypeable *H. influenzae* (NT*HI*) strains, the resultant isogenic mutants were unable to utilize heme in any form (Jarosik, et al., 1994).

*H. influenzae* possesses the ability to use not only free heme but also heme bound to serum carrier proteins (Stull, 1987). These latter heme:protein complexes are directly relevant to the growth of this organism in vivo, where free heme as such probably does not exist. It has been shown that *H. influenzae* can readily utilize heme:hemopexin, heme:albumin, and hemoglobin:haptoglobin complexes in vitro to satisfy its requirement for the PPIX molecule (Stull, 1987). In fact, *H. influenzae* receptors for both heme:hemopexin (Hanson et al., 1992) and hemoglobin (Hickman et al., 1993) have been described recently.

The present inventors have shown that a 100 kDa protein is required for utilization of here bound to the serum protein hemopexin by *Hi*b strain DL42 (Hanson, et al., 1992), while more recent evidence indicates that this 100 kDa protein is also synthesized by NT*HI* strains and is released by growing cells of both *Hi*b and NT*HI* strains into the culture medium (Cope et al., 1994). Nucleotide sequence analysis of hxuA genes from both a *Hi*b strain and a NT*HI* strain revealed that the two proteins were 87% identical, and this similarity at the amino acid level was reinforced by the finding that a NT*HI* HxuA protein could complement a hxuA mutation in a *Hi*b strain (Cope et al., 1994). Nucleotide sequence analysis of hxuA genes from both a *Hi*b strain and a NT*HI* strain revealed that the two proteins were 87% identical, and this similarity at the amino acid level was reinforced by the finding that a NT*HI* HxuA protein could complement a hxuA mutation in a *Hi*b strain (Cope et al., 1994).

Subsequent analyses revealed that utilization of not only heme:hemopexin but also that of other heme:protein carrier complexes as well as low concentrations of free heme by both *Hi*b and NT*HI* strains was dependent on the presence of a functional tonB gene (Jaroski et al., 1994). From this finding, it could be inferred that there must exist one or more TonB-dependent *H. influenzae* proteins that would be directly involved with heme transport. In support of this hypothesis, recent studies of the utilization of heme as an iron source by *Y. enterocolitica* indicated that both TonB and a TonB-dependent outer membrane protein (i.e., HemR) were essential for this process (Koebnik et al., 1993; Stojiljkovic and Hantke, 1992). However, it has also been reported that *H. influenzae* may contain a second hemopexin receptor that functions independently of the 100 kDa protein described immediately above (Wong et al., 1994).

The inventors have noted that the cloned *Hi*b DNA fragment that contains the hxuA gene encoding the 100 kDa heme:hemopexin-binding protein also expressed a protein with an apparent molecular weight of approximately 60 kDa. Linker insertion mutations in the recombinant plasmid pHX1-6 that eliminated expression of this 60 kDa protein also had an adverse effect on the expression of heme:hemopexin-binding activity by *Hi*b (Hanson et al., 1992).

2. hxuC and hxuB Genes

The present invention is directed to the identification and characterization of two genes, located in tandem immediately upstream from hxuA, that encode 60 kDa and 78 kDa outer membrane proteins and to various uses for these genes and their encoded proteins and peptides. The HxuC protein is shown to have certain amino acid sequence homology with outer membrane proteins from other bacteria that are considered to be TonB-dependent, including the hemR protein from *Y. enterocolitica* that is involved in the utilization by this pathogen of heme as an iron source (Stojiljkovic and Hantke, 1992). This appears to be the first description of a possible TonB-dependent outer membrane protein in *H. influenzae*.

As disclosed herein, to determine directly whether the HxuB and HxuC proteins were involved in heme utilization, these two genes were mutated by insertion of a cat cartridge into their respective ORFs. The mutated genes were introduced independently into the bacterial chromosome of the wild-type *Hi*b strain by transformation and subsequent allelic exchange. Comparison of the outer membrane protein profiles of these isogenic hxuB and hxuC mutants with that of the wild-type parent strain confirmed that both of these proteins were present in the *Hi*b outer membrane (FIG. 5).

Figure 4A:
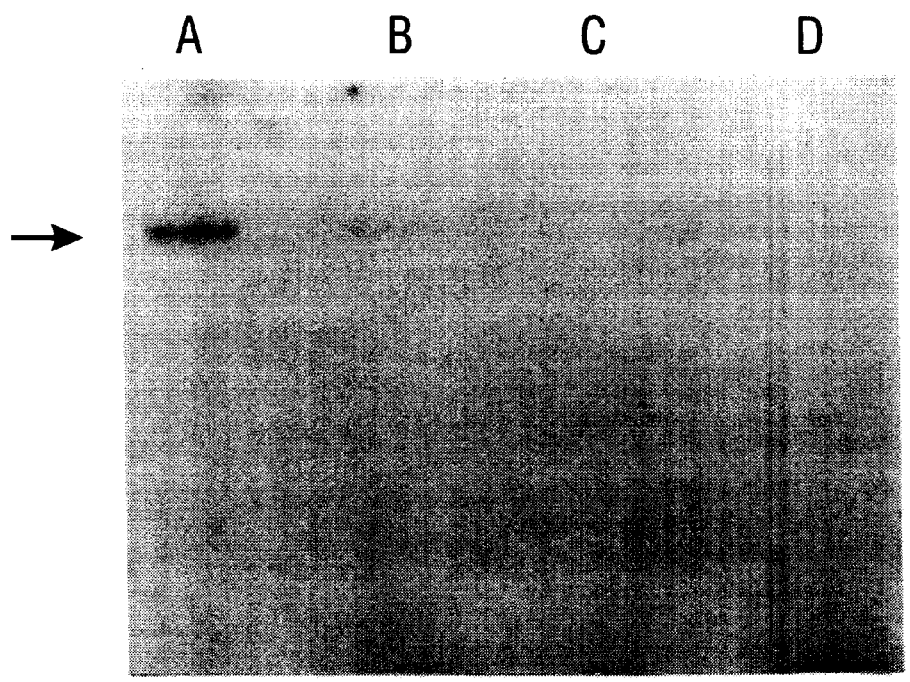
FIG. 4, Panel A and Panel B: Release of HxuA into the culture supernatant by wild-type, mutant, and recombinant H*i*b strains as revealed by detection of heme:hemopexin-binding activity.
Figure 4B:
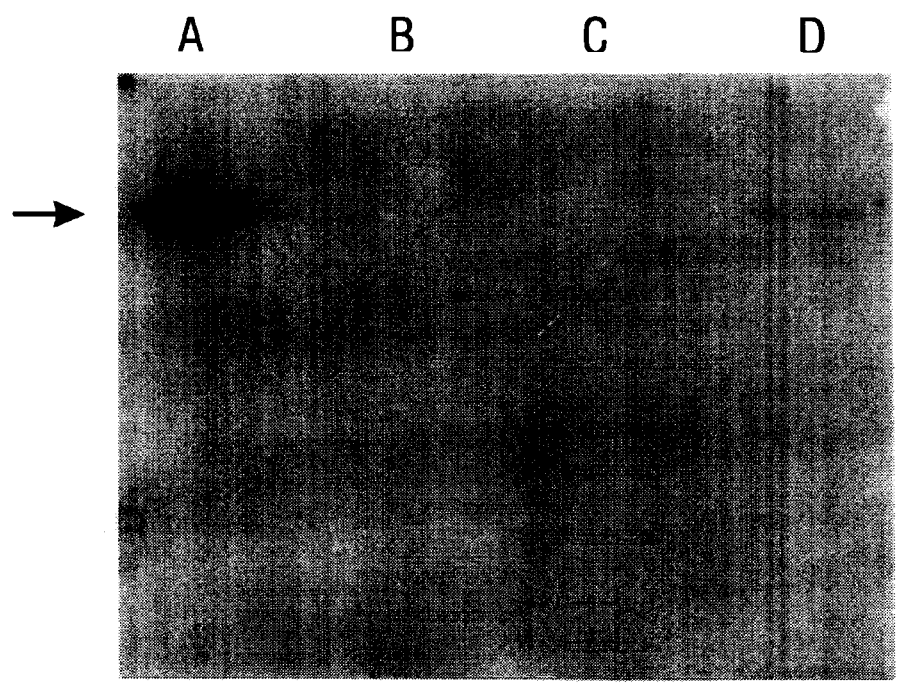
Figure 7:
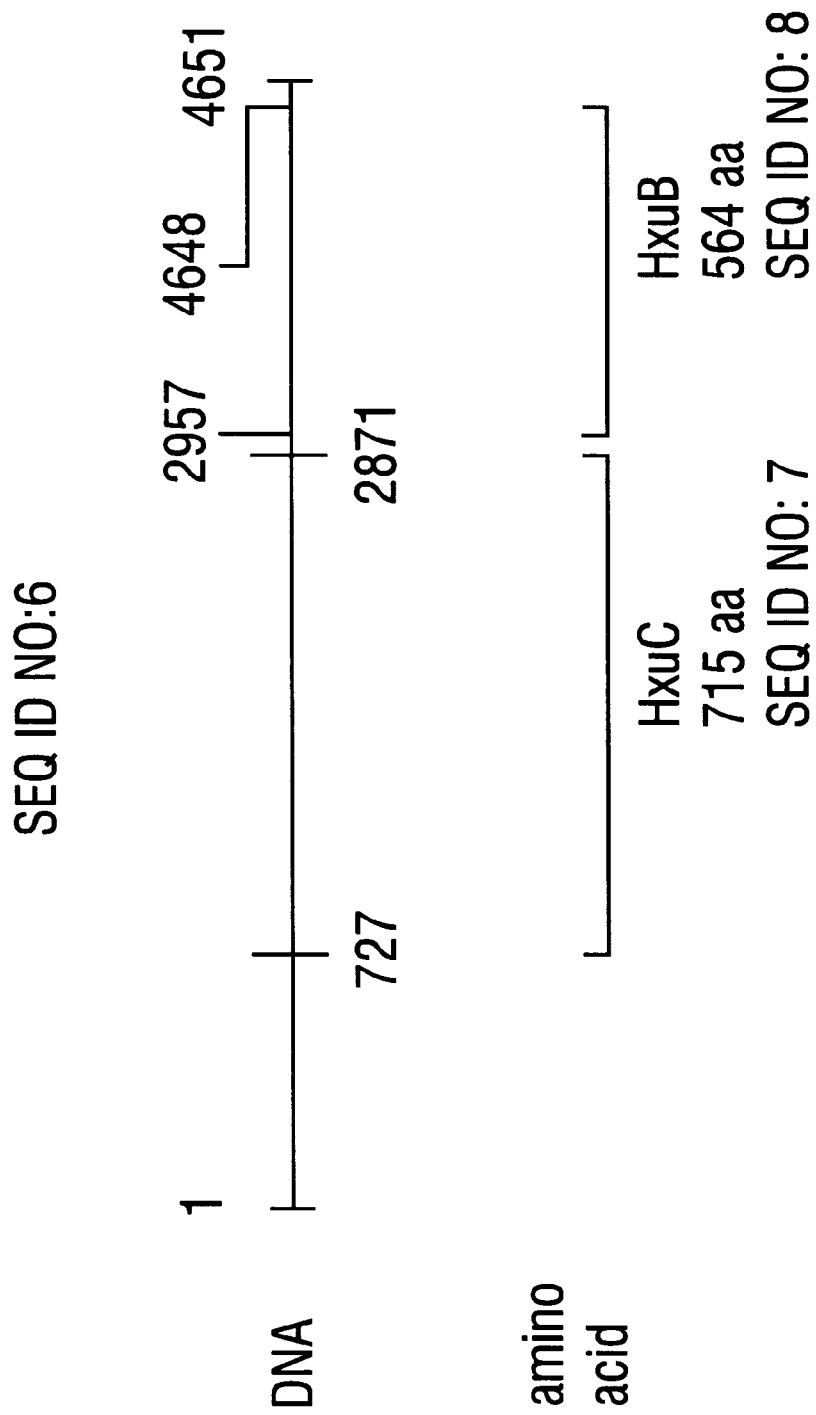
FIG. 7. Schematic representation of the hxuC and hxuB genes of NT*HI*, and the deduced amino acid sequences of the HxuC (SEQ ID NO:7) and HxuB (SEQ ID NO:8) proteins. The total DNA sequence is SEQ ID NO:6. The beginning of the hxuA gene that follows the hxuB genes, is also depicted (SEQ ID NO:4), with the encoded polypeptide portion being SEQ ID NO:5.

The presence of the cat cartridge in the hxuB gene eliminated expression of detectable levels of both HxuB (FIG. 5, lane D) and HxuA (FIG. 4, Panel 1, lane C). In DL42.63, the presence of the cat cartridge in the hxuC gene eliminated expression of HxuC (FIG. 5, lane B); however, barely detectable amounts of the HxuB (FIG. 5, lane B) and HxuA (FIG. 4, Panel 1, lane A) proteins were synthesized by this hxuC mutant, a finding that raised the possibility that the hxuB gene may have its own, independent promoter. The fact that the start codon for the hxuB gene is located nearly 100 nucleotides downstream from the termination codon for the hxuC gene, together with the identification of putative −35 and −10 consensus sequences in this intergenic region, give credence to this proposal. Alternatively, the very modest expression of the hxuB and hxuA genes in the hxuC mutant may have resulted from the presence of the cat cartridge in the hxuC gene; the cat gene in this cartridge does not have transcriptional terminators.

Mutations in the hxuB and hxuC genes had very different effects on the ability of *Hi*b to utilize heme. The hxuB mutant, unable to synthesize HxuB and HxuA, had a heme utilization phenotype indistinguishable from that of a hxuA mutant. Neither the hxuB nor the hxuA mutant could utilize heme bound to hemopexin (Table 3). This finding confirms the previously reported dependence of *Hi*b strain DL42 on the presence of a functional HxuA protein for growth on heme:hemopexin as the sole source of heme (Hanson et al., 1992). The hxuC mutant, unable to express HxuC while synthesizing barely detectable amounts of HxuB and HxuA, was also unable to utilize heme:hemopexin (Table 3). However, the hxuC mutant was also could not grow on low levels (10 $\mu$g/ml) of free heme. When a functional hxuC gene was supplied in trans, the hxuC mutant was able to grow readily on low levels of heme (Table 3), a finding that confirms the involvement of the HxuC protein in the utilization of free heme.

It is interesting to note that increasing the concentration of free heme in the growth medium to 50 $\mu$g/ml permitted growth of the hxuC mutant (Table 3). Similar results were obtained in studies with the *H. influenzae* tonB mutants, which could not grow when the heme concentration was 8.5 μg/ml but which readily grew in media containing heme at 50 μg/ml (Jarosik et al., 1994). These two sets of results suggest that *H. influenzae* must also possess a TonB-independent mechanism for utilization of relatively high levels of free heme. It is difficult to predict whether such a TonB-independent heme acquisition system would function or be relevant in vivo, where free heme, especially at high concentrations, is unlikely to be present.

While the HxuC protein is clearly involved in the utilization of low levels of free heme, the HxuB protein, like HxuA, appears to be essential for the utilization of heme:hemopexin. When a functional NT*HI* hxuA gene was provided in trans in a *Hi*b hxuB mutant, the presence of the NT*HI* HxuA protein did not allow utilization of heme:hemopexin in the absence of HxuB (Table 3). However, when this same NT*HI* hxuA gene was present in trans in a *Hi*b hxuA mutant that expressed HxuB, this recombinant strain was able to utilize heme:hemopexin (Table 3) and also released a functional NT*HI* HxuA protein from the cell (FIG. 5).

It is also noted that a data base search revealed that the protein with the most similarity to HxuB is the ShlB protein of *S. marcescens*. This outer membrane protein and the similar HpmB outer membrane protein of *Proteus mirabilis* (Uphoff and Welch, 1990; Welch, 1991) have been shown to be essential for the secretion and processing of the *S. marcescens* ShlA and *P. mirabilis* HpmA hemolysins, respectively (Braun et al., 1992; Schiebel et al., 1989; Uphoff and Welch, 1990; Welch, 1991). In contrast to the well-studied RTX cytotoxins (Welch, 1991; Welch et al., 1992), both of these hemolysins have leader peptides (Bruan et al., 1992; Schiebel et al., 1989) as does HxuA (Cope et al., 1994). Therefore, the role of HxuB in the utilization of heme:hemopexin is likely indirect, in that HxuB probably functions in the release of HxuA from the bacterial cell.

While the hxuA, hxuB, and hxuC genes are clearly important in heme utilization, little is known about the regulation of the expression of these genes. Recent studies involving the expression of transferrin-binding activity by *H. influenzae* indicate that heme concentrations, independent of iron levels, may control expression of certain outer membrane proteins involved in obtaining iron from transferrin (Morton et al., 1993). The presence of putative Fur boxes in front of both the hxuB and hxuC genes raises the possibility that some sort of control system may be involved in expression of these genes.

The present discoveries may be utilized in conjunction with certain techniques that are well-known in the biological arts and that are further described in the following sections.

Recombinant clones expressing either or both of the hxuB and hxuC genes may be used to prepare purified protein and peptide antigens as well as mutant or variant protein species in significant quantities. The selected antigens, and variants thereof, are proposed to have significant utility in diagnosing and treating *H. influenzae* infections. For example, it is proposed that these antigens, or peptide variants, or antibodies against such antigens may be used in immunoassays to detect *H. influenzae* or as vaccines or immunotherapeutics to treat *H. influenzae* infections.

The nucleic acid sequences that encode hxuB and/or hxuC genes, or their variants, may be useful in hybridization or polymerase chain reaction (PCR) methodology to detect *H. influenzae*. Accordingly, included in the present invention is information that may be used to prepare a wide variety of DNA fragments having a number of potential utilities, such as the preparation of relatively short immunogenic/antigenic peptidyl subfragments of the antigen, the use of DNA or RNA sequences in PCR and hybridization studies as probes for in vitro detection, as well as other useful medical and biomedical applications related to the research, diagnosis and treatment of *H. influenzae* and, possibly, other pathogenic infections.

In another embodiment of the present invention, whole cells or cell colonies can be used in the screening of natural and artificially derived compounds or mixtures to select those that are capable of complexing with the HxuB and HxuC proteins. This may be useful in the discovery of compounds that will inhibit or otherwise disrupt the iron uptake activities of this infective microorganism.

The present invention envisions various means for producing and isolating either or both of the HxuB and HxuC proteins, ranging from the isolation of purified or partially purified proteins from natural sources (e.g., from *H. influenzae* bacterial cells), or from recombinant DNA sources (e.g., *E. coli* or other microbial or eukaryotic cells). In the latter case, these novel Hxu proteins and, particularly, antigenic peptides derived therefrom, may be provided in essentially antigenically pure states in that they will be free of other *H. influenzae* epitopes.

Since antibodies, including monoclonal antibodies, to the HxuB and HxuC proteins are encompassed by the present invention, the use of immunoabsorbent techniques to purify these proteins, or their immunologically cross-reactive variants, is also contemplated. It is proposed that useful antibodies for this purpose may be prepared generally by the techniques disclosed hereinbelow, or as is generally known in the art for the preparation of monoclonals (see, e.g., U.S. Pat. Nos. 4,514,498 and 4,740,467), and those reactive with the desired protein or peptides selected.

Additionally, by application of techniques such as DNA mutagenesis, the present invention allows the ready preparation of so-called "second generation" molecules having modified or simplified protein structures. Second generation proteins will typically share one or more properties in common with the full-length antigen, such as a particular antigenic/immunogenic epitopic core sequence. Epitopic sequences can be provided on relatively short molecules prepared from knowledge of the peptide, or encoding DNA sequence information. Such variant molecules may not only be derived from selected immunogenic/antigenic regions of the protein structure, but may additionally, or alternatively, include one or more functionally equivalent amino acids selected on the basis of similarities or even differences with respect to the natural sequence.

3. Use of Nucleic Acid Sequences

As mentioned, in certain aspects, the DNA sequence information provided by the present disclosure allows for the preparation of relatively short DNA (or RNA) sequences having the ability to specifically hybridize to gene sequences of either or both of the hxuB and hxuC genes, including their genetic control elements. In these aspects, nucleic acid probes of an appropriate length are prepared based on a consideration of the natural sequence and those derived from flanking regions of the gene, such as regions upstream and downstream of the genes. The ability of such nucleic acid probes to specifically hybridize to hxuB and hxuC gene sequences lend them particular utility in a variety of embodiments. Importantly, the probes can be used in a variety of diagnostic assays for detecting the presence of pathogenic organisms in a given sample. However, other uses are envisioned, including the expression of protein products, the use of the sequence information for the preparation of mutant species primers, or primers for use in preparing other genetic constructions.

To provide certain of the advantages in accordance with the present invention, the preferred nucleic acid sequence employed for hybridization studies or assays would include sequences that have, or are complementary to, at least a 20 or so nucleotide stretch of the sequence, although sequences of 30 to 50 or so nucleotides are also envisioned to be useful. A size of at least 20 nucleotides in length helps to ensure that the fragment will be of sufficient length to form a duplex molecule that is both stable and selective. Molecules having complementary sequences over stretches greater than 20 bases in length are generally preferred, though, in order to increase stability and selectivity of the hybrid, and thereby improve the quality and degree of specific hybrid molecules obtained. Thus, one will generally prefer to design nucleic acid molecules having HxuB or HxuC gene-complementary stretches of nucleotides, or even longer, such as 30, 50, 100, 200 or such like, where desired. Such fragments may be readily prepared by, for example, directly synthesizing the fragment by chemical means, by application of nucleic acid reproduction technology, such as the PCR technology of U.S. Pat. No. 4,683,202, or by introducing selected sequences into recombinant vectors for recombinant production.

In that the HxuB and HxuC proteins of the present invention are present in Hib and NTHI pathogens, this invention will find particular utility as the basis for diagnostic hybridization assays for detecting hxuB and/or hxuC specific RNA or DNA in clinical samples. Exemplary clinical samples that can be used in the diagnosis of infections are thus any samples that could possibly include bacterial nucleic acid, including middle ear fluid, sputum, bronchoalveolar fluid and the like. A variety of hybridization techniques and systems are known that can be used in connection with the hybridization aspects of the invention, including diagnostic assays such as those described in Falkow et al., U.S. Pat. No. 4,358,535.

Accordingly, the nucleotide sequences of the invention are important for their ability to selectively form duplex molecules with complementary stretches of the hxuB and hxuC genes. Depending on the application envisioned, one will desire to employ varying conditions of hybridization to achieve varying degrees of selectivity of the probe toward the target sequence. For applications requiring a high degree of selectivity, one will typically desire to employ relatively stringent conditions to form the hybrids, for example, one will select relatively low salt and/or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, where one desires to prepare mutants employing a mutant primer strand hybridized to an underlying template, less stringent hybridization conditions are called for in order to allow formation of the heteroduplex. In these circumstances, one would desire to employ conditions such as 0.15 M–0.9 M salt, at temperatures ranging from 20° C. to 55° C. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, one may desire to employ nucleic acid probes to isolate variants from clone banks containing mutated clones. In particular embodiments, mutant clone colonies growing on solid media that contain variants of the hxuB and hxuC genes could be identified on duplicate filters using hybridization conditions and methods, such as those used in colony blot assays, to only obtain hybridization between probes containing sequence variants and nucleic acid sequence variants contained in specific colonies. In this manner, small hybridization probes containing short variant sequences of these genes may be utilized to identify those clones growing on solid media that contain sequence variants of the entire genes. These clones can then be grown to obtain desired quantities of the variant nucleic acid sequences or the corresponding antigens.

In clinical diagnostic embodiments, nucleic acid sequences of the present invention are used in combination with an appropriate means, such as a label, for determining hybridization. A wide variety of appropriate indicator means are known in the art, including radioactive, enzymatic or other ligands, such as avidin/biotin, that are capable of giving a detectable signal. In preferred diagnostic embodiments, one will likely desire to employ an enzyme tag such as urease, alkaline phosphatase or peroxidase, instead of radioactive or other environmentally undesirable reagents. In the case of enzyme tags, colorimetric indicator substrates are known that can be employed to provide a means visible to the human eye or spectrophotometrically, to identify specific hybridization with pathogen nucleic acid-containing samples.

In general, it is envisioned that the hybridization probes described herein will be useful both as reagents in solution hybridizations as well as in embodiments employing a solid phase. In embodiments involving a solid phase, the test DNA (or RNA) from suspected clinical samples, such as exudates, body fluids (e.g., middle ear effusion, bronchoalveolar lavage fluid) or even tissues, is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

In other embodiments, it is proposed that the hxuB and hxuC sequences, or variants thereof, may be used to provide highly specific and sensitive detection of H. influenzae when used as reagents in polymerase chain reaction (PCR) assays. In general, by applying the PCR technology as set out, e.g., in U.S. Pat. No. 4,683,202, one may utilize various portions of the HxuC and HxuB sequences as oligonucleotide probes for the PCR amplification of a defined portion of nucleic acid in a sample. The amplified portion of the sequence may then be detected by hybridization with a hybridization probe containing a complementary sequence. In this manner, extremely small concentrations of nucleic acid may detected in a sample.

hxuB and hxuC sequences may also be utilized in PCR formats for the in vitro preparation of desired quantities of selected portions of these genes. By amplifying selected gene portions and then incorporating those portions into vectors, one can also prepare recombinant clones that express protein variants, including subfragments of the antigens. In this manner, peptides carrying HxuB or HxuC epitopes may be prepared and utilized for various purposes.

The present section describes various uses of hxuB and hxuC gene sequences and DNA segments. The hybridization conditions must sometimes be precisely controlled to differentiate between the ability of one DNA or RNA strand to hybridize to hxuC or hxuB sequences rather than to other DNA or RNA segments of generally related genes or evolutionary-conserved sequences. Although the detection of families and related sequences has evident usefulness, the criteria for defining an hxuC-like or hxuB-like sequence are herein set forth as those conditions that do not allow hybridization to, for example, sequences such as hemR, btuB and cir sequences. Therefore, if the intention is to identify generally related sequences or gene families, the less stringent conditions will be chosen. However, if the intention is to define hxuC-like or hxuB-like equivalents, more stringent conditions will be chosen.

4. Vaccination with Nucleic Acids and Attenuated Organisms

Another aspect of the invention concerns using the hxuB and/or hxuC DNA segments themselves, or organisms containing such DNA segments, as immunizing agents to vaccinate against infection and disease. The technology for using DNA segments as vaccines has recently been developed and is generally termed "Genetic Immunization" or "DNA Vaccination" (Cohen, 1993). It is now known that cells can take up naked DNA and express the peptides encoded on their surface, thus stimulating an effective immune response, which includes the generation of cytotoxic T lymphocytes (killer T cells).

This approach is particularly suitable for use against viruses. Indeed, immunization with DNA has been successfully employed to protect animals from challenge with influenza A (Ulmer et al., 1993; incorporated herein by reference). By employing techniques similar to those described by Ulmer and colleagues, but using the hxuB and/or hxuC DNA segments of the present invention, the inventors contemplate that an effective vaccination strategy would be developed.

The utilization of this technology, and variations thereof, such as those described by Tang et al. (1992), Cox et al. (1993), Fynan et al. (1993), Wang et al. (1993) and Whitton et al. (1993), each incorporated herein by reference, is particularly suitable as it has already been shown to be successful against a form of influenza virus, the type of pathogen also targeted by the present invention. It is contemplated that virtually any type of vector, including naked DNA in the form of a plasmid, could be employed to generate an immune response in conjunction with a wide variety of immunization protocols, including parenteral, mucosal and gene-gun inoculations (Fynan et al., 1993).

The inventors also contemplate using hxuB and/or hxuC DNA segments in the context of a live attenuated organism as a vaccine vehicle. Here the hxuB and/or hxuC DNA segments would be expressed in one or more of the many live replicating organisms that are already used as attenuated live vaccines. This would essentially provide a new protein or proteins in an existing and approved vaccine system. Suitable organisms are viruses, such as vaccinia virus, and various bacteria, such as Salmonella.

5. Use of Host Cell Cultures and Vectors

Prokaryotic hosts are preferred for expression of the HxuB and/or HxuC proteins. Some examples of prokaryotic hosts are *E. coli* strain RR1 which is particularly useful. Others are *E. coli* LE392, *E. coli* B, *E. coli* X 1776 (ATCC No. 31537) as well as *E. coli* W3110 (F-, lambda-, prototrophic, ATCC No. 273325), bacilli such as *Bacillus subtilis*, or other enterobacteriaceae such as *Salmonella typhimurium* or *Serratia marcescens,* and various Pseudomonas species may be used.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is typically transformed using pBR322 (Bolivar et al., 1977) a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters that can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector that can be used to transform host cells, such as *E. coli* LE392.

Those promoters most commonly used in recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1980; EPO Appl. Publ. No. 0036776). While these are the most commonly used, other microbial promoters have been discovered and utilized, and details concerning their nucleotide sequences have been published, enabling a skilled worker to ligate them functionally with plasmid vectors (EPO Appl. Publ. No. 0036776).

In addition to prokaryotes, eukaryotic microbes, such as yeast cultures may also be used. *Saccharomyces cerevisiae,* or common baker's yeast is the most commonly used among eukaryotic microorganisms, although a number of other strains are commonly available. For expression in Saccharomyces, the plasmid YRp7, for example, is commonly used (Stinchcomb et al., 1979; Tschemper et al., 1980). This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, an origin of replication, and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (*Tissue Culture,* 1973). Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment that also contains the SV40 viral origin of replication (Fiers et al., 1978). Smaller or larger SV40 fragments may also be used, provided there is included the approximately 250 bp sequence extending from the Hind III site toward the Bg1 I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

6. Screening Assays

Host cells that have been transformed could be used in the screening of natural and artificially derived compounds or mixtures to select those that are capable of complexing with the HxuB and/or HxuC proteins. This could be useful in the search for compounds that inhibit or otherwise disrupt the ability of the microorganism to obtain iron. It is contemplated that effective pharmaceutical agents could be developed by identifying compounds that complex with HxuB and/or HxuC proteins, including, for example, compounds isolated from natural sources, such as plant, animal and marine sources, and various synthetic compounds. Natural or man-made compounds that may be tested in this manner could also include various minerals and proteins, peptides or antibodies.

7. Epitopic Core Sequences

As both the HxuB and HxuC proteins provided by this invention are outer membrane proteins, they are ideal targets for use as vaccines or immunoreagents for the treatment of various *Hi*b- and NT*HI*-related diseases. In this regard, particular advantages may be realized through the preparation of synthetic peptides that include epitopic/immunogenic core sequences. These epitopic core sequences may be identified as hydrophilic and/or mobile regions of the polypeptides or those that include a T cell motif. It is known in the art that such regions represent those that are most likely to promote B cell or T cell stimulation, and, hence, elicit specific antibody production.

An epitopic core sequence, as used herein, is a relatively short stretch of amino acids that is "complementary" to, and therefore will bind, antigen binding sites on antibodies. Additionally or alternatively, an epitopic core sequence is one that will elicit antibodies that are cross-reactive with the anti-HxuB and/or anti-HxuC antibodies. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would be on the order of about 15 amino acids in length, with 20 being the preferred minimum. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, that teaches the identification and preparation of epitopes from amino acid sequences on the basis of hydrophilicity, and in Chou-Fasman analyses. Moreover, numerous computer programs are available for use in predicting antigenic portions of proteins, examples of which include those programs based upon Jameson-Wolf analyses (Jameson and Wolf, 1988; Wolf et al., 1988) and that can be used in conjunction with the computerized peptide sequence analysis program (DNAStar Software, DNAStar, Inc., Madison, Wis.). See also U.S. Pat. No. 4,554,101 and Kyte and Doolittle (1982). Hydrophilic peptidyl regions of the HxuB and/or HxuC proteins can thus be identified and used as epitopic core sequences.

Syntheses of epitopic sequences, or peptides that include an antigenic epitope within their sequence, are readily achieved using conventional synthetic techniques, such as the solid phase method (e.g., through the use of commercially available peptide synthesizer such as an Applied Biosystems Model 430A Peptide Synthesizer). Peptide antigens synthesized in this manner may then be allocated in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of 7.0 to 7.5. Moreover, it may be desirable to include agents that will inhibit microbial growth, such as sodium azide or Merthiolate. For extended storage in an aqueous state it will be desirable to store the solutions at 4° C., or more preferably, frozen. Of course, where the peptide(s) are stored in a lyophilized or powdered state, they may be stored virtually indefinitely, e.g., in metered aliquots that may be rehydrated with a predetermined amount of water (preferably distilled) or buffer prior to use.

In addition to the peptidyl compounds described herein, the inventors also contemplate that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modelling and chemical design known to those of skill in the art. It will be understood that all such sterically similar constructs fall within the scope of the present invention.

8. Antigenically Functional Equivalent Amino Acids

As mentioned above, modification and changes may be made in the structure of the HxuB and/or HxuC proteins and peptides and still obtain a molecules having like, or otherwise desirable, characteristics. For example, certain amino acids may be substituted for other amino acids in a protein structure without appreciable loss of interactive binding capacity with structures such as, for example, antigen-binding regions of antibodies or binding sites on effector cells, such as T cells or macrophages. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. Equally, the same considerations may be employed to create a protein or polypeptide with countervailing (e.g., antagonistic) properties. It is thus contemplated by the inventors that various changes may be made in the sequence of HxuB and HxuC proteins or peptides (or underlying DNA) without appreciable loss of their biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. In particular, where peptides of about 50 or about 30 amino acids are concerned, it is contemplated that only about 8 or more preferably, about 4 or 5 amino acids may be changed within a given peptide. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged. In the case of the present invention.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid, as shown in Table 1.

TABLE 1

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

9. Preparation of Monoclonal Antibodies

Means for preparing and characterizing antibodies are well known in the art (See, e.g., Antibodies: A Laboratory Manual, 1988; incorporated herein by reference. The methods for generating monoclonal antibodies (MAbs) generally begin along the same lines as those for preparing polyclonal antibodies. Briefly, a polyclonal antibody is prepared by immunizing an animal with an HxuB or HxuC immunogenic composition in accordance with the present invention, and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified HxuB or HxuC protein, peptide or polypeptide. The immunizing composition is administered in a manner effective to stimulate antibody producing cells. Rodents such as mice and rats are preferred animals, however, the use of rabbit, sheep and/or frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media that support the growth of only the desired fused cells (hybridomas).

Any one of a number of myeloma cells may be used, as are known to those of skill in the art (Goding, 1986, pp. 65–66; Campbell, 1984, 75–83). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XXO Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976); and those using polyethylene glycol (PEG), such as 37% (v/v) PEG, by Gefter et al., (1977). The use of electrically induced fusion methods is also appropriate (Goding, 1986, pp. 71–74).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

In general, monoclonal antibodies to the desired HxuB and/or HxuC protein antigens can be used in both the diagnosis and treatment of *H. influenzae* infections, with their diagnostic uses being particularly important.

It is proposed that monoclonal antibodies in accordance with the present invention will find useful applications in standard immunochemical procedures, such as ELISAs and Western blot methods, as well as other procedures that may utilize anti-HxuB or anti-HxuC antibodies. Such specific MAbs are expected to be useful in various ways for the treatment of *H. influenzae* infections through, for example, their application in passive immunization procedures.

Additionally, it is proposed that MAbs specific to the HxuB and/or HxuC proteins may be utilized in other useful applications. For example, their use in immunoabsorbent protocols will be of use in purifying the native or recombinant proteins or variants thereof.

10. Preparation of Site-Specific Mutants

Site-specific mutagenesis is a well-known technique that may be used in the preparation of individual peptides, or biologically functional equivalent proteins or peptides, derived from the HxuB and/or HxuC antigen sequences, through specific mutagenesis of the underlying DNA. The technique further provides a ready ability to prepare and test sequence variants, by introducing one or more nucleotide sequence changes into the DNA. Site-specific mutagenesis allows the production of mutants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence that encodes one of the HxuB or HxuC protein antigens. An oligonucleotide primer bearing the desired mutated sequence is prepared, generally synthetically, for example, by the method of Crea et al. (1978). This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected HxuB and/or HxuC genes using site-directed mutagenesis is provided as a means of producing potentially useful mutant species and is not meant to be limiting as there are other ways in which such sequence variants may be obtained. For example, recombinant vectors encoding the desired HxuB or HxuC genes may be treated with mutagenic agents to obtain sequence variants (see, e.g., a method described by Eichenlaub, 1979) for the mutagenesis of plasmid DNA using hydroxylamine.

11. Immunoassays

As noted, it is proposed that HxuB and/or HxuC proteins and peptides of the invention will find utility as immunogens, e.g., in connection with vaccine development, or as antigens in immunoassays for the detection of reactive antibodies. Turning first to immunoassays, in their most simple and direct sense, preferred immunoassays of the invention include the various types of enzyme linked immunosorbent assays (ELISAs), as are known to those of skill in the art. However, it will be readily appreciated that the utility of HxuB and HxuC proteins and peptides is not limited to such assays, and that other useful embodiments include RIAs and other non-enzyme linked antibody binding assays and procedures.

In preferred ELISA assays, proteins or peptides incorporating HxuB or HxuC protein antigen sequences are immobilized onto a selected surface, preferably a surface exhibiting a protein affinity, such as the wells of a polystyrene microtiter plate. After washing to remove incompletely adsorbed material, one would then generally desire to bind or coat a nonspecific protein that is known to be antigenically neutral with regard to the test antisera, such as bovine serum albumin (BSA) or casein, onto the well. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween. These added agents also tend to assist in the reduction of nonspecific background. The layered antisera is then allowed to incubate for, e.g., from 2 to 4 hours, at temperatures preferably on the order of 25° to 27° C. Following incubation, the antisera-contacted surface is washed so as to remove non-immunocomplexed material. A preferred washing procedure includes washing with a solution such as PBS/Tween, or borate buffer.

Following formation of specific immunocomplexes between the test sample and the bound antigen, and subsequent washing, the occurrence and the amount of immunocomplex formation may be determined by subjecting the complex to a second antibody having specificity for the first. Of course, in that the test sample will typically be of human origin, the second antibody will preferably be an antibody having specificity for human antibodies. To provide a detecting means, the second antibody will preferably have an associated detectable label, such as an enzyme label, that will generate a signal, such as color development upon incubating with an appropriate chromogenic substrate. Thus, for example, one will desire to contact and incubate the antisera-bound surface with a urease or peroxidase-conjugated anti-human IgG for a period of time and under conditions that favor the development of immunocomplex formation (e.g., incubation for 2 hours at room temperature in a PBS-containing solution such as PBS-Tween).

After incubation with the second labeled or enzyme-tagged antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

12. Vaccine Preparation and Use

The present invention contemplates vaccines for use in both active and passive immunization embodiments. Immunogenic compositions proposed to be suitable for use as a vaccine may be prepared most readily directly from immunogenic HxuB and/or HxuC proteins and/or peptides. Preferably the antigenic material is extensively dialyzed to remove undesired small molecular weight molecules and/or lyophilized for more ready formulation into a desired vehicle.

The preparation of vaccines that contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables, either as liquid solutions or suspensions, solid forms suitable for solution in, or suspension in, liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants that enhance the effectiveness of the vaccines.

A preparation of H. influenzae outer membrane vesicles that contain HxuB and/or HxuC proteins or peptides could also be as the basis for a human vaccine, so long as the content of endotoxin (LPS) is reduced, eliminated or de-toxified. The preparation of such compositions that are essentially free from endotoxin can be achieved by following the published methodology, for example, U.S. Pat. No. 4,271,147 (incorporated herein by reference) discloses methods for the preparation of Neisseria meningitidis membrane proteins for use in vaccines; and Zollinger et al. (1978; 1979) describe the preparation of non-toxic protein and polysaccharide compositions essentially free from LPS.

HxuB- and HxuC-based vaccines may be conventionally administered parenterally, by injection, for example, either subcutaneously or intramuscularly. Additional formulations that are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10–95% of active ingredient, preferably 25–70%.

The proteins may be formulated into the vaccine as neutral or salt forms. Pharmaceutically acceptable salts, include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines may be administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered will be readily determinable by the skilled practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° to 101° C. for 30 second to 2 minute periods respectively. Aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

Of course, in light of the new technology on DNA vaccination, it will be understood that virtually all such vaccination regimens will be appropriate for use with DNA vectors and constructs, as described by Ulmer et al. (1993), Tang et al. (1992), Cox et al. (1993), Fynan et al. (1993), Wang et al. (1993) and Whitton et al. (1993), each incorporated herein by reference. In addition to parenteral routes of DNA inoculation, including intramuscular and intravenous injections, mucosal vaccination is also contemplated, as may be achieved by administering drops of DNA compositions to the nares or trachea. It is particularly contemplated that a gene-gun could be used to deliver an effectively immunizing amount of DNA to the epidermis (Fynan et al., 1993).

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

Identification of hxuC and hxuB Genes in *Hi*b

1. Bacterial Strains and Culture Conditions

The wild-type *H. influenzae* type b (*Hi*b) strain DL42 used in this study has been described previously (Cope et al., 1991; Hansen et al., 1988). The various isogenic mutant and recombinant strains derived from *Hi*b strain DL42 in the course of this study are listed in Table 2. All of these strains were grown routinely in Brain Heart Infusion (BHI) broth (Difco Laboratories, Detroit, Mich.) supplemented with Levinthal's base (BHIs) (Alexander, 1965) and with tetracycline (5 $\mu$g/ml) or chloramphenicol (2 $\mu$g/ml) as necessary. For preparation of outer membrane vesicles and culture supernatants, *H. influenzae* strains and mutants were grown in BHI broth containing NAD (10 $\mu$g/ml) and hemin (10 $\mu$g/ml), with antimicrobial supplementation when necessary.

Testing of the ability of *H. influenzae* strains and mutants to utilize various heme sources was accomplished by using BHI agar plates containing NAD (10 $\mu$g/ml) and the heme source at various concentrations, again with antimicrobial supplementation when necessary. Broth cultures were grown at 37° C. with aeration; agar plates were incubated at this same temperature in an atmosphere of 5% $CO_2$-95% air. The *Escherichia coli* cloning host HB101 was grown in LB medium (Sambrook et al., 1989) with appropriate antimicrobial supplementation.

TABLE 2

Bacterial Strains and Plasmids Used.

| Strain or plasmid | Genotype or description | Source or reference |
|---|---|---|
| Bacterial strain | | |
| DL42 | Wild-type Hib strain | Cope et al., 1990 |
| DL42.61 | DL42 with a cat cartridge inserted into the hxuA gene, obtained by transforming DL42 with linearized pHX1-61. This mutant does not express HxuA and cannot utilize heme:hemopexin as a source of heme | This Study |
| DL42.62 | DL42 with a cat cartridge inserted into the hxuB gene, obtained by transforming DL42 with linearized pHX1-62. This mutant does not express HxuA and cannot utilize heme:hemopexin as a source of heme for growth. | This study |
| DL42.63 | DL42 with a cat cartridge inserted into the hxuB gene, obtained by transforming DL42 with linearized pHX1-63. This mutant does not express HxuA and expresses barely detectable levels of HxuB and HxuA. This mutant cannot use low levels of free heme for growth and also cannot utilize heme:hemopexin as a source of heme. | This study |
| DL42.61.T | Chloramphenicol-sensitive transformant obtained by transforming DL.42.61 with a BamHI digest of pHX1-60. This transformant exhibits the heme utilization phenotype of the wild-type strain. | This study |
| DL42.62.T | Chloramphenicol-sensitive transformant obtained by transforming DL52.62 with a BamHI digest of pHX1-60. This transformant exhibits the heme utilization phenotype of the wild-type strain. | This study |
| DL42.63.T | Chloramphenicol-sensitive transformant obtained by transforming DL42.63 with a BamHI digest of pHX1-60. This transformant exhibits the heme utilization phenotype of the wild-type strain. | This study |
| DL42 (pGJB103) | DL42 containing the shuttle vector pGJB103 | This study |
| DL42.63 (pGJB103) | DL42.63 containing pGJB103 | This study |

TABLE 2-continued

Bacterial Strains and Plasmids Used.

| Strain or plasmid | Genotype or description | Source or reference |
|---|---|---|
| DL42.63 (pHX1-64) | DL42.63 with the recombinant plasmid pHX1-64 containing the wild-type hxuC gene; this recombinant strain can grow on low levels of free heme but cannot utilize heme:hemopexin. | This study |
| DL42 (pSET200) | DL42 with the recombinant plasmid pSET200 containing the NTHI hxuA gene. | This study |
| DL42.61 (pSET200) | DL42.61 with pSET200 containing the NTHI hxuA gene; this recombinant strain can utilize heme:hemopexin. | This study |
| DL42.62 (pSET200) | DL42.62 containing pSET200; this strain cannot utilize heme:hemopexin. | This study |
| DL42.63 (pSET200) | DL42.63 containing pSET200; this strain cannot utilize heme:hemopexin. | This study |

TABLE 2-continued

Bacterial Strains and Plasmids Used.

| Strain or plasmid | Genotype or description | Source or reference |
|---|---|---|
| pHX1-6 | pBR322 containing a 13.6 kb PstI fragment of Hib DL42 chromosomal DNA. This insert contains the hxuA, hxuB, and hxuC genes. | This study |
| pHX1-60 | pBluescript II with a 10.5 kb PstI-XbaI fragment from pHX1-6 containing the hxuA, hxuB, and hxuC genes. | This study |
| pHX1-61 | pHX1-6 with a cat cartridge inserted into a NotI linker within the hxuA gene. | This study |
| pHX1-62 | pHX1-60 with a cat cartridge inserted into the MluI site with the hxuB gene. | This study |
| pHX1-63 | pHX1-6 with a cat cartridge inserted into a NotI linker within the hxuC gene. | This study |
| pHX1-64 | pGJB103 containing only the hxuC gene from DL42. | This study |
| pSET200 | pGJB103 with an 11 kb insert from NTHI strain N182 that contains a functional NTHI hxuA gene; this insert contains only the terminal one-third of the NTHI hxuB gene and does not contain the NTHI hxuC gene. | Cope et al., 1994 |

TABLE 3

Utilization of Free Heme and Heme:Protein Compounds by Wild-Type and Mutant Hib Strains

| Strain | Heme (10 µg/ml) | Heme (50 µg/ml) | Hemoglobin | Hemoglobin: Haptoglobin | Heme: Hemopexin |
|---|---|---|---|---|---|
| DL42 | + | + | + | + | + |
| DL42.61 [hxuA mutant] | + | + | + | + | − |
| DL42.61.T | + | + | + | + | + |
| DL42.62 [hxuB mutant] | + | + | + | + | − |
| DL42.62.T | + | + | + | + | + |
| DL42.63 [hxuC mutant] | − | + | + | + | − |
| DL42.63.T | + | + | + | + | + |
| DL42.63 (pHX 1–64) | + | + | + | + | − |
| DL42 (pSET200) | + | + | + | + | + |
| DL42.61 (pSET200) | + | + | + | + | + |
| DL42.62 (pSET200) | + | + | + | + | − |
| DL42.63 (pSET200) | − | + | + | + | − |

*Growth as evidenced by development of single colonies on BHI/NAD agar supplemented with the indicated heme compounds.

TABLE 2-continued

Bacterial Strains and Plasmids Used.

| Strain or plasmid | Genotype or description | Source or reference |
|---|---|---|
| Plasmids | | |
| pGJB103 | Shuttle vector capable of replication in both E. coli and H. influenzae, $Amp^R$ $Tet^R$ | Barcak et al., 1991 |
| pBR322 | Cloning vector, $Amp^R$ $Tet^R$ | Sambrook et al., 1989 |
| pBluescript II | Cloning vector, $Amp^R$ | Sambrook et al., 1989 |

2. Plasmids

The plasmid pBluescript II SK+ was obtained from Stratagene (La Jolla, Calif.). The plasmid shuttle vector pGJB103 was obtained from Gerard J. Barcak (Johns Hopkins University, Baltimore, Md.) and can be prepared as described in Barcak et al. (1991) and Tomb et al. (1989). The recombinant plasmid pHX1-6 possesses a 13.6 kb insert of Hib strain DL42 chromosomal DNA that contains the hxuA gene encoding the 100 kDa heme:hemopexin-binding protein (Hanson et al., 1992). The recombinant plasmid pSET200 has an 11 kb insert of NTHI strain N182 chromosomal DNA that contains the gene encoding the 100 kDa heme:hemopexin-binding HxuA protein of this NTHI strain (Cope et al., 1994).

3. Recombinant DNA Methods

Standard recombinant DNA methods including restriction enzyme digests, ligation reactions, agarose gel electrophoresis, and plasmid purifications were performed as previously described (Sambrook et al., 1989). Restriction enzymes, DNA polymerase/Klenow fragment and NotI linkers were purchased from New England Biolabs (Beverly, Mass.). T4 DNA ligase was purchased from GIBCO-BRL (Bethesda, Md.). Random linker insertion mutagenesis was performed as described by Hanson and Hansen (1991) with eight-base pair NotI linkers (GCGGCCGC). The cat gene encoding chloramphenicol acetyltransferase and lacking an internal EcoRI site was derived from plasmid pUC4DEcat which was obtained from Dr. Bruce A. Green. After excision from pUC4DEcat with EcoRI, NotI linkers were added to the cat cartridge (Hanson et al., 1992).

4. Nucleotide Sequencing

*H. influenzae* DNA inserts contained in pBluescript II SK+ were sequenced by standard techniques, including the use of nested deletions (Sambrook et al., 1989). In all cases, both strands were sequenced in their entirety.

5. Results

A 10.5 kb PstI-XbaI fragment derived from the 13.6 kb PstI fragment in pHX1-6 (Hanson et al., 1992) was subcloned into pBluescript II SK+, yielding the recombinant plasmid pHX1-60 (FIG. 1). Nucleotide sequence analysis of a 5 kb region located immediately upstream from the *Hi*b DL42 hxuA gene (Cope et al., 1994) in this plasmid revealed the presence of two open reading frames (ORFs) arranged in tandem. These encoded proteins with predicted molecular weights of approximately 62 and 80 kDa, and these genes were tentatively designated as hxuB and hxuC, respectively (FIG. 1). The nucleotide sequence including both ORFs is designated SEQ ID NO:1, and the deduced amino acid sequences of the proteins encoded by each of the two ORFs are designated SEQ ID NO:2 (HxuC) and SEQ ID NO:3 (HxuB). In contrast to the upstream region, sequence analysis of the 500-bp region immediately downstream from hxuA did not detect any new ORFs.

EXAMPLE II

Features of the *Hi*b hxuC Sequence

1. Nucleotide Sequence Analysis

After sequencing both strands in their entirety, DNA sequence information was analyzed using the Intelligenetics Suite package and programs from the University of Wisconsin Genetics Computer Group software sequence analysis package (Devereux et al., 1984).

2. Results

Figure 2:
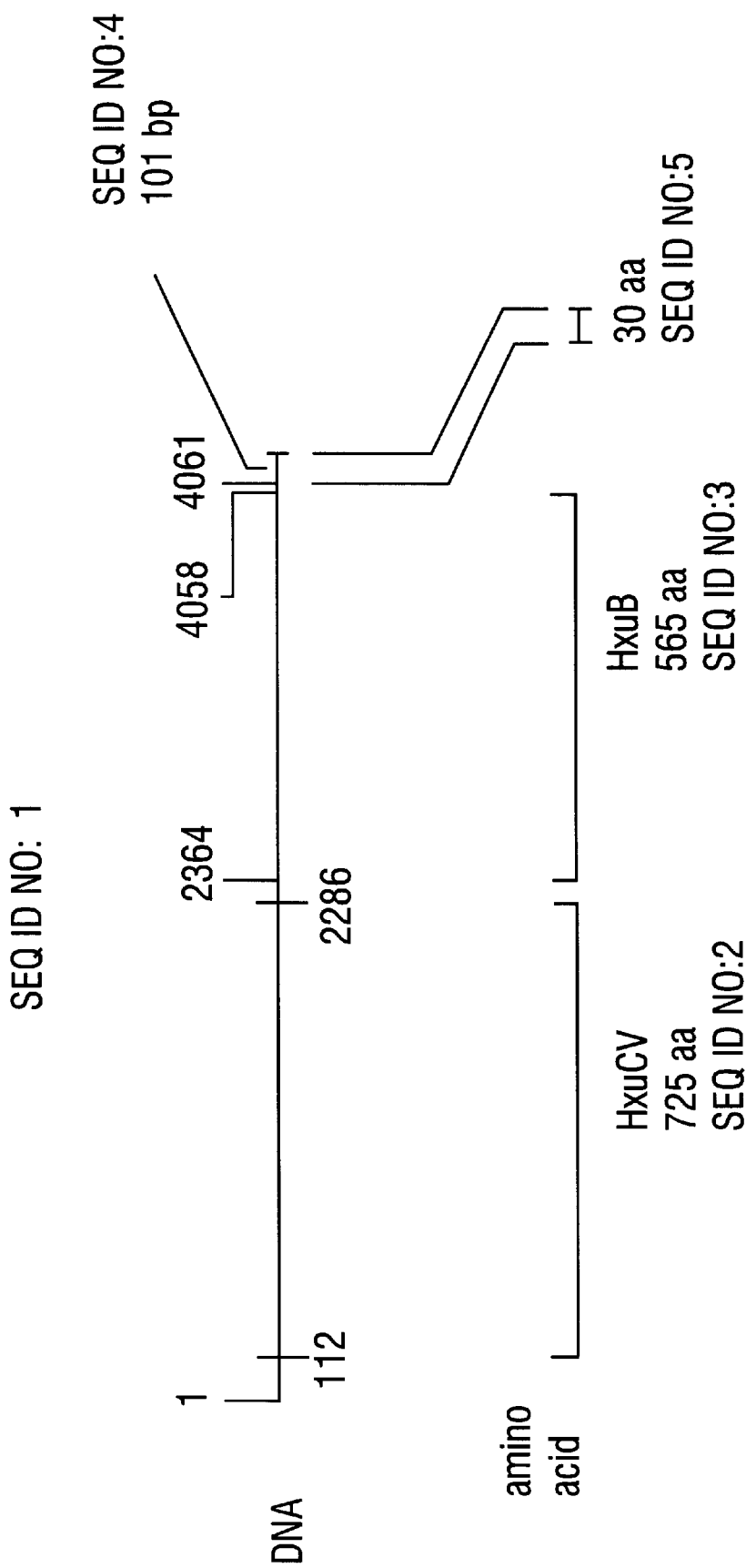
FIG. 2. Schematic representation of the hxuC and hxuB genes of H*i*b strain DL42, and the deduced amino acid sequences of the HxuC (SEQ ID NO:2) and HxuB (SEQ ID NO:3) proteins. The total DNA sequence is SEQ ID NO:1. The beginning of the hxuA gene that follows the hxuB genes, is also depicted (SEQ ID NO:4), with the encoded polypeptide portion being SEQ ID NO:5.

The translational start site for the ORF designated hxuC is located at nucleotides 112–114 of SEQ ID NO:1 (FIG. 2). This ATG codon is located 7 nucleotides downstream from a sequence (5'-AGGA-3') with homology to ribosomal binding sites (Shine and Dalgarno, 1975). Putative −35 and −10 consensus sequences were also identified upstream from the start codon.

A 19-nucleotide sequence (5'-GATTATTATTGTAATCATC-3'; residues 41 through 59 of SEQ ID NO:1) with some similarity (13/19 matches) to the *E. coli* Fur binding site consensus sequence (Litwin and Calderwood, 1993) was also located upstream from the start codon. Whether this sequence plays any role in the regulation of expression of the hxuC gene or that of the downstream hxuB and hxuA genes remains to be determined. Sequence analysis of the 500-bp region immediately upstream from hxuC did not reveal any new ORFs.

EXAMPLE III

Features of the *Hi*b HxuC Protein

1. N-terminal Amino Acid Sequence Analysis

Outer membrane vesicles of both the wild-type *Hi*b strain DL42 and the recombinant *Hi*b strain DL42.63(pHX1-64) were solubilized and subjected to SDS-PAGE as described by Kimura et al. (1985). The 60 kDa HxuB protein band was excised from gels containing proteins from the former strain and the 78 kDa HxuC protein band was derived from the latter strain. These proteins were then subjected to SDS-PAGE using the method of Hunkapiller et al. (1983). The gel-resolved protein bands were transferred to a polyvinylidene difluoride membrane by the method of Matsudaira (1987) and subjected to N-terminal amino acid analysis as described by Hansen et al. (1989).

2. Results

The ORF initiating at nucleotide 112 of SEQ ID NO:1 begins with a hydrophobic amino acid sequence similar to those of leader peptides (Sjostrom et al., 1987; von Heijne, 1985). Two possible signal peptidase I cleavage sites (i.e., A-X-A) were identified at amino acid residues 17–19 and 19–21 of SEQ ID NO:2. N-terminal amino acid sequence analysis of the *Hi*b DL42 HxuC protein purified from outer membranes of the recombinant strain DL42(pHX1-64) revealed that the second of these two sites was actually used for processing. The HxuC precursor had a calculated molecular weight of 80,843; after processing, the calculated molecular weight of the mature HxuC protein was 78,668. The HxuC protein has a phenylalanine residue as its C-terminal amino acid; this finding is consistent with HxuC being present in the *Hi*b outer membrane (described below) (Stuyve et al., 1991).

When the amino acid sequence of HxuC was compared to those of other protein in the available data bases, HxuC was found to have certain similarities with the class of outer membrane proteins that are described as being TonB-dependent (Hannavy and Higgins, 1991; Postle, 1990), such as HemR (*Yersinia enterocolitica* heme-binding protein (Stojiljkovic and Hantke, 1992)), BtuB (*E. coli* vitamin $B_{12}$ receptor (Heller and Kadner, 1985)), and Cir (*E. coli* colicin I receptor (Nau and Konisky, 1989)).

HxuC was found to possess a classic "TonB box" near its N-terminus (between residues 6 and 18 of SEQ ID NO:2), as well as the other six regions that are common to this type of outer membrane protein. The other motif sequence regions include Asp Ser Ile Asn Val Ile Ala Thr, between residues 27 and 34 of SEQ ID NO:2 and SEQ ID NO:7; Ile Pro Asn Val Asp, between residues 67 and 71 of SEQ ID NO:2 and SEQ ID NO:7; Val Val Gln Val Ile Asp Gly Val Arg Gln Asn, between residues 93 and 103 of SEQ ID NO:2 and SEQ ID NO:7; Glu Ile Glu Val Ile Lys Gly Pro Ser Ser Ser Leu Trp Gly Ser Gly Ala Leu Gly Gly Val Val Ala Met Arg Thr, between residues 121 and 146 of SEQ ID NO:2 and SEQ ID NO:7; Leu Arg Pro Glu Thr Ala Lys Asn Lys Glu, between residues 503 and 512 of SEQ ID NO:2 and between residues 505 and 514 of SEQ ID NO:7; Ala Arg Leu Ser Gly Ile Glu, between residues 587 and 593 of SEQ ID NO:2 and between residues 577 and 583 of SEQ ID NO:7; Leu Asp Phe Ala Leu Glu Asn Leu Phe Asp Arg Lys Tyr, between residues 681 and 693 of SEQ ID NO:2 and between residues 691 and 703 of SEQ ID NO:7; and Gly Arg Asn Ala Lys Ile Ser Ala Val Tyr Ser Phe, between residues 714 and 725 of SEQ ID NO:2 and between residues 704 and 715 of SEQ ID NO:7. Each of the above sequences have contiguous stretches of between two and eight amino acids that have identity with sequences from HemR, BtuB and/or Cir.

However, it should be noted here that these sequence regions are scattered "motif" elements and do not reflect extensive stretches of contiguous sequence complementarity. Furthermore, prior to the present invention, there was no reason to suspect that the HxuC proteins would have sequences in common with the TonB-dependent outer membrane proteins.

EXAMPLE IV

Features of the Hib hxuB Gene

Using similar analyses to those described above in Example II, the features of the HxuB ORF were examined. Two possible translational start sites for this ORF were located 74 and 81 nucleotides, respectively, downstream from the termination codon for hxuC. Possible −35 and −10 consensus sequences were also located in appropriate positions 5' from these two closely grouped ATG codons while two possible ribosomal binding sites (5'-AGGA-3') were identified immediately upstream from these two ATG codons. A 20-nucleotide sequence (5'-CTTTGGAAAACGCCCTAAAG-3'; 2295–2304 of SEQ ID NO:1) with weak similarity to the E. coli Fur box consensus sequence was also identified in the same region as the possible −35 consensus sequences. The start codon for the hxuA gene was located 12 nucleotides downstream from the stop codon for the hxuB gene (SEQ ID NO:1).

EXAMPLE V

Features of the Hib HxuB Protein

The ORF beginning with nucleotide 2364 (SEQ ID NO:3) encoded a protein with a calculated molecular weight of 62,664. Inspection of the deduced amino acid sequence at the N-terminal end of this protein revealed that it was mainly hydrophobic and resembled a leader peptide. A putative signal peptidase I cleavage site (i.e., V-M-A) was located at amino acid residues 24–26 of SEQ ID NO:3, such that the predicted molecular weight of the mature HxuB protein was 59,832. N-terminal amino acid sequence analysis of gel-purified HxuB protein from Hib strain DL42 outer membranes confirmed the existence of the proposed leader peptide. The carboxyl-terminal residue of the HxuB polypeptide was phenylalanine, a finding consistent with the presence of HxuB in the Hib outer membrane (Stuyve et al., 1991).

When the available protein data bases were searched, the protein with the greatest similarity to HxuB was the ShlB protein of Serratia marcescens. This 62 kDa outer membrane protein is required for secretion and activation of the ShlA hemolysin of S. marcescens (Braun et al., 1992; Poole et al., 1988; Schiebel et al., 1989).

EXAMPLE VI

Monoclonal Antibodies (Mabs)

A novel Mab, termed 2B7, was generated and shown to be reactive with the 60 kDa HxuB protein. To obtain this Mab, mice were immunized with outer membrane vesicles prepared from NTHI strain TN106 cells grown under iron limitation. Spleen cells from these immunized mice were fused with SP2/0-Ag14 plasmacytoma cells and lymphocyte hybridomas were selected, as described by Robertson et al., (1982). Culture supernatants from these lymphocyte hybridomas were screened in Western blot analysis using TN106 outer membrane vesicles as antigen. Mab 2B7 was identified as an IgG1 Mab that reacted with an antigen with an apparent molecular weight of approximately 60 kDa in SDS-PAGE. The reactivity of this Mab with the 60 kDa HxuB protein was confirmed by the use of this Mab in Western blot analysis against whole cell lysates from the recombinant strain E. coli RRI(pHX1-6) that expresses the Hib 60 kDa HxuB protein.

Mab 6D3 was shown to be reactive with the 80 kDa HuxC protein. To obtain this Mab, mice were immunized with 5 μg HxuC protein, gel-purified from DL42.63 (pHx1-64) outer membrane vesicles. Spleen cells from these immunized mice were fused with SP2/0-Ag14 plasmacytoma cells and lymphocyte hybridomas were selected, as described by Robertson et al., (1982). Culture supernatants from these lymphocyte hybridomas were screened in Western blot analysis using DL42.63 (pHx1-64) outer membrane vesicles. Mab 6D3 was identified as an IgG2a Mab that reacted with an antigen with an apparent molecular weight of approximately 80 kDa in SDS-PAGE. The reactivity of this Mab with the 80 kDa HxuC protein was confirmed by the use of the Mab in Western blot analysis against whole cell lysates from the recombinant strain E coli RR1 (pHx1-6) that expresses the Hib 80 kDa HxuC protein.

Also used in these studies is Mab 4C11, directed against the 100 kDa heme:hemopexin-binding HxuA protein from Hib strain DL42, as described in Cope et al. (1994), incorporated herein by reference.

EXAMPLE VII

Construction of hxuB and hxuC Mutants

The close proximity of the hxuB and hxuC genes to the hxuA gene encoding the 100 kDa heme:hemopexin-binding protein raised the possibility that these two upstream ORFs might express proteins involved in some aspect of heme utilization. To test this hypothesis directly, isogenic hxuB and hxuC mutants were constructed by means of insertion mutagenesis and allelic exchange.

1. *H. influenzae* Genetic Transformation Methods

The glycerol-lactate shock method (Stuy and Walter, 1986) was used to transform Hib strain DL42 with the shuttle vector pGJB103 and recombinant plasmids derived from this vector. Transformants were selected on BHIs agar plates containing tetracycline (5 μg/ml). For transformation of Hib with linear DNA molecules, the $M_{IV}$-based method of Herriott and colleagues was employed (Herriott et al., 1970).

2. Southern Blot Analysis

Chromosomal DNA purified from wild-type, mutant, and transformant *H. influenzae* strains was digested to completion with appropriate restriction enzymes and probed in Southern blot analysis by using the non-radioactive ECL random prime labeling and detection system (Amersham, Arlington Heights, Ill.) as described by the manufacturer. The DNA probes used in these studies included the 1.2 kb cat gene from pUC4DEcat, a 1.2 kb SpeI-HindIII fragment representing the 5'-half of the hxuC gene, a 1.4 kb AlwnI fragment containing nearly all of the hxuB gene, and a 2.2 kb PstI-PvuII fragment comprising the majority of the hxuA gene.

3. hxuB Mutant Results

To inactivate the hxuB gene, the recombinant plasmid pHX1-60 (FIG. 1) was digested to completion with MluI and then the ends were filled in by treatment with DNA polymerase I/Klenow fragment. BglII linkers were then added to the linearized molecule and a cat cartridge with BamHI ends was ligated onto these BglII ends, yielding the mutated plasmid pHX1-62 (FIG. 1). This plasmid was linearized by digestion with BamHI and used to transform the wild-type Hib strain DL42. Transformants were selected for chloramphenicol resistance and whole cell lysates of several of these were shown to lack reactivity with the HxuB-specific Mab 2B7 in Western blot analysis. One of these was selected for further study and designated DL42.62 (Table 2). Southern blot analysis was used to confirm that proper allelic exchange, involving the replacement of the wild-type hxuB gene with the mutated hxuB gene, had occurred in DL42.62 (FIG. 3, Panel 3 and Panel 4).

4. hxuC Mutant Results

A NotI linker insertion in the recombinant plasmid pHX1-6, originally characterized as preventing expression of heme:hemopexin-binding activity by the recombinant *E. coli* strain containing this mutated plasmid (Hanson et al., 1992), was localized to the 5'-half of the hxuC gene (FIG. 1). A cat cartridge with NotI ends was ligated into this site, yielding the mutated plasmid pHX1-63 which was digested with BamHI and used to transform the *Hi*b wild-type strain DL42. Transformants were selected for resistance to chloramphenicol and screened for an inability to bind heme-:hemopexin. One of these transformants, designated DL42.63, was selected for further study. Southern blot analysis was used to confirm that allelic exchange had occurred properly in DL42.63 (FIG. 3, Panel 1 and Panel 2).

EXAMPLE VIII

Construction of a hxuA Mutant

In a previous study of the inventors', NotI linker insertion mutagenesis was used to produce a mutant, designated DL42.107d, that was unable to utilize heme:hemopexin as a source of heme for growth (Hanson et al., 1992). More recently, nucleotide sequence analysis by the inventors proved that this particular linker insertion was located within the hxuA gene in the recombinant plasmid pHX1-6 (Cope et al., 1994). A cat cartridge with NotI ends was ligated into this site, yielding the mutated plasmid pHX1-61 (FIG. 1). This plasmid was then linearized by digestion with BamHI and used to transform the wild-type *Hi*b strain DL42. Chloramphenicol-resistant transformants were screened for their ability to express the HxuA protein by using the HxuA-specific Mab 4C11 as a probe in the colony blot-RIA. Transformants unreactive with this Mab were also shown to be unable to bind heme:hemopexin in the colony blot system and one of these, designated DL42.61, was selected for further study. Southern blot analysis confirmed that the proper allelic exchange had occurred in DL42.61 (FIG. 3, Panel 5 and Panel 6).

EXAMPLE IX

Expression of Hxu Proteins by Wild-Type and Mutant Strains

1. Preparation of Culture Supernatants and Cells for Detection of Heme:Hemopexin-Binding Activity Logarithmic phase cultures (25 ml) of *H. influenzae* grown in BHI/NAD medium containing heme and *E. coli* grown in LB medium were harvested by centrifugation at 12,000×g for 10 min. The cell pellet was suspended in 1 ml of pH 7.4 phosphate-buffered saline (PBS) and then 0.5 ml of 3×-concentrated digestion buffer (Patrick et al., 1987) was added and the suspension was incubated at 37° C. for 15 min. This whole cell lysate was stored at −20° C. until used. The supernatant fluid from this first centrifugation step was decanted and then centrifuged at 200,000×g for 1 hr. The final supernatant fluid was drawn off without disturbing the membrane pellet and was concentrated 40-fold by the use of a Centriprep concentrator (Amicon Inc., Beverly, Md.).

The concentrated supernatant was shown to be free of contaminating outer membrane blebs or fragments by Western blot analysis using a monoclonal antibody (9F5) reactive with the P2 major outer membrane protein of *Hi*b (Cope et al., 1990). The concentrated supernatant was then precipitated with 10% (vol/vol) trichloroacetic acid, washed in acetone, and suspended in 50 $\mu$l of digestion buffer (Gulig et al., 1984). After incubation at 37° C. for 15 min, this material was stored at −20° C. until used.

2. Detection of Heme:Hemopexin-Binding Activity

Purified heme:human hemopexin (Hanson et al., 1992) was radioiodinated to a specific activity of 40 $\mu$Ci/$\mu$g protein by using Iodo-Beads (Pierce Chemical Co., Rockford, Ill.) and a protocol provided by the manufacturer.

(i) Detection of heme:hemopexin-binding activity expressed by bacterial cells was accomplished by a colony blot method in which bacterial colony paste was spotted onto a Whatman No. 40 filter paper with an applicator stick and dried at 37° C. for 1 hr. The filter was then incubated for 1 hr with gentle agitation in PBS containing 0.05% (vol/vol) Tween-20 (Sigma Chemical Co., St. Louis, Mo.) and 0.1% (wt/vol) bovine serum albumin (Sigma) (PBS-T-BSA). Next, the filter was incubated in PBS-T-BSA containing 0.5 $\mu$Ci of radioiodinated heme:hemopexin overnight at 4° C. The next morning, the filter was washed three times (15 min each) in PBS-T-BSA and then dried and processed for autoradiography.

(ii) Detection of heme:hemopexin-binding activity in culture supernatant fluids and whole cell lysates was accomplished by use of a direct binding assay that was a modification of a Western blot method (Hanson et al., 1992). Briefly, quantities of culture supernatant and whole cell lysate equivalent to 0.5 ml of the original culture were subjected to sodium dodecyl sulfate (SDS)-polyacrylamide gel electrophoresis (PAGE) as described (Gulig et al., 1984) except that a Mini-Protean II system (Bio-Rad, Hercules, Calif.) with a 10% (wt/vol) polyacrylamide separating gel was used. The gel-resolved proteins were electrophoretically transferred to nitrocellulose using a Mini-Protean II Trans-Blot system (Bio-Rad). The nitrocellulose membrane was then incubated in PBS-T-BSA for 1 hr at 4° C. after which it was transferred to PBS-T-BSA containing 1 $\mu$Ci of radioiodinated heme:hemopexin. After overnight incubation at 4° C., the membrane was washed twice (15 min each) in PBS-T-BSA, dried, and processed for autoradiography.

3. Western Blot Analysis

Detection of the reactivity of murine Mabs with *H. influenzae* antigens in Western blot analysis was accomplished as described by Kimura et al. (1985).

4. Results

Expression of HxuA by these strains was detected by use of the direct heme:hemopexin-binding assay in which culture supernatants were processed by SDS-PAGE, transferred to nitrocellulose, and incubated with radioiodinated heme-:hemopexin (FIG. 4). Expression of HxuB and HxuC was detected by Coomassie blue staining of proteins present in outer membrane vesicles, as resolved by SDS-PAGE (FIG. 5, Panel 1). HxuB was also identified by Western blot analysis using the HxuB-specific Mab 2B7 (FIG. 5, Panel 2).

The wild-type parent strain DL42 expressed the HxuA protein (FIG. 4, Panel 1, lane A) as well as both HxuB (FIG. 5, Panel 1 and Panel 2, lane A) and HxuC (FIG. 5, Panel 1, lane A). Insertion of the cat cartridge into the hxuC gene in the mutant strain DL42.63 eliminated detectable expression of HxuC (FIG. 5, Panel 1, lane B). Barely detectable amounts of HxuB (FIG. 5, Panel 1 and Panel 2, lane B) and HxuA (FIG. 4, Panel 1, lane B) were expressed by this hxuC mutant. The hxuB mutant strain DL42.62 could still express wild-type levels of the HxuC protein (FIG. 5, Panel 1, lane D) but could express neither the HxuB molecule (FIG. 5, Panel 1 and Panel 2, lane D) nor HxuA (FIG. 4, Panel 1, lane C). Finally, the hxuA mutant DL42.61 expressed both HxuC (FIG. 5, Panel 1, lane F) and HxuB (FIG. 5, Panel 1 and Panel 2, lane F) but did not express HxuA (FIG. 4, Panel 1, lane D).

EXAMPLE X

Utilization of Heme and Heme:Carrier Protein Complexes

The wild-type parent strain DL42 was able to utilize free heme as well as all of the heme:protein complexes tested (Table 3). The hxuA mutant DL42.61 was able to utilize free heme and all of the other heme compounds except heme-:hemopexin (Table 3), as would be expected from the previous demonstration that expression of the HxuA protein is essential for utilization by *Hi*b strain DL42 of heme bound to hemopexin (Hanson et al., 1992). The heme utilization phenotype of the hxuB mutant strain DL42.62 was identical to that of the hxuA mutant (Table 3); the inability of this mutant to utilize heme bound to hemopexin correlated with the lack of expression of HxuA by this mutant (FIG. 4, Panel 1, lane D).

The hxuC mutant DL42.63 was unable to utilize heme-:hemopexin (Table 3). However, the hxuC mutant was also unable to utilize free heme (10 μg/ml) for growth (Table 3). This mutant could still utilize both hemoglobin and hemoglobin:haptoglobin (Table 3). More extensive testing revealed that the hxuC mutant formed single colonies when heme was provided at a concentration of 50 μg/ml. During growth in broth-based media containing heme at 10 μg/ml, both the wild-type parent strain and the hxuC mutant grew at similar rates. However, the mutant was unable to grow when the heme concentration in the broth medium was reduced to 0.1 μg/ml whereas the wild-type strain grew readily at this same heme concentration. Therefore, the hxuC mutation adversely affected the ability of strain DL42 to utilize low levels of free heme, in a manner similar to the inability of *H. influenzae* tonB mutants to utilize free heme at low concentrations (Jarosik et al., 1994).

To confirm directly the role of the HxuC protein in the utilization of low levels of free heme, a recombinant plasmid was constructed which contained only the hxuC gene. To accomplish this, the 2.9 kb AlwnI fragment containing the wild-type hxuC gene was excised from pHX1-60 and, after the addition of PstI linkers, was ligated into the PstI cloning site within pGJB103, yielding the recombinant plasmid pHX1-64. The hxuC mutant was transformed with this plasmid, yielding the transformant strain DL42.63(pHX1-64) which overexpressed HxuC (FIG. 6, lane B). The presence of the wild-type hxuC gene in trans permitted growth of the transformant strain DL42.63(pHX1-64) on solidified media containing heme at 10 μg/ml (Table 3). The presence of this plasmid did not allow DL42.63(pHX1-64) to utilize heme:hemopexin (Table 3).

EXAMPLE XI

Genetic Restoration of Free Heme and Heme:Hemovexin Utilization

The recombinant plasmid pHX1-60 containing the wild-type hxuA, hxuB, and hxuC genes was digested with BamHI, yielding a 14 kb fragment containing the entire *Hi*b DL42 DNA insert and flanking DNA from the vector. This large DNA fragment was used to transform the chloramphenicol-resistant hxuA, hxuB, and hxuC mutants and the resultant transformants were all screened for reactivity with the HxuA-specific Mab 4C11. Those transformants that bound Mab 4C11 were also tested for their sensitivity to chloramphenicol, to identify those transformants in which allelic exchange had eliminated the mutated gene containing the cat cartridge.

One chloramphenicol-sensitive and Mab 4C11-reactive transformant from each of the three transformation experiments involving the hxuA, hxuB, and hxuC mutants was selected for further testing and designated DL42.61.T, DL42.62.T, and DL42.63.T, respectively. Southern blot analysis confirmed the occurrence of proper allelic exchange in each of these transformants (FIG. 3, Panel 1, Panel 2, Panel 3, Panel 4, Panel 5, Panel 6, lane C). Each of these transformants also exhibited the wild-type phenotype with regard to outer membrane protein profile (FIG. 5, lanes C, E, and G) and utilization of low levels of free heme (Table 3).

EXAMPLE XII

Effect of the hxuB Mutation on Release of Soluble HxuA from *Hi*b

The HxuA protein has been shown to be released in soluble form by both *Hi*b and NT*HI* strains (Cope et al., 1994). To determine whether either of the genes immediately upstream from hxuA is involved in this process, the recombinant plasmid pSET200 containing a wild-type hxuA gene from a NT*HI* strain (cope et al., 1994) was used to transform the hxuA, hxuB, and hxuC mutants. It should be noted that this recombinant plasmid does not contain either a NT*HI* hxuB gene or a NT*HI* hxuC gene (Table 2) (Cope et al., 1994). The resultant transformants were studied for their ability to produce a soluble HxuA protein that was released into the culture supernatant.

A soluble HxuA protein was detected in the culture supernatant from the recombinant strain DL42.61(SET200) (FIG. 4, Panel 2, lane D), indicating that the NT*HI* HxuA protein was released from this hxuA mutant carrying the NT*HI* hxuA gene in trans. However, culture supernatant from the recombinant strain DL42.62(pSET200) did not contain the NT*HI* HxuA protein (FIG. 4, Panel 2, lane C), indicating that expression of the hxuB gene is apparently required for release of the HxuA protein into the culture supernatant. Similarly, the recombinant strain DL42.63 (pSET200), which expresses only very low levels of HxuB, did not release any detectable NT*HI* HxuA into its culture supernatant (FIG. 4, Panel 2, lane B).

EXAMPLE XIII hxuC and hxuB from Nontypeable *H. influenzae* (NT*HI*)

1. Bacterial Strains and Culture Conditions

Nontypeable *H. influenzae* (NT*HI*) strain TN106 has been described (Sanders et al., 1993). *H. influenzae* strains were grown in Brain Heart Infusion (BHI) broth containing NAD (10 μg/ml) and a heme source. Heme sources were free heme supplied as hemin (heme chloride) at 8.5 μg/ml or Levinthal's base (i.e., horse blood extract) 10% vol/vol. *E. coli* strain RR1 (Sambrook et al., 1989) was routinely grown in LB broth (Miller, 1972). Antibiotics were added to media at the following concentrations: kanamycin, 20 μg/ml; tetracycline, 20 μg/ml.

2. Genetic Techniques

Standard genetic techniques including plasmid isolation, restriction enzyme digests, DNA modifications, and ligation reactions were performed as described (Sambrook et al., 1989; Tomb et al., 1989). Electroporation of NT*HI* strain TN106 was performed as described (Helminen et al., 1993). A genomic library was constructed from the wild-type NT*HI* strain TN106 in the shuttle vector pLS88 (Willson et al., 1989), using the EcoRI cloning site for cloning purposes.

3. Nutagenesis of TN106

NT*HI* strain TN106 was treated with N-methyl-N'-nitro-N-nitrosoguanidine (NTG) as described (Miller, 1972). Briefly, 5 ml of NT*HI* strain TN106 was grown in BHI broth supplemented with Levinthal's base (BHIs) to mid-logarithmic phase, washed twice with 0.1M citrate buffer (pH 5.5), and resuspended in 5 ml citrate buffer. The cells were then incubated with NTG (100 µg/ml) for 30 min, washed with 0.1 M phosphate buffer (pH 7.0), and incubated in BHI-NAD broth containing 20 µg/ml protoporphyrin IX (PPIX) for 30 min at 37° C. The cells were then plated on BHI-NAD-PPIX agar plates and incubated overnight at 37° C. in a 95% air-5% $CO_2$ atmosphere. The resultant colonies were then tested for growth on BHI-NAD plates containing 8.5 µg/ml heme. A mutant, designated TN106.31, was isolated which could not grow on heme plates.

4. Complementation of the Mutation in TN106.31

In order to identify the gene(s) associated with the ability to grow on heme plates, TN106.31 was electroporated with a pLS88-based TN106 chromosomal library and the electroporation mixture was plated on BHI-NAD agar plates containing heme (8.5 µg/ml) and kanamycin. Plasmid DNA was isolated from several kanamycin-resistant transformants able to grow on the heme plates. Restriction enzyme analysis indicated all the plasmids contained a 2.4 kb EcoRI insert. Electroporation of TN106.31 with one plasmid, designated pGJ400, indicated the ability to grow on heme plates was plasmid-associated and this plasmid was selected for further study.

5. Sequencing of the NT*HI* Strain TN106 hxuC and hxuB homologs

The 2.4 kb EcoRI insert of pGJ400 was cloned into pBluescriptII SK+(Strategene, La Jolla, Calif.) and the nucleotide sequence of both strands was determined by performing dideoxy sequencing protocols (Sanger et al., 1977) using nested deletions. Sequence analysis indicated this fragment possessed 2 partial ORFs. The first partial ORF encoded a polypeptide which exhibited high amino acid identity to the carboxy-terminus half of the HxuC protein of *H. influenzae* type b (*Hi*b) (Cope et al., 1994).

To obtain the nucleotide sequence of the 5'-end of the NT*HI* hxuC gene, *E. coli* strain RR1 cells transformed with a plasmid-based TN106 chromosomal library (cloned into the PstI site of PBR322) were screened by in situ colony hybridization (Sambrook et al., 1989) using a 1.2 kb NheI-EcoRI consisting of the 5'-end of the *Hi*b hxuC gene. This resulted in the isolation of a plasmid, designated pGJ803.9, which contained a PstI 3.9 kb insert. A 2.5 kb PstI-HindIII fragment containing the 5'-end of the NT*HI* hxuC gene was subcloned into pBluescriptII KS+(Strategene, La Jolla, Calif.) the nucleotide sequence was determined as described above using nested deletions.

Immediately downstream (90 nt) of the first partial ORF was a second partial ORF which encoded a nearly complete polypeptide which exhibited high amino acid identity with the hxuB gene of *Hi*b (Cope et al., 1994) which codes for the 60 kD HxuB protein. To obtain the remaining 3'-end sequence of the NT*HI* hxuB gene, *E. coli* strain RR1 cells transformed with a plasmid-based TN106 chromosomal library cloned into the PstI site of pBR322 were screened by in situ colony hybridization (Sambrook et al., 1989) using a 2.2 kb PstI-PvgII fragment consisting of the 5'-end of the *Hi*b hxuA gene. This resulted in the isolation of a plasmid, designated pGJ86100, which contained a 14 kb insert consisting of a 3.9 kb PstI fragment and a 10.1 kb PstI fragment. Using Southern blot analysis (Sambrook et al., 1989), the 3.9 kb PstI fragments of pGJ803.9 and pGJ86100 hybridized to the 1.2 kb NheI-EcoRI hxuC fragment described above.

Western blot analysis of plasmid-encoded proteins expressed from RR1(pGJ86100) using *Hi*b HxuB-specific antiserum demonstrated the expression of the 60 kD NT*HI* HxuB protein. Using pGJ86100, the nucleotide sequence of the remainder of the NT*HI* hxuB gene was performed by double-stranded plasmid DNA sequencing of the relevant region in pGJ86100. Taken together, these efforts yielded the complete nucleotide sequences of the NT*HI* hxuC and hxuB genes.

EXAMPLE XIV

Clinical Detection of *Hi*b or NT*HI*

One contemplated clinical detection utility is the use of internal sequences from the hxuB and/or hxuC gene(s) in a PCR based detection system. The length of the sequence to be detected/amplified is contemplated to range from 50–500 bp. Southern hybridization analysis is readily performed in order to determine the DNA sequences from hxuC and/or hxuB used for primers and the DNA sequences to be detected are specific for *H. influenzae* chromosomal DNA. Also, the set or sets of primers selected reproducibly prime the synthesis of DNA fragments of the same size from different *H. influenzae* isolates. Sets of primers could be tested using a battery of known *H. influenzae* isolates and lab strains.

For detection, clinical isolate samples (i.e., sputum from lungs, secretions from middle or inner ear, cerebrospinal fluid) are obtained from a patient. The isolate is centrifuged to pellet bacteria. Alternatively, bacteria is grown on selective plates. Bacterial cells are lysed, pelleted, and a sample of the supernatant added to a PCR reaction using the *H. influenzae* specific primers. Following amplification, the products are separated via agarose gel electrophoresis and the banding patterns visualized via ethidium bromide. The presence of the DNA band fragments indicate the presence of *H. influenzae* in the clinical isolate.

EXAMPLE XV

Recombinant Expression of HxuB and HxuC Proteins

To overexpress the HxuC or HxuB proteins, DNA fragments containing either the entire hxuC or hxuB gene are cloned into an expression vector. One expression vector of choice is the pET-21(+) expression vector from Novagen (Novagen, Madison, Wis.). This vector contains a multiple restriction enzyme cloning site that situates the gene such that expression of the gene is controlled from an inducible T7 promoter. Correct orientation of the gene is determined via restriction enzyme analysis. Basal levels of expression of the HxuC or HxuB proteins are determinable via SDS-PAGE and Western blot analysis.

The plasmid constructs, are then introduced into the protein expression *E. coli* strain BL21(DE3) (Novagen). Overexpression of HxuC or HxuB is performed according to the manufacturer's (Novagen) instructions. Briefly, cell cultures containing the appropriate recombinant plasmid constructs are grown to a Klett reading of 100. IPTG is then added to a final concentration of 1 mM to induce protein expression from the T7 promoter. After 3 hours, 1 ml samples are harvested and protein induction assayed by SDS-PAGE and Western Blot analysis. Frozen pellets are stored at −70° C. following a wash with 50 mM Tris-HCl pH 8.0, 2 mM EDTA.

The isolation of the soluble and insoluble (inclusion bodies) protein fractions is performed according to the manufacturer's instructions. Briefly, thawed cell pellets are resuspended in 5ml of 50 mM Tris-HCL pH 8.0, 2 mM EDTA. Lysozyme is added to this suspension to 100 μg/ml and Triton X-100 to 0.1%. After incubation at room temperature for 30 min., the suspension is sonicated and then centrifuged at 12,000 g for 15 min. The pellet (inclusion bodies) is resuspended in 1 ml PBS buffer. Both the soluble and insoluble fractions are retained and analyzed by SDS-PAGE/Western blot analysis for the HxuB and HxuC proteins. Both the soluble and insoluble fractions are stored at −70° C. Purification of the proteins is also contemplated using other pET vectors which place His-Tags on the overexpressed protein allowing for affinity column (nickel) chromatography purification.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

In addition to the patent documents listed throughout the text, the following other references, to the extent that they provide exemplary procedural or other details supplementary to those set forth herein, are specifically incorporated herein by reference.

Adelman et al., DNA, 2:183, 1983
Alexander, "Bacterial and mycotic infections of man," The Haemophilus group, 724–741, 1965
Antibodies: A Laboratory Manual, Spring Harbor Laboratory, 1988
Barcak et al., "Genetic systems in Haemophilus influenzae," Methods Enzymol, 204:321–342, 1991
Birnboim et al., Nucl. Acids Res., 7:1513–1523, 1979
Bolivar et al., Gene, 2:95, 1977
Bonner et al., J. Mol. Biol., 81:123–135, 1973
Braun et al., "Serratia marcescens forms a new type of cytolysin," FEMS Microbiol. Lett, 100:299–306, 1992
Campbell, in Monoclonal Antibody Technology, Laboratory Techniques in Biochemistry and Molecular Biology Vol. 13, Burden and Von Knippenberg, eds. pp. 75–83, Amsterdam, Elseview, 1984
Case et al., Nucl. Acids. Res., 4:1539, 1977
Chang et al., Nature, 375:615, 1978
Chou and Fasman, Biochemistry, 13(2):222–245, 1974a
Chou and Fasman, Biochemistry, 13(2):211–222, 1974b
Chou and Fasman, Adv. Enzymol. Relat. Areas Mol. Biol., 47:45–148, 1978a
Chou and Fasman, Ann. Rev. Biochem., 47:251–276, 1978b
Chou and Fasman, Biophys. J., 26:367–384, 1979
Cohen, "Naked DNA Points Way to Vaccines," Science, 259:1691–1692, 1993.
Cope et al., "Characterization of a mutant of Haemophilus influenzae type b lacking the P2 major outer membrane protein," Infect. Immun., 58:3312–3318, 1990
Cope et al., "Effect of mutations in lipooligosaccharide biosynthesis genes on virulence of Haemophilus influenzae type b," Infect. Immun., 58:2343–2351, 1990
Cope et al., "Molecular cloning of a gene involved in lipopolysaccharide biosynthesis and virulence expression by Haemophilus influenzae type b," Mol. Microbiol., 5:1113–1124, 1991
Cope et al., "The 100 kDa heme:hemopexin-binding protein of Haemophilus influenzae: structure and localization," Mol. Microbiol., 13:863–873, 1994.
Cox et al., J. Virol. 67(9):5664–5667, 1993.
Crea et al., Proc. Natl. Acad. Sci. U.S.A, 75:5765, 1978
Devereux et al., "A comprehensive set of sequence analysis programs for the VAX," Nucleic Acids Res., 12:387–395, 1984
Eichenlaub, J. Bacteriol, 138:559–566, 1979
Evans et al., "Haemin and nicotinamide adenine dinucleotide requirements of Haemophilus influenzae and Haemophilus parainfluenzae," J. Med. Microbiol., 7:359–365, 1974
Fiers et al., Nature, 273:113, 1978
Fraser et al., Am. J. Epidemiol., 100:29–34, 1974.
Fynan et al., "DNA vaccines: Protective immunizations by parenteral, mucosal, and gene-gun inoculations," Proc. Natl. Acad. Sci. USA, 90:11478–11482, 1993.
Gefter et al., Somatic Cell Genet., 3:231–236, 1977
Goding, 1986, in Monoclonal Antibodies: Principles and Practice, 2d ed., Orlando, Fla., Academic Press, 1986, pp. 60–61, 65–66, 71–74
Goeddel et al., Nature, 281:544, 1979
Goeddel et al., Nucleic Acids Res., 8:4057, 1980
Granick and Gilder, "The porphyrin requirements of Haemophilus influenzae and some functions of the vinyl and propionic acid side chains of heme," J. Gen. Physiol., 30:1–13, 1946
Granoff and Munson, Jr., The Journal of Infectious Diseases, 153(3), 1986
Guan et al., Gene, 67:21–30, 1987
Gulig et al., "Immunogenic proteins in cell-free culture supernatants of Haemophilus influenzae type b," Infect. Immun., 44:41–48, 1984
Hannavy and Higgins, "TonB; a model for signal transduction between membranes," Biochem. Soc. Transact., 19:530–532, 1991
Hansen et al., "Cloning of the gene encoding the major outer membrane protein of Haemophilus influenzae type b," Infect. Immun., 56:2709–2716, 1988
Hansen et al., "Primary structure of the porin protein of Haemophilus influenzae type b determined by nucleotide sequence analysis," Infect. Immun., 57:1100–1107; 1989
Hansen et al., "Use of electroporation to construct isogenic mutants of Haemophilus ducreyi," J. Bacteriol., 174:5442–5449, 1992
Hanson and Hansen, "Molecular cloning, partial purification, and characterization of a haemin-binding lipoprotein from Haemophilus influenzae type b," Mol. Microbiol., 5:267–278, 1991
Hanson et al., "Identification of a genetic locus of Haemophilus influenzae type b necessary for the binding and utilization of heme bound to human hemopexin," Proc. Natl. Acad. Sci. USA, 89:1973–1977, 1992

Hanson et al., "The hbpA gene of *Haemophilus influenzae* type b encodes a heme-binding lipoprotein conserved among heme-dependent Haemophilus species," *Infect. Immun.*, 60:2257–2266, 1992

Heller and Kadner, "Nucleotide sequence of the gene for the vitamin $B_{12}$ receptor protein in the outer membrane of *Escherichia coli*," *J. Bacteriol.*, 161:904–908, 1985

Helminen et al., *Infect. Immun.*, 61:2003–2010, 1993

Herriott et al., "Defined non-growth media for stage II development of competence in *Haemophilus influenzae*," *J. Bacteriol.*, 101:517–524, 1970

Hess et al., *J. Adv. Enzyme Reg.*, 7:149, 1968

Hickman et al., "Isolation of a hemoglobin binding protein from *Haemophilus influenzae*," *Abstracts for General Meeting of the American Society of Microbiologists* 1992, B-292:78, 1993

Hitzeman et al., *J. Biol. Chem.*, 255:2073, 1980

Holland et al., *Biochemistry*, 17:4900, 1978

Holland et. al., *Infect Immun.*, 60(7):2986–91, 1992

Hunkapiller et al., "Isolation of microgram quantities of proteins from polyacrylamide gels for amino acid sequence analysis," *Methods Enzymol.*, 91:227–236, 1983

Itakura et al., *Science*, 198:1056, 1977

Jameson and Wolf, *Compu. Appl. Biosci.*, 4(1):181–6, 1988

Jarosik et al., "A functional tonB gene is required for both utilization of heme and virulence expression by *Haemophilus influenzae* type B," *Infect. Immun.*, 62:2470–2477, 1994

Jones, *Genetics*, 85:12, 1977

Kimura et al., "A minor high-molecular-weight outer membrane protein of *Haemophilus influenzae* type b is a protective antigen," *Infect. Immun.*, 47:253–259, 1985

Koebnik et al., "The TonB protein of *Yersininia enterocolitica* and its interactions with TonB-box proteins," *Mol. Gen. Genet.*, 237:152–160, 1993

Kohler and Milstein, *Nature*, 256:495–497, 1975

Kohler and Milstein, *Eur. J. Immunol.*, 6:511–519, 1976

Kyte and Doolittle, *J. Mol. Biol.*, 157:105–132., 1982

Lee, "Isolation of an outer membrane hemin-binding protein of *Haemophilus influenzae* type b," *Infect. Immun.*, 60:810–816, 1992

Litwin and Calderwood, "Role of iron in regulation of virulence genes," *Clin. Microbiol. Rev.*, 6:137–149, 1993

Marmur and Doty, *J. Mol. Biol.*, 5:109, 1962

Matsudaira, "Sequence from picomole quantities of proteins electroblotted polyvinylidene difluoride membranes," *J. Biol. Chem.*, 262:10035–10038, 1987

McConaughy et al., *Nucl. Acid Reassociation*, 8:3789, 1969

Messing et al. (1981) Third Cleveland Symposium on Macromolecules and Recombinant DNA, Editor A. Walton, Elsevier, Amsterdam Miller, *Experiments in Molecular Genetics*, Cold Spring Harbor Laboratory, 1972

Morton et al., "Expression of the *Haemophilus influenzae* transferrin receptor is repressible by hemin but not elemental iron alone," *Infect. Immun.*, 61:4033–4037, 1993

Murphy et al., *J. Infect. Dis.*, 152:1300–1307, 1985

Nagai and Thogersen, *Meth. Enzymol.*, 153:461–487, 1987

Nakamura et al., Enzyme Immunoassays: Heterogeneous and Homogeneous Systems, Chapter 27, 1987.

Nau and Konisky, "Evolutionary relationship between the TonB-dependent outer membrane transport proteins: nucleotide and amino acid sequences of the *Escherichia coli* colicin I receptor gene," *J. Bacteriol.*, 171:1041–1047, 1989

Otto et al., "Transferrins and heme-compounds as iron sources for pathogenic bacteria," *Crit. Rev. Microbiol.*, 18:217–233, 1992

Patrick et al., "Antigenic characterization of the oligosaccharide portion of the lipooligosaccaride of nontypable *Haemophilus influenzae*," *Infect. Immun.*, 55:2902–2911, 1987

Poole et al., "Molecular characterization of the hemolysin determinant of *Serratia marcescens*," *J. Bacteriol.*, 170:3177–3188, 1988

Postle, "TonB and the Gram-negative dilemma," *Mol. Microbiol.*, 4:2019–2025, 1990

Robertson et al., "Monoclonal antibodies directed against a cell surface-exposed outer membrane protein of *Haemophilus influenzae* type b," *Infect. Immun.*, 36:80–88, 1982

Sambrook et al., "Molecular cloning: A laboratory manual," Cold Spring Harbor Laboratory Press, 1989

Sanger et al., *PNAS USA*, 74:5463–5467, 1977

Schiebel et al., "Subcellular location and unique secretion of the hemolysin of *Serratia marcescens*," *J. Biol. Chem.*, 264:16311–16320, 1989

Schryvers, *J. Microbiology*, 2:467–472, 1988

Shine and Dalgarno, "Determinant of cistron specificity in bacterial ribosomes," *Nature*, 254:34–38, 1975

Shenep et al., *Infect. Immun.*, 42:257–263, 1983

Sherry et al., *Dev. Pharmacol. Ther.*, 12(4):188–99, 1989

Sjostrom et al., "Signal peptide amino acid sequences in *Escherichia coli* contain information related to final protein localization: A multivariate data analysis," *EMBO J.*, 6:823–831, 1987

Stevenson et. al., *Infect. Immun.*, 60(6):2391–6, 1992

Stinchcomb et al., *Nature*, 282:39, 1979

Stojiljkovic and Hantke, "Hemin uptake system of *Yersinia enterocolitica*: similarities with other TonB-dependent systems in Gram-negative bacteria," *EMBO J.*, 11:4359–4367, 1992

Stull, "Protein sources of heme for *Haemophilus influenzae*," *Infect. Immun.*, 55:148–153, 1987

Stuy and Walter, Effect of glycerol on plasmid transfer in genetically competent *Haemophilus influenzae*"," *Mol. Gen. Genet.*, 203:296–299, 1986

Stuyve et al., "Carboxyterminal phenylalanine is essential for the correct assembly of a bacterial outer membrane protein," *J. Mol. Biol.*, 218:141–148, 1991

Tabor and Richardson, *Proc. Natl. Acad. Sci.*, 82:1074–1078, 1985

Tang et al., *Nature*, 356:152–154, 1992.

Tiller, Jr., and R. H. Buckley, *J. Pediatrics*, 92:347–353, 1978

*Tissue Culture*, Academic Press, Kruse and Patterson, editors (1973)

Tomb et al., "Transposon mutagenesis, characterization, and cloning of transformation genes of *Haemophilus influenzae*," *J. Bacteriol.*, 171:3796–802, 1989

Tschemper et al., *Gene*, 10:157, 1980

Ulmer et al., "Heterologous Protection Against Influenza by Injection of DNA Encoding a Viral Protein," *Science*, 259:1745–1749, 1993.

Uphoff and Welch, "Nucleotide sequencing of the *Proteus mirabilis* calcium-independent hemolysin genes (hpmA and hpmB) reveals sequence similarity with the *Serratia marcescens* hemolysin genes (shlA and shlB),"*J. Bacteriol.*, 172:1206–1216, 1990 von Heijne, G., "Signal sequences: The limits of variation," *J. Mol. Biol.*, 184:99–105, 1985

Wang et al., *Proc. Natl. Acad. Sci. USA*, 90:4156–4160, 1993.

Welch, "Pore-forming cytolysins of Gram-negative bacteria," *Mol. Microbiol.*, 5:521–528, 1991

Welch et al., "The synthesis and function of the *Escherichia coli* hemolysin and related RTX exotoxins," *FEMS Microbiology Immunology*, 105:29–36, 1992

White and Granick, "Hemin biosynthesis in Haemophilus," *J. Bacteriol.*, 85:842–850, 1963

Whitton et al., *J. Virol.* 67:(1)348–352,1993.

Willson et al., *Antimicrob. Agents. Chemother.*, 33:1627–1630, 1989

Wolf et al., *Compu. Appl. Biosci.*, 4(1):187–91, 1988

Wong et al., "Identification and characterization of an iron-regulated hemopexin receptor in *Haemophilus influenzae* type b," *Infect. Immun.*, 62:48–59, 1994

Zollinger et al., *J. Clinical Investigation*, 63:836–848, 1979

Zollinger et al., *J. Infectious Diseases*, 137:728–739, 1978

---

What is claimed is:

1. A DNA segment comprising a sequence region encoding about 15 to about 50 amino acids from SEQ. ID NO:2, wherein said DNA segment is isolated substantially away from other naturally-occurring genes.

2. The DNA segment of claim 1, wherein the contiguous amino acid sequence is encoded by position 112 to position 2286 of SEQ ID NO:1.

3. The DNA segment of claim 1, wherein said sequence region comprises from about 20 to about 30 amino acids from SEQ ID NO:2.

4. The DNA segment of claim 1, positioned under the control of a promoter.

5. The DNA segment of claim 1, further defined as a recombinant vector.

6. A DNA segment encoding an isolated nontypeable *H. influenzae* (NT*HI*) hxuC polypeptide.

7. The DNA segment of claim 6, positioned under the control of a promoter.

8. The DNA segment of claim 6, further defined as a recombinant vector.

9. A DNA segment comprising a sequence region encoding about 15 to about 50 amino acids from SEQ ID NO:3, wherein said DNA segment is isolated substantially away from other naturally-occurring genes.

10. The DNA segment of claim 9, wherein the contiguous amino acid sequence is encoded by position 2364 to position 4058 of SEQ ID NO:1.

11. The DNA segment of claim 9, wherein said sequence region comprises from about 20 to about 30 amino acids from SEQ ID NO:3.

12. The DNA segment of claim 9, positioned under the control of a promoter.

13. The DNA segment of claim 9, further defined as a recombinant vector.

14. A DNA segment encoding an isolated nontypeable *H. influenzae* (NT*HI*) hxuB polypeptide.

15. The DNA segment of claim 14, positioned under the control of a promoter.

16. The DNA segment of claim 14, further defined as a recombinant vector.

17. A DNA segment consisting of a contiguous nucleic acid sequence of 22 to about 50 contiguous nucleotides from SEQ ID NO:1.

18. The DNA segment of claim 17, positioned under the control of a promoter.

19. The DNA segment of claim 17, further defined as a recombinant vector.

20. A DNA segment encoding an isolated NT*HI* hxuC and NT*HI* hxuB gene polypeptides.

21. The DNA segment of claim 20, comprising the nucleic acid sequence of SEQ ID NO:6.

22. The DNA segment of claim 20, positioned under the control of a promoter.

23. The DNA segment of claim 20, further defined as a recombinant vector.

24. An isolated nucleic acid segment characterized as:
  (a) a nucleic acid segment comprising at least 22 contiguous nucleotides that have the same sequence as, or are complementary to, 22 contiguous nucleotides of SEQ ID NO:6.

25. The nucleic acid segment of claim 24, wherein the segment comprises a sequence region of at least about 30 contiguous nucleotides from SEQ ID NO:6 or the complement thereof.

26. The nucleic acid segment of claim 25, wherein the segment comprises a sequence region of at least about 50 contiguous nucleotides from SEQ ID NO:6 or the complement thereof.

27. The nucleic acid segment of claim 26, wherein the segment comprises a sequence region of at least about 100 contiguous nucleotides from SEQ ID NO:6 or the complement thereof.

28. The nucleic acid segment of claim 27, wherein the segment comprises up to 2,000 basepairs of SEQ ID NO:6 or the complement thereof.

29. The nucleic acid segment of claim 28, wherein the segment comprises up to 3,000 basepairs of SEQ ID NO:6 or the complement thereof.

30. The nucleic acid segment of claim 29, wherein the segment comprises up to 5,000 basepairs of SEQ ID NO:6 or the complement thereof.

31. The nucleic acid segment of claim 24, further defined as a DNA segment.

32. The nucleic acid segment of claim 24, further defined as a RNA segment.

33. A recombinant host cell encodes a DNA segment that comprises an isolated nontypeable *H. influenzae* (NT*HI*) hxuC polypeptide.

34. The recombinant host cell of claim 33, further defined as a bacterial host cell.

35. The recombinant host cell of claim 34, wherein the bacterial host cell is *E. coli, H. influenzae* type b or nontypeable *H. influenzae.*

36. The recombinant host cell of claim 35, wherein the bacterial host cell is *H. influenzae* Rd strain DB117.

37. The recombinant host cell of claim 32, wherein the DNA segment is introduced into the cell by means of a recombinant vector.

38. A method of using a DNA segment that includes a sequence region encoding at least about 15 consecutive amino acids of an isolated nontypeable *H. influenzae* (NT*HI*) hxuC or hxuB gene, wherein said consecutive amino acids are an antigenically functional equivalent of a HxuC or HxuB protein, comprising:
 (a) providing a recombinant vector comprising a DNA segment encoding about 15 consecutive amino acids of nontypeable *H. influenzae* (NT*HI*) HxuC or HxuB positioned under the control of a promoter;
 (b) introducing said recombinant vector into a recombinant host cell; and
 (c) culturing the recombinant host cell under conditions effective to allow expression of the antigenically functional equivalent protein or peptide.

39. The method of claim 38, wherein the DNA segment comprises an isolated NT*HI* hxuC gene.

40. The method of claim 38, wherein the DNA segment comprises an isolated NT*HI* hxuB gene.

41. The method of claim 38, wherein the DNA segment comprises an isolated NT*HI* hxuC and hxuB gene.

42. A recombinant host cell encodes a DNA segment that comprises an isolated nontypeable *H. influenzae* (NT*HI*) hxuB polypeptide.

43. A recombinant host cell comprising a DNA segment that encodes isolated nontypeable *H. influenzae* (NT*HI*) hxuC and hxuB polypeptides.

44. A recombinant host cell comprising a DNA segment that comprises an isolated *H. influenzae* type b (*Hi*b) hxuC sequence encoding about 15 amino acids of SEQ ID NO:2 positioned under the control of a promoter active in said host cell.

45. The recombinant host cell of claim 44, wherein the DNA segment encodes the entire amino acid sequence from SEQ ID NO:2.

46. A recombinant host cell comprising a DNA segment that comprises an isolated *H. influenzae* type b (*Hi*b) hxuB sequence encoding about 15 amino acids of SEQ ID NO:3 positioned under the control of a promoter active in said host cell.

47. The recombinant host cell of claim 46, wherein the DNA segment encodes the entire amino acid sequence from SEQ ID NO:3.

48. A recombinant host cell comprising DNA segments that encode isolated *H. influenzae* type b (*Hi*b) hxuC and huxB polypeptides, wherein at least one of said DNA segments is positioned under the control of a promoter active in said host cell.

49. An isolated nucleic acid segment consisting of 22 to 2000 contiguous nucleotides that have the same sequence as, or are complementary to, 22 to 2000 contiguous nucleotides of SEQ ID NO:1.

50. The nucleic acid segment of claim 49, wherein said segment consists of a sequence region of 22 contiguous nucleotides from SEQ ID NO:1 or the complement thereof.

51. The nucleic acid segment of claim 49, wherein said segment consists of a sequence region of about 30 contiguous nucleotides from SEQ ID NO:1 or the complement thereof.

52. The nucleic acid segment of claim 49, wherein said segment consists of a sequence region of about 50 contiguous nucleotides from SEQ ID NO:1 or the complement thereof.

53. The nucleic acid segment of claim 49, wherein said segment consists of a sequence region of about 100 contiguous nucleotides from SEQ ID NO:1 or the complement thereof.

54. A method of using a DNA segment that includes an isolated *H. influenzae* type b (*Hi*b) hxuC or hxuB gene, wherein said consecutive amino acids are an antigenically functional equivalent of a HxuC or HxuB protein, comprising:
 (a) providing a recombinant vector comprising a DNA segment encoding about 15 consecutive amino acids of *H. influenzae* type b (*Hi*b) HxuC or HxuB positioned under the control of a promoter;
 (b) introducing said recombinant vector into a recombinant host cell;
 (c) culturing the recombinant host cell under conditions effective to allow expression of the antigenically functional equivalent protein or peptide.

55. The method of claim 54, wherein the DNA segment comprises an isolated *Hi*b hxuC gene.

56. The method of claim 54, wherein the DNA segment comprises an isolated *Hi*b hxuB gene.

57. The method of claim 54, wherein the DNA segment comprises an isolated *Hi*b hxuC and huxB gene.

58. A recombinant host cell comprising a DNA segment that comprises a nucleic acid sequence encoding a contiguous amino acid sequence of about 15 amino acids from SEQ ID NO:7.

59. The recombinant host cell of claim 58, wherein the DNA segment encodes about 15 to about 50 amino acids from SEQ ID NO:7.

60. The recombinant host cell of claim 58, wherein the DNA segment comprises from position 727 to position 2871 of SEQ ID NO:6.

61. The recombinant host cell of claim 58, wherein the DNA segment encodes about 20 to about 30 amino acids from SEQ ID NO:7.

62. The recombinant host cell of claim 58, wherein the DNA segment encodes a protein of about 715 amino acids in length.

63. A DNA segment comprising a nucleic acid sequence encoding a a contiguous amino acid sequence of about 15 amino acids from SEQ ID NO:7.

64. The DNA segment of claim 58, wherein the contiguous amino acid sequence is from about 15 to about 50 contiguous amino acids from SEQ ID NO:7.

65. The DNA segment of claim 58, wherein the contiguous amino acid sequence is encoded by position 727 to position 2871 of SEQ ID NO:6.

66. The DNA segment of claim 58, wherein the contiguous amino acid sequence is from about 20 to about 30 amino acids from SEQ ID NO:7.

67. The DNA segment of claim 58, wherein the DNA segment encodes a protein of about 715 amino acids in length.

68. A DNA segment comprising a nucleic acid sequence encoding a a contiguous amino acid sequence of about 15 amino acids from SEQ ID NO:8.

69. The DNA segment of claim 63, wherein the contiguous amino acid sequence is from about 15 to about 50 amino acids from SEQ ID NO:8.

70. The DNA segment of claim 63, wherein the contiguous amino acid sequence is encoded by position 2957 to position 4648 of SEQ ID NO:6.

71. The DNA segment of claim 63, wherein the contiguous amino acid sequence is from about 20 to about 30 amino acids from SEQ ID NO:8.

72. The DNA segment of claim 63, wherein the DNA segment encodes a protein of about 564 amino acids in length.

73. A recombinant host cell comprising a DNA segment that comprises a nucleic acid sequence encoding a contiguous amino acid sequence of about 15 amino acids from SEQ ID NO:8.

74. The recombinant host cell of claim 68, wherein the DNA segment encodes about 15 to about 50 amino acids from SEQ ID NO:8.

75. The recombinant host cell of claim 68, wherein the DNA segment comprises position 2957 to position 4648 of SEQ ID NO:6.

76. The recombinant host cell of claim 68, wherein the DNA segment encodes about 20 to about 30 amino acids of SEQ ID NO:8.

77. The recombinant host cell of claim 68, wherein the DNA segment encodes a protein of about 564 amino acids in length.

* * * * *

UNITED STATES PATENT AND TRADEMARK OFFICE
CERTIFICATE OF CORRECTION

PATENT NO. : 6,020,154
DATED : February 1, 2000
INVENTOR(S) : Eric J. Hansen et al.

Page 1 of 1

It is certified that error appears in the above-identified patent and that said Letters Patent is hereby corrected as shown below:

Column 81,
Line 2, please delete the second instance of "a".

Column 35,
Line 54, please delete ";4,596,792; and 4,578,770".

Column 79,
Line 4, please delete "a" and insert therefor --an--.
Line 5, please delete "encodes" and insert therefor --encoding--.
Line 22, please delete "a" and insert therefor --an--.
Line 39, please delete "encodes" and insert therefor --encoding--.

Column 80,
Line 20, please delete "a" and insert therefor --an--.
Line 54, please delete the second instance of "a".

Signed and Sealed this

Thirty-first Day of July, 2001

*Attest:*

Nicholas P. Godici

NICHOLAS P. GODICI
*Attesting Officer*  *Acting Director of the United States Patent and Trademark Office*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 4061 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

```
TTTACGCAAT TAAATGCAAA TGATTATAAA TAAACCAATT GATTATTATT GTAATCATCG      60

TTATTATTAT CGCCATTCTC CTCTTTTTAA TTATTACAAT AAGGAAAACA GATGCGATTT     120

TCTAAACTTT CCCTTGCAAT TGCAACAACC TTAGTGACAG CAAATGCGCT AGCGCAATCC     180

GTTGAATTAG ACTCTATCAA CGTTATTGCG ACACGAGATC CAAGTAGGTT TGCTTATACG     240

CCAGAAAAAC AATCTAAAGA TAGTCTTCTT TCCAAGCAAG CCACTAGTGT TGCAGCAGCG     300

TTAGAAGACA TTCCCAATGT TGATATTAGA GGCGGTTCAA GAAGCATTGC TCAAAAACCT     360

AATATTCGAG GGTTAAGTGA TAATCGTGTT GTGCAAGTCA TTGATGGCGT GAGACAAAAT     420

TTTGATTTAG CACATAGAGG TTCTTATTTT CTTCCAATGT CACTCATCCA AGAAATTGAA     480

GTAATCAAAG GACCAAGTAG CTCCTTATGG GGTAGCGGTG CATTGGGTGG TGTTGTGGCA     540

ATGCGTACGC CAAATGCTTT GGACTTATTG AAAAATAATG ACAAATTCGG AGTTAAAATT     600

CGCCAAGGTT ATCAAACTGC TAATAATTTA TCGGAAAGGG ATGTTTCTGT ATTTGCGGCA     660

AATGACAAAT TCGATGTTCT TATTAGTGGT TTCTATAATA ATGCGGATAA TTTACGCACT     720

GGTAAAGGCA ATAAGCTGAA TAATACCGCC TATAAACAGT TTGGGGGCTT AGCAAAATTC     780

GGTTGGCAAA TTAATGATGC TAACCGCGTG GAATTATCCC ACCGCGAAAC TCGTTTTAAA     840

CAAACAGCAC CAAGCAATAA TGAGGTGGAA AACGAACTTA CCAATGAACA AATTACAGAT     900

CAAATCGAG AGTTCCACAA ACCAAACAAC GGTTCTCCAC CGAAAGCCAA ACCATCACAA     960

GAAGAGTTTT ACTCTGGCGT GAAAACACGT TTTGGTAGTG TCAGTTATTT AACTGATCAA    1020

CAAATTCCTG ATCAAAGCAC GGTATTTAAC TATTATTTAA CGCCAGATAA TCCTTATCTA    1080

AATACGCATA TCGCACTGTA TAACAATAAA ACTATTGAGA AGAACAGCG TAAAGTCAGT    1140

GGTGTGAAAG ATCAGACTAA ATTGACTACC CGAGGTATAA ATTTACGTAA TTCTTCCGAA    1200

TTATCTCACA TTTCCTTTGT TTATGGGGTG GATTATATGC GAGATAAAAT CCGTACCGAA    1260

CGAGGCACAA ACAATAAAGA TGCGCAGTTT CGAGCGGACC CCTATAATGC GAATTCAAAC    1320

ACTACAGGCG TTTATTTAAT CGCCCATATT CCGCTATTTG GGGAAAAATT GCTACTTTCG    1380

CCAAGTGTAC GTTATGACCA CTACGATACC TCAAGTAAAA CTGTAAAATA CAAGGATAAT    1440

CATTTATCTC CTGCCACAAA ATTAACTTGG ATAGTGACCA ATTGGTTAGA TTTTACTGCC    1500

AAATATAATG AAGCTTTCCG AGCACCATCT ATGCAAGAGC GGTTTGTCAG TGGTTCGCAC    1560
```

```
TTTGGGACAA GTATTCTAGG GCGAAATGAA ATCAATAAAT TTGTAGCAAA TCCAAATTTG    1620

CGCCCTGAAA CAGCGAAAAA TAAAGAAATT ACCGCAAATC TACATTTTGA TAGTCTGTTT    1680

AAACAAGGCG ATAAATTCAA AATTGAAGCG ACTTATTTCC GTAATGATGT GAAAGATTTT    1740

ATTAACTTAA AAATATTTAA TGATGCAAAG ACAAATACAA ATGCAAGTGC AAGTGCAGGT    1800

GCAGGTGCAG GTGCAAATCC AAATGGAGCA TTGTTGCCAA CAAAATCCCA GTATCAAAAC    1860

ATAACTAATG CCCGTTTAAG CGGTATTGAA TTGCAAGCTC AATACCAAAC AGAACGTTTA    1920

ACACTGTTTA CTAACTATGG CAGCACCAAA GGTAAAGATA AGATAGTGG CGAAGCTTTA     1980

TCAAACATTG CCGCAAGCAA AATCGGCGTA GGGGTAAATT ATGCTTTAGT AAAAGACAAA    2040

TTCACGGTGG GAGCGACAGT AACCCATTAC GCTGCTCAAC GCCGAGTGCC TAAAGATCAT    2100

AGTGTTACCT ACCCAAGTTA TATACTGACC GATCTTCGTG CTACCTATGC ACCATTAAAA    2160

GGCGAATGGA AAAACCTGCG TTTAGATTTT GCGCTGGAAA ACTTGTTTGA TAGAAAATAT    2220

CAACCCGCAT TTAGTTTAAT GGAAGGCACT GGTCGTAATG CGAAAATTAG TGCGGTTTAT    2280

AGCTTCTAAA TTTACTTTGG AAAACGCCCT AAAGCTGTTT TCCCTCAATT TTTGTAATTT    2340

TATCAATTAA TAGGACATAA GGAATGAAAA TGAGACCTCG TTATTCTGTT ATTGCAAGTG    2400

CGGTCAGTTT AGGCTTTGTT TTGAGTAAAT CAGTGATGGC ATTAGGTCAG CCAGATACTG    2460

GATCATTGAA CCGTGAACTA AACAACGTC AAATTCAATC AGAAGCCAAA CCTAGTGGCG      2520

AATTATTTAA TCAAACGGCA AATTCGCCTT ATACTGCACA GTATAAACAA GGACTGAAAT    2580

TTCCACTTAC GCAAGTACAG ATTTTAGATC GAAACAATCA AGAAGTCGTC ACAGACGAGC    2640

TTGCACATAT TTTAAAAAAT TATGTAGGAA AAGAGGTATC GCTGTCAGAT TTAAGTAATT    2700

TAGCAAATGA GATCAGCGAA TTTTATCGTC ATAATAATTA TTTAGTGGCA AAAGCGATTT    2760

TACCACCGCA GGAAATTGAG CAAGGTACGG TAAAAATTCT GTTACTCAAA GGTAATGTGG    2820

GCGAAATACG CTTGCAAAAT CACAGCGCAT TAAGCAATAA ATTTGTATCC CGTCTCTCTA    2880

ATACAACAGT AAATACGTCC GAATTTATTT TGAAAGATGA GTTAGAAAAA TTTGCTTTAA    2940

CAATAAATGA TGTTCCAGGG GTAAATGCTG GTTTGCAACT CTCCGCAGGC AAAAAAGTCG    3000

GCGAAGCGAA TTTACTGATT AAGATTAACG ATGCAAAACG TTTTTCTAGT TATGTTTCAG    3060

TAGATAACCA AGGCAACAAA TATACGGGGC GTTACCGTTT GGCTGCGGGG ACAAAAGTCA    3120

GTAATTTGAA TGGCTGGGGC GATGAATTGA AACTGGATTT AATGAGTTCT AATCAGGCTA    3180

ATTTAAAAAA TGCTCGTATA GATTATTCCT CTTTAATTGA TGGTTATTCT ACGCGTTTTG    3240

GTGTAACTGC TAACTATCTC GACTACAAAT TAGGTGGTAA TTTTAAATCA TTACAATCTC    3300

AAGGGCATTC CCATACCTTA GGGGCTTATT TGTTGCACCC AACAATCCGT ACACCAAATT    3360

TTCGTTTAAG TACTAAAGTG AGCTTTAATC ATCAAAACCT TACGGATAAA CAACAAGCGG    3420

TTTATGTAAA ACAAAAACGG AAAATAAATA GTTAACTGC AGGGATTGAC GGTTCTTGGA     3480

ATCTTATTAA AGATGGGACA ACTTATTTTT CATTATCTAC CTTGTTCGGT AATTTAGCGA    3540

ATCAAACTAG TGAAAAAAAA CATAATGCAG TAGAGAATTT TCAACCAAAA TCGCATTTTA    3600

CGGTATATAA CTACCGCTTG TCTCACGAGC AAATTTTACC AAAATCTTTT GCTTTCAATA    3660

TTGGTATAAA CGGTCAGTTT GCCGATAAAA CCCTTGAAAG CTCACAGAAA ATGTTGCTTG    3720

GTGGTTTGTC TGGAGTACGT GGACATCAAG CTGGTGCGGC TTCTGTGGAT GAAGGGCATT    3780

TGATACAAAC AGAATTCAAA CATTATTTAC CAGTCTTTTC CCAAAGTGTG CTAGTTAGTT    3840

CATTGTTCTA TGACTATGGT TTGGGAAAAT ATTATAAAAA TAGCCAATTT CTCGAACAAG    3900

GCGTGAAAAA TAGCGTGAAA TTACAAAGCG TTGGTGCAGG ACTTTCTCTT TCAGATGCTG    3960
```

```
GCAGCTATGC CATCAATGTC AGTGTCGCCA AACCGCTTGA TAACAATATT AATAATGCCG      4020

ATAAACACCA ATTTTGGCTT TCTATGATTA AAACTTTCTA A                         4061
```

(2) INFORMATION FOR SEQ ID NO:2:

(i) SEQUENCE CHARACTERISTICS:
        (A) LENGTH: 725 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Arg Phe Ser Lys Leu Ser Leu Ala Ile Ala Thr Thr Leu Val Thr
 1               5                  10                  15

Ala Asn Ala Leu Ala Gln Ser Val Glu Leu Asp Ser Ile Asn Val Ile
             20                  25                  30

Ala Thr Arg Asp Pro Ser Arg Phe Ala Tyr Thr Pro Glu Lys Gln Ser
         35                  40                  45

Lys Asp Ser Leu Leu Ser Lys Gln Ala Thr Ser Val Ala Ala Ala Leu
 50                  55                  60

Glu Asp Ile Pro Asn Val Asp Ile Arg Gly Gly Ser Arg Ser Ile Ala
 65                  70                  75                  80

Gln Lys Pro Asn Ile Arg Gly Leu Ser Asp Asn Arg Val Val Gln Val
                 85                  90                  95

Ile Asp Gly Val Arg Gln Asn Phe Asp Leu Ala His Arg Gly Ser Tyr
            100                 105                 110

Phe Leu Pro Met Ser Leu Ile Gln Glu Ile Glu Val Ile Lys Gly Pro
        115                 120                 125

Ser Ser Ser Leu Trp Gly Ser Gly Ala Leu Gly Gly Val Val Ala Met
130                 135                 140

Arg Thr Pro Asn Ala Leu Asp Leu Leu Lys Asn Asn Asp Lys Phe Gly
145                 150                 155                 160

Val Lys Ile Arg Gln Gly Tyr Gln Thr Ala Asn Asn Leu Ser Glu Arg
                165                 170                 175

Asp Val Ser Val Phe Ala Ala Asn Asp Lys Phe Asp Val Leu Ile Ser
            180                 185                 190

Gly Phe Tyr Asn Asn Ala Asp Asn Leu Arg Thr Gly Lys Gly Asn Lys
        195                 200                 205

Leu Asn Asn Thr Ala Tyr Lys Gln Phe Gly Gly Leu Ala Lys Phe Gly
210                 215                 220

Trp Gln Ile Asn Asp Ala Asn Arg Val Glu Leu Ser His Arg Glu Thr
225                 230                 235                 240

Arg Phe Lys Gln Thr Ala Pro Ser Asn Asn Glu Val Glu Asn Glu Leu
                245                 250                 255

Thr Asn Glu Gln Ile Thr Asp Gln Ile Arg Glu Phe His Lys Pro Asn
            260                 265                 270

Asn Gly Ser Pro Pro Lys Ala Lys Pro Ser Gln Glu Glu Phe Tyr Ser
        275                 280                 285

Gly Val Lys Thr Arg Phe Gly Ser Val Ser Tyr Leu Thr Asp Gln Gln
290                 295                 300

Ile Pro Asp Gln Ser Thr Val Phe Asn Tyr Tyr Leu Thr Pro Asp Asn
305                 310                 315                 320

Pro Tyr Leu Asn Thr His Ile Ala Leu Tyr Asn Asn Lys Thr Ile Glu
                325                 330                 335
```

```
Lys Glu Gln Arg Lys Val Ser Gly Val Lys Asp Gln Thr Lys Leu Thr
                340                 345                 350

Thr Arg Gly Ile Asn Leu Arg Asn Ser Ser Glu Leu Ser His Ile Ser
            355                 360                 365

Phe Val Tyr Gly Val Asp Tyr Met Arg Asp Lys Ile Arg Thr Glu Arg
    370                 375                 380

Gly Thr Asn Asn Lys Asp Ala Gln Phe Arg Ala Asp Pro Tyr Asn Ala
385                 390                 395                 400

Asn Ser Asn Thr Thr Gly Val Tyr Leu Ile Ala His Ile Pro Leu Phe
                405                 410                 415

Gly Glu Lys Leu Leu Leu Ser Pro Ser Val Arg Tyr Asp His Tyr Asp
            420                 425                 430

Thr Ser Ser Lys Thr Val Lys Tyr Lys Asp Asn His Leu Ser Pro Ala
        435                 440                 445

Thr Lys Leu Thr Trp Ile Val Thr Asn Trp Leu Asp Phe Thr Ala Lys
450                 455                 460

Tyr Asn Glu Ala Phe Arg Ala Pro Ser Met Gln Glu Arg Phe Val Ser
465                 470                 475                 480

Gly Ser His Phe Gly Thr Ser Ile Leu Gly Arg Asn Glu Ile Asn Lys
                485                 490                 495

Phe Val Ala Asn Pro Asn Leu Arg Pro Glu Thr Ala Lys Asn Lys Glu
            500                 505                 510

Ile Thr Ala Asn Leu His Phe Asp Ser Leu Phe Lys Gln Gly Asp Lys
        515                 520                 525

Phe Lys Ile Glu Ala Thr Tyr Phe Arg Asn Asp Val Lys Asp Phe Ile
530                 535                 540

Asn Leu Lys Ile Phe Asn Asp Ala Lys Thr Asn Thr Asn Ala Ser Ala
545                 550                 555                 560

Ser Ala Gly Ala Gly Ala Gly Ala Asn Pro Asn Gly Ala Leu Leu Pro
                565                 570                 575

Thr Lys Ser Gln Tyr Gln Asn Ile Thr Asn Ala Arg Leu Ser Gly Ile
            580                 585                 590

Glu Leu Gln Ala Gln Tyr Gln Thr Glu Arg Leu Thr Leu Phe Thr Asn
        595                 600                 605

Tyr Gly Ser Thr Lys Gly Lys Asp Lys Asp Ser Gly Glu Ala Leu Ser
610                 615                 620

Asn Ile Ala Ala Ser Lys Ile Gly Val Gly Val Asn Tyr Ala Leu Val
625                 630                 635                 640

Lys Asp Lys Phe Thr Val Gly Ala Thr Val Thr His Tyr Ala Ala Gln
                645                 650                 655

Arg Arg Val Pro Lys Asp His Ser Val Thr Tyr Pro Ser Tyr Ile Leu
            660                 665                 670

Thr Asp Leu Arg Ala Thr Tyr Ala Pro Leu Lys Gly Glu Trp Lys Asn
        675                 680                 685

Leu Arg Leu Asp Phe Ala Leu Glu Asn Leu Phe Asp Arg Lys Tyr Gln
690                 695                 700

Pro Ala Phe Ser Leu Met Glu Gly Thr Gly Arg Asn Ala Lys Ile Ser
705                 710                 715                 720

Ala Val Tyr Ser Phe
                725
```

(2) INFORMATION FOR SEQ ID NO:3:

(i) SEQUENCE CHARACTERISTICS:
        (A) LENGTH: 565 amino acids (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met Lys Met Arg Pro Arg Tyr Ser Val Ile Ala Ser Ala Val Ser Leu
1               5                   10                  15

Gly Phe Val Leu Ser Lys Ser Val Met Ala Leu Gly Gln Pro Asp Thr
                20                  25                  30

Gly Ser Leu Asn Arg Glu Leu Glu Gln Arg Gln Ile Gln Ser Glu Ala
            35                  40                  45

Lys Pro Ser Gly Glu Leu Phe Asn Gln Thr Ala Asn Ser Pro Tyr Thr
50                      55                  60

Ala Gln Tyr Lys Gln Gly Leu Lys Phe Pro Leu Thr Gln Val Gln Ile
65                  70                  75                  80

Leu Asp Arg Asn Asn Gln Glu Val Val Thr Asp Glu Leu Ala His Ile
                85                  90                  95

Leu Lys Asn Tyr Val Gly Lys Glu Val Ser Leu Ser Asp Leu Ser Asn
                100                 105                 110

Leu Ala Asn Glu Ile Ser Glu Phe Tyr Arg His Asn Asn Tyr Leu Val
            115                 120                 125

Ala Lys Ala Ile Leu Pro Pro Gln Glu Ile Glu Gln Gly Thr Val Lys
130                 135                 140

Ile Leu Leu Leu Lys Gly Asn Val Gly Glu Ile Arg Leu Gln Asn His
145                 150                 155                 160

Ser Ala Leu Ser Asn Lys Phe Val Ser Arg Leu Ser Asn Thr Thr Val
                165                 170                 175

Asn Thr Ser Glu Phe Ile Leu Lys Asp Glu Leu Glu Lys Phe Ala Leu
            180                 185                 190

Thr Ile Asn Asp Val Pro Gly Val Asn Ala Gly Leu Gln Leu Ser Ala
            195                 200                 205

Gly Lys Lys Val Gly Glu Ala Asn Leu Leu Ile Lys Ile Asn Asp Ala
210                 215                 220

Lys Arg Phe Ser Ser Tyr Val Ser Val Asp Asn Gln Gly Asn Lys Tyr
225                 230                 235                 240

Thr Gly Arg Tyr Arg Leu Ala Ala Gly Thr Lys Val Ser Asn Leu Asn
                245                 250                 255

Gly Trp Gly Asp Glu Leu Lys Leu Asp Leu Met Ser Ser Asn Gln Ala
                260                 265                 270

Asn Leu Lys Asn Ala Arg Ile Asp Tyr Ser Ser Leu Ile Asp Gly Tyr
                275                 280                 285

Ser Thr Arg Phe Gly Val Thr Ala Asn Tyr Leu Asp Tyr Lys Leu Gly
            290                 295                 300

Gly Asn Phe Lys Ser Leu Gln Ser Gln Gly His Ser His Thr Leu Gly
305                 310                 315                 320

Ala Tyr Leu Leu His Pro Thr Ile Arg Thr Pro Asn Phe Arg Leu Ser
                325                 330                 335

Thr Lys Val Ser Phe Asn His Gln Asn Leu Thr Asp Lys Gln Gln Ala
                340                 345                 350

Val Tyr Val Lys Gln Lys Arg Lys Ile Asn Ser Leu Thr Ala Gly Ile
            355                 360                 365

Asp Gly Ser Trp Asn Leu Ile Lys Asp Gly Thr Thr Tyr Phe Ser Leu
370                 375                 380

```
Ser Thr Leu Phe Gly Asn Leu Ala Asn Gln Thr Ser Glu Lys Lys His
385                 390                 395                 400

Asn Ala Val Glu Asn Phe Gln Pro Lys Ser His Phe Thr Val Tyr Asn
            405                 410                 415

Tyr Arg Leu Ser His Glu Gln Ile Leu Pro Lys Ser Phe Ala Phe Asn
            420                 425                 430

Ile Gly Ile Asn Gly Gln Phe Ala Asp Lys Thr Leu Glu Ser Ser Gln
            435                 440                 445

Lys Met Leu Leu Gly Gly Leu Ser Gly Val Arg Gly His Gln Ala Gly
            450                 455                 460

Ala Ala Ser Val Asp Glu Gly His Leu Ile Gln Thr Glu Phe Lys His
465                 470                 475                 480

Tyr Leu Pro Val Phe Ser Gln Ser Val Leu Val Ser Ser Leu Phe Tyr
                485                 490                 495

Asp Tyr Gly Leu Gly Lys Tyr Tyr Lys Asn Ser Gln Phe Leu Glu Gln
                500                 505                 510

Gly Val Lys Asn Ser Val Lys Leu Gln Ser Val Gly Ala Gly Leu Ser
                515                 520                 525

Leu Ser Asp Ala Gly Ser Tyr Ala Ile Asn Val Ser Val Ala Lys Pro
530                 535                 540

Leu Asp Asn Asn Ile Asn Asn Ala Asp Lys His Gln Phe Trp Leu Ser
545                 550                 555                 560

Met Ile Lys Thr Phe
                565

(2) INFORMATION FOR SEQ ID NO:4:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

GGAGGTATGC TATGTATAAA TTAAATGTAA TTTCTCTTAT CATTTTGACC ACTTGCAGTG    60

GTGCGGCATA TGCCTCTACA CCGGATTTTC CACAACATCA T                      101

(2) INFORMATION FOR SEQ ID NO:5:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Met Tyr Lys Leu Asn Val Ile Ser Leu Ile Ile Leu Thr Thr Cys Ser
1               5                   10                  15

Gly Ala Ala Tyr Ala Ser Thr Pro Asp Phe Pro Gln His His
            20                  25                  30

(2) INFORMATION FOR SEQ ID NO:6:

(i) SEQUENCE CHARACTERISTICS:
        (A) LENGTH: 4651 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO:6:

```
CTGCAGTTCG CCAGCGAAAC GTGAATTAGA AATAGTTGAA AAAATTACCG CACTTTGCCA      60
TTTCACGCCA ACCAATATTG CAGGAAAAAC AAACCTAAAA CAGCCTACCG CTTTAATTTC     120
TAAGGTTGAT CTAGTACTTT CGCCAGATTC TGGCCCTGCC CATATTGCGA CAACACAAGG     180
TACACCCGTT ATTGGCTTGT ATGCCTATCA CAATCCTTTG CGTACTGCAC CTTATAATAA     240
TTTAGATAAC GTGGTATCTG TATATGAAGA AAATGCCCAA AAAGAATTTG GCAAACCGTC     300
TTCTGAACTA CCTTGGGCAA CCAAACTAAA AGGGAAAAAT TTGATGGCAG AGATTCAAGT     360
CGAACCCGTC ATTGAACAAA TGAAAAAATT GGGATTATTT TGAACAAATA ATCTGTATCT     420
CAAAACTTAG ATGGTTTTAA TATAGCCAAC TTGAAAGTTG TTTTTGGAAA GTAAGAACTT     480
TAGTTTTTTT AAGTTAAAAA TCAATAACTT GTTGTCAAAA TAATTATATT TAGTCATAAA     540
AATCTATACC TTAATCTCTT GCTTATTTAG TCCAATTTTT GCAGGTACAG ATTGAAATCC     600
AAAATTAGTT TGAATTTTAC GCAATTAAAT GCAAATGATT ATAAATAAAC CTATTGATTA     660
TTATTATAAT CATCATTATT ATCATCGCCA TTCTCCTATT TTTAATTATT ACAATAAGGA     720
AAACAGATGC GATTTCTAA ACTTTCCCTT GCAATTACAA CAACCTTAGT GACAGCAAAT     780
GCACTAGCGC AATCCGTTGA ATTAGACTCT ATCAACGTTA TTGCGACACG AGATCCAAGT     840
AGGTTTGCTT ATACGCCAGA AAAACAATCT AAAGATAGTC TTCTTTCTAA GCAAGCGACT     900
AGTGTTGCAG CAGCGTTAGA AGACATTCCA AATGTTGATG TTAGAGGCGG TTCGAGAAGC     960
ATTGCTCAAA AACCTAATAT CCGAGGGTTA AGTGATAATC GTGTTGTGCA AGTCATTGAT    1020
GGCGTGAGAC AAAATTTTGA TTTAGCACAT AGAGGTTCTT ATTTTCTTCC AATGTCACTT    1080
ATTCAAGAAA TTGAAGTAAT CAAAGGACCA AGTAGCTCCT TATGGGGTAG CGGTGCTTTG    1140
GGTGGTGTTG TGGCAATGCG TACGCCAAAT GCTTTAGACT TATTGAAAAA TAATGACAAA    1200
TTCGGAGTTA AAATTCGCCA AGGTTATCAA ACTGCTAATA ATTTATCGGA AAGGGATGCT    1260
TCTGTATTTG CGGCAAATGA CAAATTCGAT GTTCTTATTA GTGCTTTCTA TAATAATGCG    1320
GATAATTTAC GCACTGGTAA AGGCAACAAG CTGAATAATA CAGCCTATAA ACAGTTTGGG    1380
GGCTTAGCAA AATTTGGTTG GCAAATCAAT GATGCGAACC GTGTGGAATT ATCCCACCGC    1440
GAAACTCGTT TTAAACAAAC AGCACCAAGC AATAATGAGG TGGAAAACGA ACTTACCAAT    1500
GAAAAAATTA TAGATCAAAT CAACGAGTTC CACGGCTCAA ACAACGGTTT ACCACAGAGA    1560
GCAAAACCAT CATCAGAAAC ATCAGCGTTT TACTCTAAAG TGAAAACACG TTTTGGCAGT    1620
GTCAGTTATT TAACTGATCA ACAAATTCCT GATCAAAGCA CGGTATTTAA CTATTATTTA    1680
ACGCCAGATA ATCCTTATCT AAATACGCAT ATCGCACTGT ATAACAATAA AACTATTGAG    1740
AAAGAACAGC GTAAAGTCAG TGGTGTGAAA GATCAGACTA AATTGACTAC CCGAGGTATA    1800
AATTTACGTA ACTCTTCCGA ATTATCTCAC ATTTCCTTTG TTTATGGGGT GGATTATATG    1860
CGAGATAAAA TCCGTACCGA ACGAGGCACA AACAATAATG ATGCGAAGTT TCGAGCGGAA    1920
CCCTATAATG CGAATTCAAA CACTACAGGC GTTTATTTAA TCGCCCATAT TCCACTATTT    1980
GGGGAAAAAT TGCTACTTTC GCCAAGTGTA CGTTATGACC ACTACGATAC CTCAAGTAAA    2040
ACTGTAAAAT ACAAGGATAA TCATTTATCT CCTGCCACAA AATTGACTTG GAAAGTGACC    2100
AATTGGTTAG ATCTTTCTGC CAAATATAAT GAAGCCTTCC GAGCACCATC TATGCAAGAA    2160
CGCTTTGTGA GTGGTTCTCA CTTTGGGGCA ACTATTCTAG GAGCAGATCA TATCAATAAA    2220
TTTGTAGCAA ATCCAAATTT GCGCCCTGAA ACAGCGAAAA ATAAAGAAAT TACCGCAAAT    2280
```

```
CTACATTTTG ATAGCCTGTT TAAACAAGAC GATAAATTCA AAATTGAAGC GACTTATTTC    2340

CGTAATGATG TGAAAGATTT TATTAACTTA AAAATATTTA ATGATGCAAA TACAAGTACA    2400

AGTGCAAATG GAGCATTTTT GCCAACAAAA TCCCAGTATC AAAACATAAC TAATGCCCGT    2460

TTAAGCGGTA TTGAGTTGCA AGCTCAATAC CAAACAGAAC GTTTAACGCT GTTTACTAAC    2520

TATGGCAGTA CCAAAGGTAG AGATAAAGAT AGCGGCGAAG CTTTATCAAA CATTGCCGCA    2580

AGCAAAATCG GCGTAGGGGC AGATTATGCT TTAGTAAAAG ACAAATTCAC GGTGGGAGCG    2640

ACAATAACCC ATTACGCTGC CCAACATCGA GTGCCTAAAG ATCACGCTGT TACCTACCCA    2700

AGTTATATAC TGACCGTTCT TCGTGCTACC TATGCGCCAT TAAAAGGCGA ATGGAAAAAC    2760

CTGCGTTTAG ATTTTGCGCT GGAAAACTTG TTTGATAGAA AATATCAACC AGCGTTTAGT    2820

TTAATGGAAG GCACAGGTCG CAATGCGAAA ATTAGTGCAG TTTATAGCTT CTAAATTTAC    2880

TTTGGGAAAA CGCCCTAAAA CTGTTTTCCC TCAATTTTTG TAATTTTGTC AATTAATAAT    2940

AAATAGAACA TAAGGAATGA AAATGAGACC TCGTTATTCT GTTATTGCAA GTGCGGTCAG    3000

TTAGGCTTT GTTTTGAGTA ATTCAGTGAT GGCATTAGTG CCAAATGCTG GATCATTGAA     3060

CCGTGAACTA GAACAGCGTC AAATTCAACC AGAAGCCAAA CCTAGTGGCG AATTATTTAA    3120

TCAAGCAGCA AAATCGCCTT ATACCGCACA GTATAAACAA GAGCTAAAAT TTCCACTTAC    3180

GCAAGTACAG ATTTTAGATC GAAACAATCA GGAAGTAGTC ACAGACGAGC TTGCACATAT    3240

TTTAAAAAAT TATGTAGGAA AAGAAGTATC GCTGTCAGAT TTAAGTAATT GGCAAATGA     3300

GATCAGCGAA TTTTATCGTC ATAATAATTA TTTAGTGGCA AAAGCGATTT TACCACCGCA    3360

GGAAATTGAG CAAGGTACGG TAAAAATTCT GTTACTCAAA GGTAATGTGG GCGAAATACG    3420

CTTGCAAAAT CACAGCGCAT TAAGCAATAA ATTTGTATCC CGTCTCTCTA ATACAACAGT    3480

GAATACGTCC GAATTTATTT TGAAAGATGA GTTAGAAAAA TTTGCTTTAA CAATAAACGA    3540

TGTTCCAGGG GTAAATGCTG GTTTGCAACT CTCCGCAGGC AAAAAAGTCG GCGAAGCGAA    3600

TTTACTGATT AAGATTAACG ATGCAAAACG TTTTTCTGGT TATGTTTCAG TAGATAACCA    3660

AGGCAACAAA TATACGGGGC GTTACCGTTT GGCTGCGGGG ACAAAAGTCA GTAATTTGAA    3720

TGGCTGGGGC GATGAATTGA AACTGGATTT AATGAGTTCT AATCAGGCTA ATTTAAAAAA    3780

TGCTCGTATA GATTATTCCT CTTTAATTGA TGGTTATTCT ACGCGTTTTG GTGTAACTGC    3840

TAACTATCTC CACTACAAAT TAGGTGGTAA TTTTAAATCA TTACAATCTC AAGGGCATTC    3900

CCATACCCTA GGGGCTTATT TGTTGCACCC AACAATCCGT ACACCAAATT TTCGTTTAAG    3960

TACTAAAGTG AGCTTTAATC ATCAAAACCT TACGGATAAA CAACAAGCGG TTTCTGTGAA    4020

ACAAAAACGG AAAATAAACA GTTTAACTGC AGGGATTGAC GGTTCTTGGA ATCTTATTAA    4080

AGATGGGACA ACTTATTTTT CATTATCTAC CTTGTTCGGT AATTTAGCGA ATCAAACTAG    4140

TGAAAAACAA CATAATGCAG TAGAGAATTT TCAACCACAA TCGCATTTTA CGGTATATAA    4200

CTACCGCTTG TCTCACGAGC AAATTTTACC AAAATCTTTT GCTTTCAATA TTGGTATAAA    4260

CGGTCAGTTT GCCGATAAAA CCCTTGAAAG CTCACAGAAA ATGTTGCTTG GTGGTTTGTC    4320

TGGAGTACGT GGACATCAAG CTGGTGCGGC TTCTGTGGAT GAAGGGCATT TGATACAAAC    4380

AGAATTCAAA CATTATTTAC CAATCTTTTC CCAAAGTGTG CTAGTTAGTT CATTGTTCTA    4440

TGACTATGGT TTCGGGAAAT ATTATAAACA TAGCCAATTT CTCGCAAAAG GCGTGAAAAA    4500

TAGCGTGAAA TTACAAAGCG TTGGTGCAGG ACTTTCTCTT TCAGATGTAG GCAGCTATGC    4560

CATCAACGCT AGTATCGCTA AACCGCTTGA TAACAATATT AATAATGCCG ATAAACACCA    4620

ATTTTGGCTT TCTATGATTA AAACTTTCTA A                                   4651
```

(2) INFORMATION FOR SEQ ID NO:7:

(i) SEQUENCE CHARACTERISTICS:
        (A) LENGTH: 715 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Met Arg Phe Ser Lys Leu Ser Leu Ala Ile Thr Thr Thr Leu Val Thr
 1               5                  10                  15

Ala Asn Ala Leu Ala Gln Ser Val Glu Leu Asp Ser Ile Asn Val Ile
            20                  25                  30

Ala Thr Arg Asp Pro Ser Arg Phe Ala Tyr Thr Pro Glu Lys Gln Ser
        35                  40                  45

Lys Asp Ser Leu Leu Ser Lys Gln Ala Thr Ser Val Ala Ala Ala Leu
    50                  55                  60

Glu Asp Ile Pro Asn Val Asp Val Arg Gly Gly Ser Arg Ser Ile Ala
65                  70                  75                  80

Gln Lys Pro Asn Ile Arg Gly Leu Ser Asp Asn Arg Val Val Gln Val
                85                  90                  95

Ile Asp Gly Val Arg Gln Asn Phe Asp Leu Ala His Arg Gly Ser Tyr
            100                 105                 110

Phe Leu Pro Met Ser Leu Ile Gln Glu Ile Glu Val Ile Lys Gly Pro
        115                 120                 125

Ser Ser Ser Leu Trp Gly Ser Gly Ala Leu Gly Gly Val Val Ala Met
    130                 135                 140

Arg Thr Pro Asn Ala Leu Asp Leu Leu Lys Asn Asn Asp Lys Phe Gly
145                 150                 155                 160

Val Lys Ile Arg Gln Gly Tyr Gln Thr Ala Asn Asn Leu Ser Glu Arg
                165                 170                 175

Asp Ala Ser Val Phe Ala Ala Asn Asp Lys Phe Asp Val Leu Ile Ser
            180                 185                 190

Ala Phe Tyr Asn Asn Ala Asp Asn Leu Arg Thr Gly Lys Gly Asn Lys
        195                 200                 205

Leu Asn Asn Thr Ala Tyr Lys Gln Phe Gly Gly Leu Ala Lys Phe Gly
    210                 215                 220

Trp Gln Ile Asn Asp Ala Asn Arg Val Glu Leu Ser His Arg Glu Thr
225                 230                 235                 240

Arg Phe Lys Gln Thr Ala Pro Ser Asn Asn Glu Val Glu Asn Glu Leu
                245                 250                 255

Thr Asn Glu Lys Ile Ile Asp Gln Ile Asn Glu Phe His Gly Ser Asn
            260                 265                 270

Asn Gly Leu Pro Gln Arg Ala Lys Pro Ser Ser Glu Thr Ser Ala Phe
        275                 280                 285

Tyr Ser Lys Val Lys Thr Arg Phe Gly Ser Val Ser Tyr Leu Thr Asp
    290                 295                 300

Gln Gln Ile Pro Asp Gln Ser Thr Val Phe Asn Tyr Tyr Leu Thr Pro
305                 310                 315                 320

Asp Asn Pro Tyr Leu Asn Thr His Ile Ala Leu Tyr Asn Asn Lys Thr
                325                 330                 335

Ile Glu Lys Glu Gln Arg Lys Val Ser Gly Val Lys Asp Gln Thr Lys
            340                 345                 350
```

```
Leu Thr Thr Arg Gly Ile Asn Leu Arg Asn Ser Ser Glu Leu Ser His
        355                 360                 365

Ile Ser Phe Val Tyr Gly Val Asp Tyr Met Arg Asp Lys Ile Arg Thr
        370                 375                 380

Glu Arg Gly Thr Asn Asn Asp Ala Lys Phe Arg Ala Glu Pro Tyr
385                 390                 395                 400

Asn Ala Asn Ser Asn Thr Thr Gly Val Tyr Leu Ile Ala His Ile Pro
                    405                 410                 415

Leu Phe Gly Glu Lys Leu Leu Leu Ser Pro Ser Val Arg Tyr Asp His
                420                 425                 430

Tyr Asp Thr Ser Ser Lys Thr Val Lys Tyr Lys Asp Asn His Leu Ser
            435                 440                 445

Pro Ala Thr Lys Leu Thr Trp Lys Val Thr Asn Trp Leu Asp Leu Ser
450                 455                 460

Ala Lys Tyr Asn Glu Ala Phe Arg Ala Pro Ser Met Gln Glu Arg Phe
465                 470                 475                 480

Val Ser Gly Ser His Phe Gly Ala Thr Ile Leu Gly Ala Asp His Ile
                485                 490                 495

Asn Lys Phe Val Ala Asn Pro Asn Leu Arg Pro Glu Thr Ala Lys Asn
                500                 505                 510

Lys Glu Ile Thr Ala Asn Leu His Phe Asp Ser Leu Phe Lys Gln Asp
        515                 520                 525

Asp Lys Phe Lys Ile Glu Ala Thr Tyr Phe Arg Asn Asp Val Lys Asp
        530                 535                 540

Phe Ile Asn Leu Lys Ile Phe Asn Asp Ala Asn Thr Ser Thr Ser Ala
545                 550                 555                 560

Asn Gly Ala Phe Leu Pro Thr Lys Ser Gln Tyr Gln Asn Ile Thr Asn
                565                 570                 575

Ala Arg Leu Ser Gly Ile Glu Leu Gln Ala Gln Tyr Gln Thr Glu Arg
                580                 585                 590

Leu Thr Leu Phe Thr Asn Tyr Gly Ser Thr Lys Gly Arg Asp Lys Asp
            595                 600                 605

Ser Gly Glu Ala Leu Ser Asn Ile Ala Ala Ser Lys Ile Gly Val Gly
            610                 615                 620

Ala Asp Tyr Ala Leu Val Lys Asp Lys Phe Thr Val Gly Ala Thr Ile
625                 630                 635                 640

Thr His Tyr Ala Ala Gln His Arg Val Pro Lys Asp His Ala Val Thr
                645                 650                 655

Tyr Pro Ser Tyr Ile Leu Thr Val Leu Arg Ala Thr Tyr Ala Pro Leu
                660                 665                 670

Lys Gly Glu Trp Lys Asn Leu Arg Leu Asp Phe Ala Leu Glu Asn Leu
            675                 680                 685

Phe Asp Arg Lys Tyr Gln Pro Ala Phe Ser Leu Met Glu Gly Thr Gly
690                 695                 700

Arg Asn Ala Lys Ile Ser Ala Val Tyr Ser Phe
705                 710                 715
```

(2) INFORMATION FOR SEQ ID NO:8:

(i) SEQUENCE CHARACTERISTICS:
        (A) LENGTH: 564 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Met Lys Met Arg Pro Arg Tyr Ser Val Ile Ala Ser Ala Val Ser Leu
 1               5                  10                  15

Gly Phe Val Leu Ser Asn Ser Val Met Ala Leu Val Pro Asn Ala Gly
                20                  25                  30

Ser Leu Asn Arg Glu Leu Glu Gln Arg Gln Ile Gln Pro Glu Ala Lys
                35                  40                  45

Pro Ser Gly Glu Leu Phe Asn Gln Ala Ala Lys Ser Pro Tyr Thr Ala
 50                  55                  60

Gln Tyr Lys Gln Glu Leu Lys Phe Pro Leu Thr Gln Val Gln Ile Leu
 65                  70                  75                  80

Asp Arg Asn Asn Gln Glu Val Val Thr Asp Glu Leu Ala His Ile Leu
                85                  90                  95

Lys Asn Tyr Val Gly Lys Glu Val Ser Leu Ser Asp Leu Ser Asn Leu
                100                 105                 110

Ala Asn Glu Ile Ser Glu Phe Tyr Arg His Asn Asn Tyr Leu Val Ala
                115                 120                 125

Lys Ala Ile Leu Pro Pro Gln Glu Ile Glu Gln Gly Thr Val Lys Ile
                130                 135                 140

Leu Leu Leu Lys Gly Asn Val Gly Glu Ile Arg Leu Gln Asn His Ser
145                 150                 155                 160

Ala Leu Ser Asn Lys Phe Val Ser Arg Leu Ser Asn Thr Thr Val Asn
                165                 170                 175

Thr Ser Glu Phe Ile Leu Lys Asp Glu Leu Glu Lys Phe Ala Leu Thr
                180                 185                 190

Ile Asn Asp Val Pro Gly Val Asn Ala Gly Leu Gln Leu Ser Ala Gly
                195                 200                 205

Lys Lys Val Gly Glu Ala Asn Leu Leu Ile Lys Ile Asn Asp Ala Lys
                210                 215                 220

Arg Phe Ser Gly Tyr Val Ser Val Asp Asn Gln Gly Asn Lys Tyr Thr
225                 230                 235                 240

Gly Arg Tyr Arg Leu Ala Ala Gly Thr Lys Val Ser Asn Leu Asn Gly
                245                 250                 255

Trp Gly Asp Glu Leu Lys Leu Asp Leu Met Ser Ser Asn Gln Ala Asn
                260                 265                 270

Leu Lys Asn Ala Arg Ile Asp Tyr Ser Ser Leu Ile Asp Gly Tyr Ser
                275                 280                 285

Thr Arg Phe Gly Val Thr Ala Asn Tyr Leu His Tyr Lys Leu Gly Gly
                290                 295                 300

Asn Phe Lys Ser Leu Gln Ser Gln Gly His Ser His Thr Leu Gly Ala
305                 310                 315                 320

Tyr Leu Leu His Pro Thr Ile Arg Thr Pro Asn Phe Arg Leu Ser Thr
                325                 330                 335

Lys Val Ser Phe Asn His Gln Asn Leu Thr Asp Lys Gln Gln Ala Val
                340                 345                 350

Ser Val Lys Gln Lys Arg Lys Ile Asn Ser Leu Thr Ala Gly Ile Asp
                355                 360                 365

Gly Ser Trp Asn Leu Ile Lys Asp Gly Thr Thr Tyr Phe Ser Leu Ser
                370                 375                 380

Thr Leu Phe Gly Asn Leu Ala Asn Gln Thr Ser Glu Lys Gln His Asn
385                 390                 395                 400

Ala Val Glu Asn Phe Gln Pro Gln Ser His Phe Thr Val Tyr Asn Tyr
                405                 410                 415
```

```
-continued

Arg Leu Ser His Glu Gln Ile Leu Pro Lys Ser Phe Ala Phe Asn Ile
            420                 425                 430

Gly Ile Asn Gly Gln Phe Ala Asp Lys Thr Leu Glu Ser Ser Gln Lys
        435                 440                 445

Met Leu Leu Gly Gly Leu Ser Gly Val Arg Gly His Gln Ala Gly Ala
    450                 455                 460

Ala Ser Val Asp Glu Gly His Leu Ile Gln Thr Glu Phe Lys His Tyr
465                 470                 475                 480

Leu Pro Ile Phe Ser Gln Ser Val Leu Val Ser Ser Leu Phe Tyr Asp
                485                 490                 495

Tyr Gly Phe Gly Lys Tyr Tyr Lys His Ser Gln Phe Leu Ala Lys Gly
                500                 505                 510

Val Lys Asn Ser Val Lys Leu Gln Ser Val Gly Ala Gly Leu Ser Leu
            515                 520                 525

Ser Asp Val Gly Ser Tyr Ala Ile Asn Ala Ser Ile Ala Lys Pro Leu
            530                 535                 540

Asp Asn Asn Ile Asn Asn Ala Asp Lys His Gln Phe Trp Leu Ser Met
545                 550                 555                 560

Ile Lys Thr Phe
```